(12) United States Patent
Sung et al.

(10) Patent No.: US 7,989,425 B2
(45) Date of Patent: Aug. 2, 2011

(54) VACCINE ENHANCING THE PROTECTIVE IMMUNITY TO HEPATITIS C VIRUS USING PLASMID DNA AND RECOMBINANT ADENOVIRUS

(75) Inventors: Young Chul Sung, Pohang-si (KR); Jin-Won Youn, Incheon-si (KR); Se-Hwan Yang, Pohang-si (KR); Su-Hyung Park, Seoul (KR); Chang Geun Lee, Daegu-si (KR)

(73) Assignees: Genexine Inc., Seoul (KR); Postech Foundation, Gyeongsangbuk-Do (KR); Dong-A Pharm. Co., Ltd., Seoul (KR); Daewood Co., Ltd., Kyunggi-Do (KR); Posco, Gyeongsangbuk-Do (KR)

( * ) Notice: Subject to any disclaimer, the term of this patent is extended or adjusted under 35 U.S.C. 154(b) by 163 days.

(21) Appl. No.: 10/528,644

(22) PCT Filed: Sep. 24, 2003

(86) PCT No.: PCT/KR03/01951
§ 371 (c)(1),
(2), (4) Date: Mar. 18, 2005

(87) PCT Pub. No.: WO2004/028563
PCT Pub. Date: Apr. 8, 2004

(65) Prior Publication Data
US 2005/0287117 A1  Dec. 29, 2005

(30) Foreign Application Priority Data
Sep. 27, 2002 (KR) .................. 10-2002-0058712
Nov. 6, 2002 (KR) .................. 10-2002-0068496

(51) Int. Cl.
*A61K 39/12* (2006.01)
*C07H 23/00* (2006.01)
*C12N 1/21* (2006.01)
*C12Q 1/70* (2006.01)

(52) U.S. Cl. ........... 514/44; 536/23.1; 424/218.1; 435/5
(58) Field of Classification Search .................. None
See application file for complete search history.

(56) References Cited

U.S. PATENT DOCUMENTS
5,731,172 A * 3/1998 Saito et al. .................. 435/91.42

OTHER PUBLICATIONS

Pancholi et al. Jan. 2003, J. Virology, vol. 77, p. 382-390.*
Tang et al. May 2002, Hep. Pancreatic Disease, vol. 1, p. 228-231.*
Lechmann et al. 2000, Semin. Liver. Diseses, vol. 20, p. 211-226.*
Mikkelsen et al. 2007, Current Infect. Disese Reports, vol. 9, p. 94-101.*
Lee et al. Virology, 2001, vol. 279, p. 271-279.*
Encke (Journal of Immunology 1998, vol. 161, p. 4917-4923).*
Choo (PNAS, 1994, vol. 91, p. 1294-1298).*
Large (Journal of Immunology, 1999, vol. 162, p. 931-938).*
Xavier Forns, et al., Vaccination of Chimpanzees With Plasmid DNA Encoding the Hepatitis C Virus (HCV) Envelope E2 Protein Modified . . . Hepathology Vo. 32, No. 3, 2000.
Christine B. Bruce, et al. Replication-Deficient Recombinant Adenoviruses Expressing the Human Immunodeficiency Virus Env Antigen . . . Journal of General Virology (1999), 80, 2621-2628, Printed in Great Britain.
Nourredine Himoudi et al., Cornparative Vaccine Studies in HLA-A2.1-Transgenic Mice Reveal a Clustered Organization of Eptiopes . . . Journal of Virology, Dec. 2002, pp. 12735-12746; vol. 76, No. 24.
John W. Shiver, et al., Replication-Incompetent Adenoviral Vaccine Vector Elicits Effective Anti-Immunodeficiency-Virus Immunity, Nature, vol. 415, Jan. 17, 2002.
Rama Rao Amara, et al., Control of a Mucosal Challenge and Prevention of AIDS by a Multiprotein DNA/MVA Vaccine, Science vol. 292, Apr. 6, 2001.
Young Rim Seong, et al., Immunogenicity of the E1E2 Proteins of Hepatitis C Virus Expressed by Recombinant Adenoviruses, Vaccine 19, (2001) 2955-2964.
A: Farci, et al., 1992 "Lack of Protective Immunity Against Reinfection with Hepatitis C" *Virus Science* 258;135-140.
Lechmann, et al., 2000 "Vaccine Development for Hepatitis C" *Seminars in Liver Disease* 20(2):211-226.
Lechner et al., 2000 *J. Exp. Med.* 191(9): 1499-1512.
Et al., 2002, "New Therapeutic Strategies for Hepatitis C," *Hepatology*. 35(1):224-231.
Houghton et al., 2005 "Prospects for a vaccine against the hepatitis C virus" *Nature Insights*, 436:961-936.

* cited by examiner

*Primary Examiner* — Agnieszka Boesen
(74) *Attorney, Agent, or Firm* — Lucas & Mercanti

(57) ABSTRACT

The present invention relates to a vaccine enhancing the protective immunity to Hepatitis C virus using plasmid DNA and recombinant adenovirus, more particularly to a vaccine consisting of Δ core-E1-E2 expressing DNA vaccine, nonstructural protein NS3 and NS4 expressing DNA vaccine, nonstructural protein NS5 expressing DNA vaccine and recombinant adenovirus vaccine, and method for administration of the vaccine by priming with the DNA vaccines described above and boosting with the recombinant adenovirus vaccine thereby enhancing the protective immunity to Hepatitis C virus.

21 Claims, 21 Drawing Sheets

FIG. 20a

Amino acid sequence of core peptide pool

| Δcore (43-191) ||||
|---|---|---|---|
| No | Name | Sequence | SEQ ID NO |
| #1 | HCV43-52 | RLGVRATRKT SERSQPRGRR | 55 |
| #2 | HCV53-72 | SERSQPRGRR QPIPKARQPE | 56 |
| #3 | HCV63-82 | QPIPKARQPE GRTWAQPGYP | 57 |
| #4 | HCV73-92 | GRTWAQPGYP WPLYGNEGLG | 58 |
| #5 | HCV83-102 | WPLYGNEGLG WAGWLLSPRG | 59 |
| #6 | HCV93-112 | WAGWLLSPRG SRPSWGPTDP | 60 |
| #7 | HCV103-122 | SRPSWGPTDP RRRSRNLGKV | 61 |
| #8 | HCV113-132 | RRRSRNLGKV IDTLTCGFAD | 62 |
| #9 | HCV123-142 | IDTLTCGFAD LMGYIPLVGA | 63 |
| #10 | HCV133-152 | LMGYIPLVGA PLGGVARALA | 64 |
| #11 | HCV143-162 | PLGGVARALA HGVRLLEDGV | 65 |
| #12 | HCV153-172 | HGVRLLEDGV NYATGNLPGC | 66 |

FIG. 20b

Amino acid sequence of E2t peptide pool

| | | E2t (284-713) | | | | | |
|---|---|---|---|---|---|---|---|
| No | Name | Sequence | SEQ ID NO | No | Name | Sequence | SEQ ID NO |
| #13 | HCV384-403 | STRVTGGTEG RTTNRFVSIF | 67 | #29 | HCV554-573 | WMNSTGFTKT CGGPPCDIGG | 83 |
| #14 | HCV404-423 | ASGPSQKIQL VNNNGSWHIN | 68 | #30 | HCV564-583 | CGGPPCDIGG VGNNTLTCPT | 84 |
| #15 | HCV414-433 | VNNNGSWHIN RTALNCNDSL | 69 | #31 | HCV574-593 | VGNNTLTCPT DCFRKHPEAT | 85 |
| #16 | HCV424-443 | RTALNCNDSL SSGFIAALFY | 70 | #32 | HCV584-603 | DCFRKHPEAT YTKCGSGPWL | 86 |
| #17 | HCV434-453 | SSGFIAALFY THKFDSSGCP | 71 | #33 | HCV594-613 | YTKCGSGPWL TPRCMVDYPY | 87 |
| #18 | HCV444-463 | THKFDSSGCP ERMASCRPID | 72 | #34 | HCV604-623 | TPRCMVDYPY RLWHYPCTIN | 88 |
| #19 | HCV454-473 | ERMASCRPID KFAQGWGSIT | 73 | #35 | HCV614-633 | RLWHYPCTIN FTIFKVRMYV | 89 |
| #20 | HCV464-483 | KFAQGWGSIT YAESGGSDQR | 74 | #36 | HCV624-643 | FTIFKVRMYV GGVEHRLDAA | 90 |
| #21 | HCV474-493 | YAESGGSDQR PYCWHYAPRQ | 75 | #37 | HCV634-653 | GGVEHRLDAA CNWTRGERCD | 91 |
| #22 | HCV484-503 | PYCWHYAPRQ CGIVPASQVC | 76 | #38 | HCV644-663 | CNWTRGERCD LEDRDRSELS | 92 |
| #23 | HCV494-513 | CGIVPASQVC GPVYCFTPSP | 77 | #39 | HCV654-673 | LEDRDRSELS PLLLSTTEWQ | 93 |
| #24 | HCV504-523 | GPVYCFTPSP VVVGTTDRSG | 78 | #40 | HCV664-683 | PLLLSTTEWQ VLPCSFTTLP | 94 |
| #25 | HCV514-533 | VVVGTTDRSG APTYTWGENE | 79 | #41 | HCV674-693 | VLPCSFTTLP ALSTGLIHLH | 95 |
| #26 | HCV524-543 | APTYTWGENE TDVLLLNNTR | 80 | #42 | HCV684-703 | ALSTGLIHLH QNIVHAQHLH | 96 |
| #27 | HCV534-553 | TDVLLLNNTR PPQANWFGCT | 81 | #43 | HCV694-713 | QNIVHAQHLH GVGSAVVSIV | 97 |
| #28 | HCV544-563 | PPQANWFGCT WMNSTGFTKT | 82 | | | | |

FIG. 20c

Amino acid sequence of NS3 protease peptide pool

| \multicolumn{4}{c|}{NS3 protease (1029-1217)} | | | |
|---|---|---|---|
| No | Name | Sequence | SEQ ID NO |
| #44 | gHCV-1029 | ITAYSQQTRGLLGCIITSLT | 98 |
| #45 | gHCV-1039 | LLGCIITSLTGRDKNQVEGE | 99 |
| #46 | gHCV-1069 | FLATCVNGAWTVFHGAGSK | 100 |
| #47 | gHCV-1078 | WTVFHGAGSKTLAGPKGPIT | 101 |
| #48 | gHCV-1088 | TLAGPKGPITQMYTNVDLDL | 102 |
| #49 | gHCV-1098 | QMYTNVDLDLVGWQAPPGSR | 103 |
| #50 | gHCV-1108 | VGWQAPPGSRPLTPCTCGSS | 104 |
| #51 | gHCV-1118 | PLTPCTCGSSDLYLVTRHAD | 105 |
| #52 | gHCV-1128 | DLYLVTRHADVIPVRRRGDS | 106 |
| #53 | gHCV-1138 | VIPVRRRGDSRGSLPCPRPV | 107 |
| #54 | gHCV-1148 | RGSLPCPRPVSYLKGSSGGP | 108 |
| #55 | gHCV-1158 | SYLKGSSGGPLLCPSGHAVG | 109 |
| #56 | gHCV-1168 | LLCPSGHAVGIFRAAVCTRG | 110 |
| #57 | gHCV-1178 | IFRAAVCTRGVAKAVDFIPV | 111 |
| #58 | gHCV-1188 | VAKAVDFIPVESMETTMRSP | 112 |
| #59 | gHCV-1198 | ESMETTMRSPVFTDNSTPPA | 113 |

FIG. 20d

Amino acid sequence of Helicase peptide pool

| \multicolumn{8}{c}{NS3 helicase (1208-1656)} |||||||||
|---|---|---|---|---|---|---|---|
| No | Name | Sequence | SEQ ID NO | No | Name | Sequence | SEQ ID NO |
| #60 | HCV1208-1227 | VFTDNSTPPA VPQTFQVAHL | 114 | #77 | HCV1458-1477 | TQTVDFSLDP TFTIDTTTVP | 131 |
| #61 | HCV1218-1237 | VPQTFQVAHL HAPTGSGKST | 115 | #78 | HCV1468-1487 | TFTIDTTTVP QDAVSRSQRR | 132 |
| #62 | HCV1228-1247 | HAPTGSGKST KVPAAYAAQG | 116 | #79 | HCV1478-1497 | QDAVSRSQRR GRTGRGRRGI | 133 |
| #63 | HCV1238-1257 | KVPAAYAAQG YKVLVLNPSV | 117 | #80 | HCV1488-1507 | GRTGRGRRGI YRFVTPGERP | 134 |
| #64 | HCV1248-1267 | YKVLVLNPSV AATLGFGVYM | 118 | #81 | HCV1498-1517 | YRFVTPGERP SGMFDSSVLC | 135 |
| #65 | HCV1258-1277 | AATLGFGVYM SKAHGIDPNI | 119 | #82 | HCV1518-1537 | ECYDAGCAWY ELTPAETSVR | 136 |
| #66 | HCV1268-1287 | SKAHGIDPNI RTGVRAITTG | 120 | #83 | HCV1528-1547 | ELTPAETSVR LRAYLNTPGL | 137 |
| #67 | HCV1278-1297 | RTGVRAITTG APITYSTYGK | 121 | #84 | HCV1538-1557 | LRAYLNTPGL PVCQDHLEFW | 138 |
| #68 | HCV1318-1337 | HSTDSTSILG IGTVLDQAET | 122 | #85 | HCV1548-1567 | PVCQDHLEFW ESVFTGLTHI | 139 |
| #69 | HCV1328-1347 | IGTVLDQAET AGARLVVLAT | 123 | #86 | HCV1558-1577 | ESVFTGLTHI DAHFLSQTKQ | 140 |
| #70 | HCV1348-1367 | ATPPGSVTVP HPNIEEVALS | 124 | #87 | HCV1568-1587 | DAHFLSQTKQ AGDNFPYLVA | 141 |
| #71 | HCV1358-1377 | HPNIEEVALS NTGEIPFYGK | 125 | #88 | HCV1578-1597 | AGDNFPYLVA YQATVCARAQ | 142 |
| #72 | HCV1368-1387 | NTGEIPFYGK AIPIEVIKGG | 126 | #89 | HCV1588-1607 | YQATVCARAQ APPPSWDQMW | 143 |
| #73 | HCV1388-1407 | RHLIFCHSKK KSDELAAKLS | 127 | #90 | HCV1598-1617 | APPPSWDQMW KCLTRLKPTL | 144 |
| #74 | HCV1398-1417 | KSDELAAKLS ALGLNAVAYY | 128 | #91 | HCV1608-1627 | KCLTRLKPTL HGPTPLLYRL | 145 |
| #75 | HCV1408-1427 | ALGLNAVAYY RGLDVSVIPT | 129 | #92 | HCV1618-1637 | HGPTPLLYRL GAVQNEVTLT | 146 |
| #76 | HCV1418-1437 | RGLDVSVIPT SGDVVVVATD | 130 | #93 | HCV1628-1647 | GAVQNEVTLT HPVTKFIMAC | 147 |

FIG. 20e

Amino acid sequence of NS5A peptide pool

| NS5A (1972-2411) | | | | | | | |
|---|---|---|---|---|---|---|---|
| No | Name | Sequence | SEQ ID NO | No | Name | Sequence | SEQ ID NO |
| #94 | gHCV-1972 | SGSWLRDVWDWICTVLTDFK | 148 | #113 | gHCV-2192 | GSPPSLASSSASQLSAPSLK | 167 |
| #95 | gHCV-1982 | WICTVLTDFKTWLQSKLLPR | 149 | #114 | gHCV-2202 | ASQLSAPSLKATCTIHHDSP | 168 |
| #96 | gHCV-1992 | TWLQSKLLPRLPGVPFFSCQ | 150 | #115 | gHCV-2212 | ATCTIHHDSPDADLIEANLL | 169 |
| #97 | gHCV-2002 | LPGVPFFSCQRGYKGVWRGE | 151 | #116 | gHCV-2222 | DADLIEANLLWRQEMGGNIT | 170 |
| #98 | gHCV-2012 | RGYKGVWRGEGIMQTTCPCG | 152 | #117 | gHCV-2232 | WRQEMGGNITRVESENKVVI | 171 |
| #99 | gHCV-2022 | GIMQTTCPCGAQIAGHVKNG | 153 | #118 | gHCV-2242 | RVESENKVVILDSFEPIRAE | 172 |
| #100 | gHCV-2042 | SMRIVGPRTCSNTWHGTFPI | 154 | #119 | gHCV-2252 | LDSFEPIRAEEDEREVSVPA | 173 |
| #101 | gHCV-2052 | SNTWHGTFPINAYTTGPCSP | 155 | #120 | gHCV-2262 | EDEREVSVPAEILRRSRKFP | 174 |
| #102 | gHCV-2062 | NAYTTGPCSPSPAPNYSRAL | 156 | #121 | gHCV-2272 | EILRRSRKFPAAMPIWARPD | 175 |
| #103 | gHCV-2072 | SPAPNYSRALWRVAAEEYVE | 157 | #122 | gHCV-2292 | YNPPLLESWKDPDYVPPVVH | 176 |
| #104 | gHCV-2082 | WRVAAEEYVEVTRVGDFHYV | 158 | #123 | gHCV-2302 | DPDYVPPVVHGCPLPPTKAA | 177 |
| #105 | gHCV-2092 | VTRVGDFHYVTGVTTDNVKC | 159 | #124 | gHCV-2322 | PIPPPRRKRTIVLTESTVSS | 178 |
| #106 | gHCV-2102 | TGVTTDNVKCPCQVPAPEFF | 160 | #125 | gHCV-2332 | IVLTESTVSSALAELATKTF | 179 |
| #107 | gHCV-2122 | TELDGVRLHRYAPACKPLLR | 161 | #126 | gHCV-2342 | ALAELATKTFGGSGSWAADS | 180 |
| #108 | gHCV-2132 | YAPACKPLLRDEVSFQVGLN | 162 | #127 | gHCV-2352 | GGSGSWAADSGTATAPPDQT | 181 |
| #109 | gHCV-2152 | QYLVGSQLPCEPEPDVAVLT | 163 | #128 | gHCV-2372 | SDDGDKESDVESYSSMPPLE | 182 |
| #110 | gHCV-2162 | EPEPDVAVLTSMLTDPSHIT | 164 | #129 | gHCV-2382 | ESYSSMPPLEGEPGDPDLSD | 183 |
| #111 | gHCV-2172 | SMLTDPSHITAETAKRRLAR | 165 | #130 | gHCV-2392 | GEPGDPDLSDGSWSTVSEEA | 184 |
| #112 | gHCV-2182 | AETAKRRLARGSPPSLASSS | 166 | | | | |

SEQUENCE LISTING

```
<160> NUMBER OF SEQ ID NOS: 184

<210> SEQ ID NO 1
<211> LENGTH: 41
<212> TYPE: DNA
<213> ORGANISM: Artificial Sequence
<220> FEATURE:
<223> OTHER INFORMATION: PCR primer for HCV gene

<400> SEQUENCE: 1
aaactgcagg tgcggttaac gggaggtctc gtagaccgtg c                41

<210> SEQ ID NO 2
<211> LENGTH: 30
<212> TYPE: DNA
<213> ORGANISM: Artificial Sequence
<220> FEATURE:
<223> OTHER INFORMATION: PCR primer for HCV gene

<400> SEQUENCE: 2
ccctctagat gcgtccgcca ggagaaggaa                             30

<210> SEQ ID NO 3
<211> LENGTH: 30
<212> TYPE: DNA
<213> ORGANISM: Artificial Sequence
<220> FEATURE:
<223> OTHER INFORMATION: PCR primer for pTV2 ST

<400> SEQUENCE: 3
aaatctagaa ccatgggccc caggttgggt                             30

<210> SEQ ID NO 4
<211> LENGTH: 29
<212> TYPE: DNA
<213> ORGANISM: Artificial Sequence
<220> FEATURE:
<223> OTHER INFORMATION: PCR primer for pTZ HCV

<400> SEQUENCE: 4
cgagatctag cacccgcgtg acaggagga                              29

<210> SEQ ID NO 5
<211> LENGTH: 29
<212> TYPE: DNA
<213> ORGANISM: Artificial Sequence
<220> FEATURE:
<223> OTHER INFORMATION: PCR primer for pTZ HCV

<400> SEQUENCE: 5
gcgaattcta atactcccac ctgatcgca                              29
```

```
<210> SEQ ID NO 6
<211> LENGTH: 33
<212> TYPE: DNA
<213> ORGANISM: Artificial Sequence
<220> FEATURE:
<223> OTHER INFORMATION: PCR primer for pTV2 ST

<400> SEQUENCE: 6
aaggcgcgcc tgagcacaaa tcctaaacct caa                                  33

<210> SEQ ID NO 7
<211> LENGTH: 34
<212> TYPE: DNA
<213> ORGANISM: Artificial Sequence
<220> FEATURE:
<223> OTHER INFORMATION: PCR primer for pTV2 ST

<400> SEQUENCE: 7
cccctctaga ttatgcgtcc gccaggagaa ggaa                                 34

<210> SEQ ID NO 8
<211> LENGTH: 30
<212> TYPE: DNA
<213> ORGANISM: Artificial Sequence
<220> FEATURE:
<223> OTHER INFORMATION: PCR primer for pTV2 ST

<400> SEQUENCE: 8
aaggcgcgcc gcacccgcgt gacaggagga                                      30

<210> SEQ ID NO 9
<211> LENGTH: 30
<212> TYPE: DNA
<213> ORGANISM: Artificial Sequence
<220> FEATURE:
<223> OTHER INFORMATION: PCR primer for pTZ HCV

<400> SEQUENCE: 9
aaggcgcgcc gccccaggtt gggtgtgcgc                                      30

<210> SEQ ID NO 10
<211> LENGTH: 33
<212> TYPE: DNA
<213> ORGANISM: Artificial Sequence
<220> FEATURE:
<223> OTHER INFORMATION: PCR primer for pTZ HCV

<400> SEQUENCE: 10
aaatctagat cagtctcgca ggcccgcgtg ggc                                  33

<210> SEQ ID NO 11
<211> LENGTH: 21
<212> TYPE: DNA
<213> ORGANISM: Artificial Sequence
<220> FEATURE:
<223> OTHER INFORMATION: PCR primer for pTV2 gDsST

<400> SEQUENCE: 11
acttgagtga caatgacatc c                                               21

<210> SEQ ID NO 12
<211> LENGTH: 35
<212> TYPE: DNA
<213> ORGANISM: Artificial Sequence
<220> FEATURE:
<223> OTHER INFORMATION: PCR primer
```

```
<400> SEQUENCE: 12
aaaaatctag attaatactg ggacttgatc actat                          35

<210> SEQ ID NO 13
<211> LENGTH: 34
<212> TYPE: DNA
<213> ORGANISM: Artificial Sequence
<220> FEATURE:
<223> OTHER INFORMATION: PCR primer

<400> SEQUENCE: 13
tcgcgacccg ggcgacggcc agtgaattgt accg                           34

<210> SEQ ID NO 14
<211> LENGTH: 36
<212> TYPE: DNA
<213> ORGANISM: Artificial Sequence
<220> FEATURE:
<223> OTHER INFORMATION: PCR primer

<400> SEQUENCE: 14
tcgcgaggcg cgccacgagc cgccgcgcct ggaagg                         36

<210> SEQ ID NO 15
<211> LENGTH: 34
<212> TYPE: DNA
<213> ORGANISM: Artificial Sequence
<220> FEATURE:
<223> OTHER INFORMATION: PCR primer

<400> SEQUENCE: 15
aatattgtcg acttcagaag aactcgtcaa gaag                           34

<210> SEQ ID NO 16
<211> LENGTH: 34
<212> TYPE: DNA
<213> ORGANISM: Artificial Sequence
<220> FEATURE:
<223> OTHER INFORMATION: PCR primer

<400> SEQUENCE: 16
aatattgggc ccgaacatgt gagcaaaagg ccag                           34

<210> SEQ ID NO 17
<211> LENGTH: 36
<212> TYPE: DNA
<213> ORGANISM: Artificial Sequence
<220> FEATURE:
<223> OTHER INFORMATION: PCR primer

<400> SEQUENCE: 17
cccctgcaga ccatgcccat cacggcctac tcccaa                         36

<210> SEQ ID NO 18
<211> LENGTH: 33
<212> TYPE: DNA
<213> ORGANISM: Artificial Sequence
<220> FEATURE:
<223> OTHER INFORMATION: PCR primer

<400> SEQUENCE: 18
aaatctagat tagcatggcg tggagcagtc ctc                            33
```

```
<210> SEQ ID NO 19
<211> LENGTH: 33
<212> TYPE: DNA
<213> ORGANISM: Artificial Sequence
<220> FEATURE:
<223> OTHER INFORMATION: PCR primer

<400> SEQUENCE: 19
aaaggtacca tgtccggctc gtggctaagg gat                                   33

<210> SEQ ID NO 20
<211> LENGTH: 30
<212> TYPE: DNA
<213> ORGANISM: Artificial Sequence
<220> FEATURE:
<223> OTHER INFORMATION: PCR primer

<400> SEQUENCE: 20
aatctagaag cggttgggga gcaggtagac                                       30

<210> SEQ ID NO 21
<211> LENGTH: 25
<212> TYPE: DNA
<213> ORGANISM: Artificial Sequence
<220> FEATURE:
<223> OTHER INFORMATION: PCR primer

<400> SEQUENCE: 21
cccgggaaag tcctgccgcg cctcg                                            25

<210> SEQ ID NO 22
<211> LENGTH: 17
<212> TYPE: DNA
<213> ORGANISM: Artificial Sequence
<220> FEATURE:
<223> OTHER INFORMATION: PCR primer

<400> SEQUENCE: 22
acaacggttt ggaggga                                                     17

<210> SEQ ID NO 23
<211> LENGTH: 33
<212> TYPE: DNA
<213> ORGANISM: Artificial Sequence
<220> FEATURE:
<223> OTHER INFORMATION: PCR primer

<400> SEQUENCE: 23
gtctagagca agatgtgtca ccagcagttg gtc                                   33

<210> SEQ ID NO 24
<211> LENGTH: 33
<212> TYPE: DNA
<213> ORGANISM: Artificial Sequence
<220> FEATURE:
<223> OTHER INFORMATION: PCR primer

<400> SEQUENCE: 24
ctggatccga acctaactgc agggcacaga tgc                                   33

<210> SEQ ID NO 25
<211> LENGTH: 20
<212> TYPE: DNA
<213> ORGANISM: Artificial Sequence
<220> FEATURE:
<223> OTHER INFORMATION: PCR primer
```

<400> SEQUENCE: 25
aagatatcga attcccctc              20

<210> SEQ ID NO 26
<211> LENGTH: 21
<212> TYPE: DNA
<213> ORGANISM: Artificial Sequence
<220> FEATURE:
<223> OTHER INFORMATION: PCR primer

<400> SEQUENCE: 26
ttgccatggc catatttatc a            21

<210> SEQ ID NO 27
<211> LENGTH: 22
<212> TYPE: DNA
<213> ORGANISM: Artificial Sequence
<220> FEATURE:
<223> OTHER INFORMATION: PCR primer

<400> SEQUENCE: 27
gtaatacgac tcactatagg gc           22

<210> SEQ ID NO 28
<211> LENGTH: 21
<212> TYPE: DNA
<213> ORGANISM: Artificial Sequence
<220> FEATURE:
<223> OTHER INFORMATION: PCR primer

<400> SEQUENCE: 28
tatgagctct acaccagcag c            21

<210> SEQ ID NO 29
<211> LENGTH: 20
<212> TYPE: DNA
<213> ORGANISM: Artificial Sequence
<220> FEATURE:
<223> OTHER INFORMATION: PCR primer

<400> SEQUENCE: 29
aattaaccct cactaaaggg              20

<210> SEQ ID NO 30
<211> LENGTH: 21
<212> TYPE: DNA
<213> ORGANISM: Artificial Sequence
<220> FEATURE:
<223> OTHER INFORMATION: PCR primer

<400> SEQUENCE: 30
ggtgtagagc tcatacttga g            21

<210> SEQ ID NO 31
<211> LENGTH: 20
<212> TYPE: DNA
<213> ORGANISM: Artificial Sequence
<220> FEATURE:
<223> OTHER INFORMATION: PCR primer

<400> SEQUENCE: 31
aactcgaggt cgacggtatc              20

```
<210> SEQ ID NO 32
<211> LENGTH: 19
<212> TYPE: DNA
<213> ORGANISM: Artificial Sequence
<220> FEATURE:
<223> OTHER INFORMATION: PCR primer

<400> SEQUENCE: 32
ttctcgagcg gccgcacct                                              19

<210> SEQ ID NO 33
<211> LENGTH: 30
<212> TYPE: DNA
<213> ORGANISM: Artificial Sequence
<220> FEATURE:
<223> OTHER INFORMATION: PCR primer

<400> SEQUENCE: 33
gaagatctat gccaggttgg gtgtgcgcgc                                  30

<210> SEQ ID NO 34
<211> LENGTH: 33
<212> TYPE: DNA
<213> ORGANISM: Artificial Sequence
<220> FEATURE:
<223> OTHER INFORMATION: PCR primer

<400> SEQUENCE: 34
aaatctagat cagtactccc acttaatggc cca                              33

<210> SEQ ID NO 35
<211> LENGTH: 21
<212> TYPE: DNA
<213> ORGANISM: Artificial Sequence
<220> FEATURE:
<223> OTHER INFORMATION: PCR primer

<400> SEQUENCE: 35
tatgagctct acagcaccag c                                           21

<210> SEQ ID NO 36
<211> LENGTH: 24
<212> TYPE: DNA
<213> ORGANISM: Artificial Sequence
<220> FEATURE:
<223> OTHER INFORMATION: PCR primer

<400> SEQUENCE: 36
gctgtagagc tcatattttt actg                                        24

<210> SEQ ID NO 37
<211> LENGTH: 22
<212> TYPE: DNA
<213> ORGANISM: Artificial Sequence
<220> FEATURE:
<223> OTHER INFORMATION: PCR primer for HCV-R

<400> SEQUENCE: 37
cccgggaggg ggggtcctgg ag                                          22

<210> SEQ ID NO 38
<211> LENGTH: 29
<212> TYPE: DNA
<213> ORGANISM: Artificial Sequence
<220> FEATURE:
<223> OTHER INFORMATION: PCR primer for HCV-F
```

```
<400> SEQUENCE: 38
ccatggcgtt agtatgagtg tcgtgcagc                                    29

<210> SEQ ID NO 39
<211> LENGTH: 36
<212> TYPE: DNA
<213> ORGANISM: Artificial Sequence
<220> FEATURE:
<223> OTHER INFORMATION: Probe

<400> SEQUENCE: 39
ccgagcctta gtatgagtgt cgtgcagcct gctcgg                            36

<210> SEQ ID NO 40
<211> LENGTH: 18
<212> TYPE: DNA
<213> ORGANISM: Artificial Sequence
<220> FEATURE:
<223> OTHER INFORMATION: PCR primer for gDs

<400> SEQUENCE: 40
ggcatggggg gggctgcc                                                18

<210> SEQ ID NO 41
<211> LENGTH: 27
<212> TYPE: DNA
<213> ORGANISM: Artificial Sequence
<220> FEATURE:
<223> OTHER INFORMATION: PCR primer for gDs

<400> SEQUENCE: 41
cgagatctga gagaggcatc cgccaag                                      27

<210> SEQ ID NO 42
<211> LENGTH: 30
<212> TYPE: DNA
<213> ORGANISM: Artificial Sequence
<220> FEATURE:
<223> OTHER INFORMATION: PCR primer for HCV gene

<400> SEQUENCE: 42
cccaagctta tgagcacaaa tcctaaacct                                   30

<210> SEQ ID NO 43
<211> LENGTH: 30
<212> TYPE: DNA
<213> ORGANISM: Artificial Sequence
<220> FEATURE:
<223> OTHER INFORMATION: PCR primer for HCV gene

<400> SEQUENCE: 43
gctctagacg gggagttgcc accctgccc                                    30

<210> SEQ ID NO 44
<211> LENGTH: 30
<212> TYPE: DNA
<213> ORGANISM: Artificial Sequence
<220> FEATURE:
<223> OTHER INFORMATION: PCR primer for pTV2 gDsE2t

<400> SEQUENCE: 44
aaggcgcgcc cgatgtacgg gccagatata                                   30
```

```
<210> SEQ ID NO 45
<211> LENGTH: 30
<212> TYPE: DNA
<213> ORGANISM: Artificial Sequence
<220> FEATURE:
<223> OTHER INFORMATION: PCR primer for pTV2 gDsE2t

<400> SEQUENCE: 45
aaggcgcgcc agagaggcat ccgccaaggc                                      30

<210> SEQ ID NO 46
<211> LENGTH: 30
<212> TYPE: DNA
<213> ORGANISM: Artificial Sequence
<220> FEATURE:
<223> OTHER INFORMATION: PCR primer for pTZ HCV

<400> SEQUENCE: 46
aaactgcaga ccatgggccc caggttgggt                                      30

<210> SEQ ID NO 47
<211> LENGTH: 33
<212> TYPE: DNA
<213> ORGANISM: Artificial Sequence
<220> FEATURE:
<223> OTHER INFORMATION: PCR primer for pTZ HCV

<400> SEQUENCE: 47
aaatctagat cagtctcgca ggcccgcgtg ggc                                  33

<210> SEQ ID NO 48
<211> LENGTH: 30
<212> TYPE: DNA
<213> ORGANISM: Artificial Sequence
<220> FEATURE:
<223> OTHER INFORMATION: PCR primer for pTZ HCV

<400> SEQUENCE: 48
aaggcgcgcc ctcccatcac ggcctactcc                                      30

<210> SEQ ID NO 49
<211> LENGTH: 33
<212> TYPE: DNA
<213> ORGANISM: Artificial Sequence
<220> FEATURE:
<223> OTHER INFORMATION: PCR primer for pTZ HCV

<400> SEQUENCE: 49
aaatctagat tagcatggcg tggagcagtc ctc                                  33

<210> SEQ ID NO 50
<211> LENGTH: 2178
<212> TYPE: DNA
<213> ORGANISM: Hepatitis C virus and Herpes Simplex Virus (gDsDeltaST)

<400> SEQUENCE: 50 atggggggggg ctgccgccag gttgggggcc gtgattttgt ttgtcgtcat agtgggcctc    60 catgggtcc gcggcaaata tgccttggcg gatgcctctc tggcgcgccg ccccaggttg     120
ggtgtgcgcg cgactaggaa gacttccgag cggtcgcaac tcgtggaag gcgacagcct    180 atccccaagg ctcgccaacc cgagggtagg acctgggctc agcccgggta cccttggccc    240
ctctatggca atgagggtct gggatgggca ggatggctcc tgtcaccccg cggctctcgg    300
cctagttggg gccccacaga ccccggcgt aggtcgcgta atttgggtaa ggtcatcgat    360
actctcacat gcggcttcgc cgacctcatg ggtacattc cgctcgtcgg cgccccccta    420
```

```
ggggcgttg ccagggcctt ggcacatggt gtccggcttc tggaggacgg cgtgaactat      480
gcaacaggga atctgcctgg ttgctctttc tctatcttcc ttttggctct gttgtctggt      540
ttgaccaccc cagtttctgc ttacgaggtg cgcaacgtgt ccggggtata ccatgtcacg      600
aacgactgct ccaactcaag catcgtatat gaggcagcgg acatgatctt gcataccccc      660
gggtgcgtgc cctgcgttcg ggagggtaac tcctcccgtt gttgggtagc gctcactccc      720
acgctcgcgg ccaggaatgc cagcgttccc actacgacaa tacgacgaca cgtcgacttg      780
ctcgttgggg cggctgcttt ctgctccgct atgtacgtgg gggatctgtg cggatctgtc      840
ttcctcgtct cccagctgtt caccttctca cctcgccggc atgagacgac acaggactgc      900
aattgctcac actatcccgg ccacgtatca ggtcaccgca tggcctggga tatgatgatg      960
aattggtcgc ccacagcagc cctggtggtg tcacagatgc tccggatccc acaagctgtc     1020
gtggacatgg tggcggggc ccactgggga gtcctggcgg gccttgccta ctattccatg     1080
gtggccaact gggctaaggt tttggttgtg ctgctgcttt tgccggcgt cgatgggagc     1140 acccgcgtga caggaggaac ggaaggccgc acgaccaacc ggttcgtgag catctttgcg     1200
tccggaccat ctcagaaaat ccagcttgta acaacaacg gcagttggca catcaacagg     1260
actgctctga actgcaatga ctccctcagc tctgggttta ttgccgcact gttctacaca     1320
cacaagttcg actcgtccgg atgcccagag cgtatggcca gttgccgccc cattgacaag     1380
ttcgctcagg atgggggctc catcacgtat gctgagtctg gcggttcgga ccagaggcct     1440
tactgttggc actacgcacc ccgacagtgt ggtatcgtac ccgcatcgca ggtgtgtggt     1500
ccagtatatt gtttcacccc aagcccagtt gtagtgggga ctaccgatcg ttccggtgcc     1560
cctacgtaca cctggggga gaatgagacg gacgtgctgc tcctcaacaa cacgcggccg     1620
ccgcaagcga actggttcgg ctgtacatgg atgaatagca ctgggttcac caagacgtgc     1680 ggggccccc cgtgtgacat cggggggta ggcaacaaca ccttgacctg ccccacggat     1740
tgcttccgga agcaccccga agccacttac accaaatgtg gttcgggacc ttggttaaca     1800
cctaggtgta tggttgacta cccatacaga cttggcact ccctgcac tatcaacttt     1860 accatcttca aggtcaggat gtatgtgggg ggcgtggagc acaggctcga tgctgcgtgc     1920 aattggacc ggggagagcg gtgtgacttg aagacaggg atagatcaga gctcagcccg     1980
ctgctactgt ctacaacaga gtggcaggta ttgccctgtt ccttcaccac cctaccggcc     2040
ctgtccactg gattgattca cctccaccag aacatcgtgc acgcgcaaca cctgcacggt     2100
gtggggtcag cggttgtctc catagtgatc aagtgggagt atgtcctgtt gctcttcctt     2160
ctcctggcgg acgcataa                                                    2178
```

<210> SEQ ID NO 51
<211> LENGTH: 2841
<212> TYPE: DNA
<213> ORGANISM: Hepatitis C virus (NS34)

<400> SEQUENCE: 51

```
atggctccca tcacggccta ctcccaacag acgcggggcc tacttggttg catcatcact       60
agcctcacag gccgggacaa gaaccaagtc gaggggagg ttcaagtggt tgccaccgca      120
acacaatctt tcctggcgac ctgcgtcaat ggcgcttgga ctgtcttcca tggtgccggc      180
tcaaagaccc tagccggccc aaaggggcca attacccaaa tgtacaccaa tgtagacctg      240
gacctcgtcg gctggcaggc accccccggg tcgcgtcccc tgacaccatg cacctgcggc      300
agctcagacc tttacttggt cacgagacat gctgatgtca ttccggtgcg ccggcggggc     360
```

-continued

```
gacagtaggg ggagcctacc ctgtcccaga ccagtctcct acttgaaggg ctcctcgggt    420
ggtccactgc tctgcccttc ggggcacgct gttggcatct ttcgggctgc tgtatgcacc    480 cgggggggttg cgaaggcggt ggacttcata cccgttgaat ctatggaaac tactatgcgg   540
tctccggtct tcacagataa ctcaacccccc ccggccgtac cgcagacatt ccaagtggcc   600
catctacacg cccccactgg cagtggtaag agcactaaag tgccggctgc gtatgcagcc    660
caagggtaca aggtgcttgt cctgaacccg tccgttgccg ccaccttggg ttttggggtg    720
tatatgtcta aagcacatgg tatcgacccc aacatcagaa ctggggttag ggccatcacc    780
acgggcgccc ctattacata ctctacctat ggcaagtttc ttgccgatgg tggttgctcc    840
gggggcgcct acgacatcat aatatgtgat gagtgccact caactgactc aacttccatc    900
ttgggcattg gcacagtcct ggaccaagcg gagacggctg gagcgcggct cgtcgtgctc    960
gccaccgcta cgcctccggg atcggtcacc gtgccacacc caatatcga ggaggtggct    1020 ctgtccaaca ctggagagat ccccttctac ggcaaagcca tccccattga ggtcatcaag   1080
gggggaagac atctcatttt ctgccattcc aagaagaagt ctgacgagct cgccgcaaag   1140
ctgtcagccc tcggacttaa tgctgtagca tattaccggg gtcttgatgt gtccgtcata   1200
ccgaccagcg gagacgtcgt tgtcgtggcg acagacgctc taatgacggg ctataccggc    1260
gattttgact cagtgattga ctgtaacaca tgtgtcaccc agacagtcga ttttagcttg   1320
gatcccacct tcaccattga cacgacgacc gtgccccaag acgcagtgtc gcgctcacag   1380
cggcggggca ggactggcag gggcaggaga ggcatctaca ggtttgtgac tccaggagaa   1440
cggccttcgg gcatgttcga ttcttccgtc ctgtgtgagt gctatgacgc gggctgtgct   1500
tggtatgagc tcacgcctgc tgagacttca gttaggttgc gggcttacct gaatacacca   1560
gggttgcccg tctgccagga ccatctggag ttttgggaga gcgtcttcac aggcctcacc   1620
cacatagatg cccacttcct atcccagact aagcaggcag gagacaactt cccctatctg   1680
gtagcatacc aagccacagt gtgcgccaga gctcaagctc cgcctccatc atgggatcaa   1740
atgtggaagt gtctcacgcg gctcaaacct acgctgcacg gccaacacc cctgctgtat    1800 aggctaggag ccgtccaaaa tgaggtcacc ctcacacacc ccgtgaccaa attcatcatg   1860
gcatgcatgt cggctgacct ggaggtcgtc actagcactt gggtgctagt aggcggggtc   1920
cttgcagctc tggccgcgta ctgcttgaca acaggcagcg tggtcattgt gggcaggatc   1980
atcttgtccg ggaggccagc cgtcattccc gacaggaag tcctctaccg ggagttcgat    2040
gaaatggaag agtgcgcttc acacctccct tacatcgaac aggggatgct gctcgccgag   2100
caattcaagc agaaggcgct cgggttgctg caaatggcca ccaaacaagc ggaggctgct   2160
gctcccgtgg tggagactaa gtggcaagcc cttgaggtct tctgggcaaa gcacatgtgg   2220
aacttcatca gcgggataca gtacttggca ggcttatcca ctctgcccgg gaaccccgcg   2280
atagcatcac tgatggcatt cacatcctct atcaccagcc cgctcaccac ccaaagtacc   2340
ctcctgttta acatcctggg ggggtggggtg gctgcccagc ttgccccccc cagcgctgct   2400
tcggcttttg tgggcgctgg catcgccggt gcggccgttg gcagcatagg ccttgggaag   2460
gtgcttgtgg acatcctggc aggctatgga cagggggtgg ccggcgcact cgtgcccttt   2520
aaggtcatga gtggcgaggt gccctccacc gaggatctgg ttaatttact tcctgccatc   2580
ctgtctcctg gcgccctggt cgtcggggtt gtgtgcgcag caatactgcg ccgacacgtg   2640
ggtccaggag aggggctgt gcagtggatg aaccggctga tagcgttcgc ctcgcggggt   2700
aaccacgtct gggggacgca ctatgtgcct gagagcgacg cagcacaacg tgttactcag   2760
```

```
atcctctcca gccttaccat gactcagttg ctaaagaggc ttcaccagtg gattaatgag   2820
gactgctcca cgccatgcta a                                             2841

<210> SEQ ID NO 52
<211> LENGTH: 3123
<212> TYPE: DNA
<213> ORGANISM: Hepatitis C virus (NS5)

<400> SEQUENCE: 52
atgtccggct cgtggctaag ggatgtctgg gactggatat gcacggtgct gacagacttc     60
aagacctggc tccagtccaa gcttctgccg cggttaccgg gcgtcccttt cttctcgtgc    120
caacgcgggt acaagggagt ctggcggggg gaaggcatca tgcaaaccac ctgcccatgt    180
ggagcacaga tcgccggaca tgtcaaaaac ggttccatga ggatcgtcgg gcctagaacc    240
tgcagcaaca cgtggcatgg aacatttccc atcaacgcat acaccacggg cccttgctcg    300
ccctccccgg cgccaaatta ttccagggcg ctgtggcggg tggccgctga ggagtacgtg    360
gaggttacgc gggtggggga tttccactac gtgacgggcg tgaccactga caacgtgaaa    420
tgcccatgcc aggttccggc ccctgaattc ttcacagaat tggatggggt gcggttgcac    480
aggtacgctc cggcgtgcaa gcctctccta cgggatgagg tctcattcca ggtcgggctc    540
aaccaatacc tggttggatc gcagctccca tgcgagcccg aaccggatgt agcagtgctc    600
acttccatgc tcaccgaccc ctcccacatt acagcagaga cggctaagcg taggctggcc    660
agagggtctc ccccctcctt ggccagctct tcagctagcc agttgtctgc gccttccttg    720
aaggcgacat gcaccatcca tcatgactcc ccggacgccg acctcattga ggccaacctc    780
ctgtggcggc aggagatggg cgggaacatc acccgtgtgg agtcagagaa taaggtagtg    840
atactggact ctttcgaacc gattcgagcg gaggaggatg agagggaagt atccgttccg    900
gcggagatcc tgcggagatc taggaagttc cccgcagcga tgcccatatg ggcacgcccg    960
gattacaatc ctcccctgct agagtcctgg aaggatccgg actacgttcc tccggtagta   1020
cacggatgcc cattgccacc taccaaggcc gctccgatac cacccccacg gaggaagagg   1080
acgattgtcc tgacagagtc cactgtgtct tctgccttgg cggagctcgc tactaagacc   1140
ttcggcggct ccggatcgtg ggccgccgac agcggcacgg cgactgcccc tcctgaccag   1200
acctccgacg acggcgacaa agaatctgac gttgagtcgt actcctccat gccccccctt   1260
gagggagagc cgggggaccc cgatctcagc gacgggtctt ggtccaccgt gagcgaggaa   1320
gccagtgagg acgtcgtctg ctgctcgatg tcctacacat ggacgggcgc cctgatcacg   1380
ccatgcgctg cggaggaaag caagctgccc atcaacccgt tgagcaactc cttgctgcgt   1440
caccacaata tggtgtacgc cacaacatcc gcgagcgcaa gtctgcggca gaagaaggtc   1500
acctttgaca gactgcaagt cctggacgat cactaccggg acgtgctcaa ggagatgaag   1560
gcgaaggcgt ccacagttaa ggccaaactt ctatctgtag aggaagcctg caagctgacg   1620
cccccacatt cggccaaatc aaaatttggc tatggggcga aggacgtccg gagcctatcc   1680
agcagggccg tcaaccacat cacctccgtg tggaaggact tgctggaaga cactaagaca   1740
ccaattgaca ccaccatcat ggcaaaaaat gaggttttct gcgtccaacc agagaaagga   1800
ggccgcaagc cagctcgcct tatcgtattt ccagacctgg gagttcgtgt atgcgagaag   1860
atggccctct acgacgtggt atccaccctc cctcaggccg tgatgggctc ctcatacggg   1920
ttccagtatt ctcctgggca gcgggtcgag ttcctggtga aaacctggaa atcgaagaaa   1980
tgccccatgg gcttttcata tgacacccgc tgctttgact caacggtcac tgagaatgac   2040
```

```
atccgtattg aggagtcgat ttaccaatgt tgtgacttgg cccccgaagc caggcaggtc    2100
ataaggtcgc tcacagaacg gctttatatc gggggtccct tgactaattc aaaagggcag    2160
aactgcggtt atcgccggtg ccgcgcaagc ggcgtgctga cgactagctg cggcaatact    2220
ctcacatgtt acttgaaggc ctctgctgcc tgtcgagctg cgaagctcca ggactgcacg    2280
atgctcgtga acggagacga ccttgtcgtt atctgtgaga gcgcgggaac ccgagaggat    2340
gcggcgagcc tacgagtctt cacggaggct atgactaggt actctgcccc ccccggggac    2400
ccgcctcaac cggaatatga cttggagttg ataacatcat gttcctccaa tgtgtcggtc    2460
gcgcacgatg catccggcaa aagggtgtac tacctcaccc gtgaccccac cacccccctt    2520
gcgcgggctg cgtgggagac agctagacac actccagtta actcctggct gggcaacatc    2580
atcatgtatg cgcccacctt ctgggcaagg atgattctga tgactcactt cttctccatc    2640
cttctagccc aggagcaact tggaaaggcc ctagattgtc agatctacgg ggcctgttac    2700
tccattgagc cacttgacct acctcagatc attgagcgac tccatggtct tagcgcattt    2760
tcactccata gttactctcc aggtgagatc aatagggtgg cttcatgcct caggaaactt    2820
ggggttccac ccttgcgagt ctggagacat cgggccagaa gtgtccgcgc taagctgctg    2880
tcccaggggg ggagggccgc cacatgtggc aagtacctct tcaactgggc agtaaggacc    2940
aagcttaagc tcactccaat cccagctgcg tcccagttgg acttgtccag ctggttcgtt    3000
gctggttaca gtgggggaga catatatcac agcctgtctc gtgcccgacc ccgctggttc    3060
atgttatgcc tactcctact ttctgtaggg gtaggcgtct acctgctccc caaccgcttc    3120
tag                                                                  3123
```

<210> SEQ ID NO 53  
<211> LENGTH: 2390  
<212> TYPE: DNA  
<213> ORGANISM: Homo sapiens (hIL-12m)

<400> SEQUENCE: 53

```
atgtggcccc tgggtcagc ctcccagcca ccgccctcac ctgccgcggc cacaggtctg      60
catccagcgg ctcgccctgt gtccctgcag tgccggctca gcatgtgtcc agcgcgcagc     120
ctcctccttg tggctaccct ggtcctcctg gaccacctca gtttggccag aaacctcccc     180
gtggccactc cagacccagg aatgttccca tgccttcacc actcccaaaa cctgctgagg     240
gccgtcagca acatgctcca gaaggccaga caaactctag aattttaccc ttgcacttct     300
gaagagattg atcatgaaga tatcacaaaa gataaaacca gcacagtgga ggcctgttta     360
ccattggaat taaccaagaa tgagagttgc ctaaattcca gagagacctc tttcataact     420
aatgggagtt gcctggcctc cagaaagacc tcttttatga tggccctgtg ccttagtagt     480
atttatgaag acttgaagat gtaccaggtg gagttcaaga ccatgaatgc aaagcttctg     540
atggatccta gaggcagat cttttctagat caaaacatgc tggcagttat tgatgagctg     600
atgcaggccc tgaatttcaa cagtgagact gtgccacaaa atcctccct tgaagaaccg     660 gatttttata aaactaaaat caagctctgc atacttcttc atgctttcag aattcgggca     720
gtgactattg atagagtgat gagctatctg aatgcttcct aaaaagagag gtccctccaa     780
accgttgtgg gggatccact agttctagag cggccatcga attccccctc tcctccccc     840 cccctaacgt tactggccga agccgcttgg aataaggccg gtgtgcgttt gtctatatgt     900 tatttttccac catattgccg tcttttggca atgtgagggc ccggaaacct ggccctgtct     960
tcttgacgag cattcctagg ggtctttccc ctctcgccaa aggaatgcaa ggtctgttga    1020
```

```
atgtcgtgaa ggaagcagtt cctctggaag cttcttgaag acaaacaacg tctgtagcga   1080 cccctttgcag gcagcggaac cccccacctg gcgacaggtg cctctgcggc caaaagccac   1140
gtgtataaga tacacctgca aaggcggcac aaccccagtg ccacgttgtg agttggatag   1200
ttgtggaaag agtcaaatgg ctctcctcaa gcgtattcaa caaggggctg aaggatgccc   1260
agaaggtacc ccattgtatg ggatctgatc tggggcctcg gtgcacatgc tttacatgtg   1320
tttagtcgag gttaaaaaac gtctaggccc cccgaaccac ggggacgtgg ttttcctttg   1380
aaaaacacga tgataatatg ccatgggtc accagcagtt ggtcatctct tggttttccc   1440
tggtttttct ggcatctccc ctcgtggcca tgggaact gaagaaagat gtttatgtcg   1500
tagaattgga ttggtatccg gatgccctg gagaaatggt ggtcctcacc tgtgacaccc   1560
ctgaagaaga tggtatcacc tggaccttgg accagagcag tgaggtctta ggctctggca   1620
aaaccctgac catccaagtc aaagagtttg agatgctggc cagtacacc tgtcacaaag   1680 gaggcgaggt tctaagccat tcgctcctgc tgcttcacaa aaaggaagat ggaatttggt   1740
ccactgatat tttaaaggac cagaaagaac ccaaaaataa gaccttttcta agatgcgagg   1800 ccaagaatta ttctggacgt ttcacctgct ggtggctgac gacaatcagt actgatttga   1860
cattcagtgt caaaagcagc agaggctctt ctgaccccca aggggtgacg tgcggagctg   1920
ctacactctc tgcagagaga gtcagagggg acaacaagga gtatgagtac tcagtggagt   1980
gccaggagga cagtgcctgc ccagctgctg aggagagtct gcccattgag gtcatggtgg   2040
atgccgttca caagctcaag tatgagtctc acaccagcag cttcttcatc agggacatca   2100
tcaaacctga cccacccaag aacttgcagc tgaagccatt aaagaattct cggcaggtgg   2160
aggtcagctg ggagtaccct gacacctgga gtactccaca ttcctacttc tccctgacat   2220
tctgcgttca ggtccagggc aagagcaaga gagaaaagaa agatagagtc ttcacggaca   2280
agacctcagc cacggtcatc tgccgcaaaa atgccagcat tagcgtgcgg gcccaggacc   2340
gctactatag ctcatcttgg agcgaatggg catctgtgcc ctgcagttag                2390
```

<210> SEQ ID NO 54
<211> LENGTH: 2946
<212> TYPE: DNA
<213> ORGANISM: Hepatitis C virus and Herpes simplex virus (gDsNS34)

<400> SEQUENCE: 54

```
atgggggggg ctgccgccag gttgggggcc gtgattttgt tgtcgtcat agtgggcctc     60 catgggtcc gcggcaaata tgccttggcg gatgcctctc tggcgcgccc tcccatcacg    120
gcctactccc aacagacgcg gggcctactt ggttgcatca tcactagcct cacaggccgg    180
gacaagaacc aagtcgaggg ggaggttcaa gtggttgcca ccgcaacaca atctttcctg    240
gcgacctgcg tcaatggcgc ttggactgtc ttccatggtg ccggctcaaa gaccctagcc    300
ggcccaaagg ggccaattac ccaaatgtac accaatgtag acctggacct cgtcggctgg    360
caggcacccc ccgggtcgcg tcccctgaca ccatgcacct gcggcagctc agacctttac    420
ttggtcacga gacatgctga tgtcattccg gtgcgccggc ggggcgacag tagggggagc    480
ctaccctgtc ccagaccagt ctcctacttg aagggctcct cgggtggtcc actgctctgc    540 ccttcgggc acgctgttgg catctttcgg gctgctgtat gcacccgggg ggttgcgaag    600
gcggtggact tcataccccgt tgaatctatg gaaactacta tgcggtctcc ggtcttcaca    660
gataactcaa ccccccggc cgtaccgcag acattccaag tggcccatct acacgccccc    720
actggcagtg gtaagagcac taaagtgccg gctgcgtatg cagcccaagg gtacaaggtg    780
```

```
cttgtcctga acccgtccgt tgccgccacc ttgggttttg gggtgtatat gtctaaagca    840
catggtatcg accccaacat cagaactggg gttagggcca tcaccacggg cgcccctatt    900
acatactcta cctatggcaa gtttcttgcc gatggtggtt gctccggggg cgcctacgac    960
atcataatat gtgatgagtg ccactcaact gactcaactt ccatcttggg cattggcaca   1020
gtcctggacc aagcggagac ggctggagcg cggctcgtcg tgctcgccac cgctacgcct   1080
ccgggatcgg tcaccgtgcc acaccccaat atcgaggagg tggctctgtc caacactgga   1140
gagatcccct tctacggcaa agccatcccc attgaggtca tcaaggggggg aagacatctc   1200
attttctgcc attccaagaa gaagtctgac gagctcgccg caaagctgtc agccctcgga   1260
cttaatgctg tagcatatta ccggggtctt gatgtgtccg tcataccgac cagcggagac   1320
gtcgttgtcg tggcgacaga cgctctaatg acgggctata ccggcgattt tgactcagtg   1380
attgactgta acacatgtgt cacccagaca gtcgatttta gcttggatcc caccttcacc   1440
attgacacga cgaccgtgcc ccaagacgca gtgtcgcgct cacagcggcg gggcaggact   1500
ggcaggggca ggagaggcat ctacaggttt gtgactccag gagaacggcc ttcgggcatg   1560
ttcgattctt ccgtcctgtg tgagtgctat gacgcgggct gtgcttggta tgagctcacg   1620
cctgctgaga cttcagttag gttgcgggct tacctgaata caccagggtt gcccgtctgc   1680
caggaccatc tggagttttg ggagagcgtc ttcacaggcc tcacccacat agatgcccac   1740
ttcctatccc agactaagca ggcaggagac aacttcccct atctggtagc ataccaagcc   1800
acagtgtgcg ccagagctca agctccgcct ccatcatggg atcaaatgtg gaagtgtctc   1860
acgcggctca aacctacgct gcacgggcca acacccctgc tgtataggct aggagccgtc   1920
caaaatgagg tcaccctcac acaccccgtg accaaattca tcatggcatg catgtcggct   1980
gacctggagg tcgtcactag cacttgggtg ctagtaggcg gggtccttgc agctctggcc   2040
gcgtactgct tgacaacagg cagcgtggtc attgtgggca ggatcatctt gtccgggagg   2100
ccagccgtca ttcccgacag ggaagtcctc taccgggagt tcgatgaaat ggaagagtgc   2160
gcttcacacc tcccttacat cgaacagggg atgctgctcg ccgagcaatt caagcagaag   2220
gcgctcgggt tgctgcaaat ggccaccaaa caagcggagg ctgctgctcc cgtggtggag   2280
actaagtggc aagcccttga ggtcttctgg gcaaagcaca tgtggaactt catcagcggg   2340
atacagtact tggcaggctt atccactctg cccgggaacc ccgcgatagc atcactgatg   2400
gcattcacat cctctatcac cagcccgctc accacccaaa gtaccctcct gtttaacatc   2460
ctggggggt gggtggctgc ccagcttgcc ccccccagcg ctgcttcggc ttttgtgggc   2520
gctggcatcg ccggtgcggc cgttggcagc ataggccttg ggaaggtgct tgtggacatc   2580
ctggcaggct atggagcagg ggtggccggc gcactcgtgg ccttttaaggt catgagtggc   2640
gaggtgccct ccaccgagga tctggttaat ttacttcctg ccatcctgtc tcctggcgcc   2700
ctggtcgtcg gggttgtgtg cgcagcaata ctgcgccgac acgtgggtcc aggagagggg   2760
gctgtgcagt ggatgaaccg gctgatagcg ttcgcctcgc ggggtaacca cgtctggggg   2820
acgcactatg tgcctgagag cgacgcagca caacgtgtta ctcagatcct ctccagcctt   2880
accatgactc agttgctaaa gaggcttcac cagtggatta atgaggactg ctccacgcca   2940
tgctaa                                                              2946
```

<210> SEQ ID NO 55
<211> LENGTH: 20
<212> TYPE: PRT
<213> ORGANISM: Artificial Sequence -continued

```
<220> FEATURE:
<223> OTHER INFORMATION: HCV43-52

<400> SEQUENCE: 55

Arg Leu Gly Val Arg Ala Thr Arg Lys Thr Ser Glu Arg Ser Gln Pro
1               5                   10                  15

Arg Gly Arg Arg
            20

<210> SEQ ID NO 56
<211> LENGTH: 20
<212> TYPE: PRT
<213> ORGANISM: Artificial Sequence
<220> FEATURE:
<223> OTHER INFORMATION: HCV53-72

<400> SEQUENCE: 56

Ser Glu Arg Ser Gln Pro Arg Gly Arg Arg Gln Pro Ile Pro Lys Ala
1               5                   10                  15

Arg Gln Pro Glu
            20

<210> SEQ ID NO 57
<211> LENGTH: 20
<212> TYPE: PRT
<213> ORGANISM: Artificial Sequence
<220> FEATURE:
<223> OTHER INFORMATION: HCV63-82

<400> SEQUENCE: 57

Gln Pro Ile Pro Lys Ala Arg Gln Pro Glu Gly Arg Thr Trp Ala Gln
1               5                   10                  15

Pro Gly Tyr Pro
            20

<210> SEQ ID NO 58
<211> LENGTH: 20
<212> TYPE: PRT
<213> ORGANISM: Artificial Sequence
<220> FEATURE:
<223> OTHER INFORMATION: HCV73-92

<400> SEQUENCE: 58

Gly Arg Thr Trp Ala Gln Pro Gly Tyr Pro Trp Pro Leu Tyr Gly Asn
1               5                   10                  15

Glu Gly Leu Gly
            20

<210> SEQ ID NO 59
<211> LENGTH: 20
<212> TYPE: PRT
<213> ORGANISM: Artificial Sequence
<220> FEATURE:
<223> OTHER INFORMATION: HCV83-102

<400> SEQUENCE: 59

Trp Pro Leu Tyr Gly Asn Glu Gly Leu Gly Trp Ala Gly Trp Leu Leu
1               5                   10                  15

Ser Pro Arg Gly
            20

<210> SEQ ID NO 60
<211> LENGTH: 20
<212> TYPE: PRT
<213> ORGANISM: Artificial Sequence
```

```
<220> FEATURE:
<223> OTHER INFORMATION: HCV93-112

<400> SEQUENCE: 60

Trp Ala Gly Trp Leu Leu Ser Pro Arg Gly Ser Arg Pro Ser Trp Gly
1               5                   10                  15

Pro Thr Asp Pro
            20

<210> SEQ ID NO 61
<211> LENGTH: 20
<212> TYPE: PRT
<213> ORGANISM: Artificial Sequence
<220> FEATURE:
<223> OTHER INFORMATION: HCV103-122

<400> SEQUENCE: 61

Ser Arg Pro Ser Trp Gly Pro Thr Asp Pro Arg Arg Arg Ser Arg Asn
1               5                   10                  15

Leu Gly Lys Val
            20

<210> SEQ ID NO 62
<211> LENGTH: 20
<212> TYPE: PRT
<213> ORGANISM: Artificial Sequence
<220> FEATURE:
<223> OTHER INFORMATION: HCV113-132

<400> SEQUENCE: 62

Arg Arg Arg Ser Arg Asn Leu Gly Lys Val Ile Asp Thr Leu Thr Cys
1               5                   10                  15

Gly Phe Ala Asp
            20

<210> SEQ ID NO 63
<211> LENGTH: 20
<212> TYPE: PRT
<213> ORGANISM: Artificial Sequence
<220> FEATURE:
<223> OTHER INFORMATION: HCV123-142

<400> SEQUENCE: 63

Ile Asp Thr Leu Thr Cys Gly Phe Ala Asp Leu Met Gly Tyr Ile Pro
1               5                   10                  15

Leu Val Gly Ala
            20

<210> SEQ ID NO 64
<211> LENGTH: 20
<212> TYPE: PRT
<213> ORGANISM: Artificial Sequence
<220> FEATURE:
<223> OTHER INFORMATION: HCV133-152

<400> SEQUENCE: 64

Leu Met Gly Tyr Ile Pro Leu Val Gly Ala Pro Leu Gly Gly Val Ala
1               5                   10                  15

Arg Ala Leu Ala
            20

<210> SEQ ID NO 65
<211> LENGTH: 20
<212> TYPE: PRT
<213> ORGANISM: Artificial Sequence
```

-continued

```
<220> FEATURE:
<223> OTHER INFORMATION: HCV143-162

<400> SEQUENCE: 65

Pro Leu Gly Gly Val Ala Arg Ala Leu Ala His Gly Val Arg Leu Leu
1               5                   10                  15

Glu Asp Gly Val
            20

<210> SEQ ID NO 66
<211> LENGTH: 20
<212> TYPE: PRT
<213> ORGANISM: Artificial Sequence
<220> FEATURE:
<223> OTHER INFORMATION: HCV153-172

<400> SEQUENCE: 66

His Gly Val Arg Leu Leu Glu Asp Gly Val Asn Tyr Ala Thr Gly Asn
1               5                   10                  15

Leu Pro Gly Cys
            20

<210> SEQ ID NO 67
<211> LENGTH: 20
<212> TYPE: PRT
<213> ORGANISM: Artificial Sequence
<220> FEATURE:
<223> OTHER INFORMATION: HCV384-403

<400> SEQUENCE: 67

Ser Thr Arg Val Thr Gly Gly Thr Glu Gly Arg Thr Thr Asn Arg Phe
1               5                   10                  15

Val Ser Ile Phe
            20

<210> SEQ ID NO 68
<211> LENGTH: 20
<212> TYPE: PRT
<213> ORGANISM: Artificial Sequence
<220> FEATURE:
<223> OTHER INFORMATION: HCV404-423

<400> SEQUENCE: 68

Ala Ser Gly Pro Ser Gln Lys Ile Gln Leu Val Asn Asn Asn Gly Ser
1               5                   10                  15

Trp His Ile Asn
            20

<210> SEQ ID NO 69
<211> LENGTH: 20
<212> TYPE: PRT
<213> ORGANISM: Artificial Sequence
<220> FEATURE:
<223> OTHER INFORMATION: HCV414-433

<400> SEQUENCE: 69

Val Asn Asn Asn Gly Ser Trp His Ile Asn Arg Thr Ala Leu Asn Cys
1               5                   10                  15

Asn Asp Ser Leu
            20

<210> SEQ ID NO 70
<211> LENGTH: 20
<212> TYPE: PRT
<213> ORGANISM: Artificial Sequence
```

```
<220> FEATURE:
<223> OTHER INFORMATION: HCV424-443

<400> SEQUENCE: 70

Arg Thr Ala Leu Asn Cys Asn Asp Ser Leu Ser Ser Gly Phe Ile Ala
1               5                   10                  15

Ala Leu Phe Tyr
            20

<210> SEQ ID NO 71
<211> LENGTH: 20
<212> TYPE: PRT
<213> ORGANISM: Artificial Sequence
<220> FEATURE:
<223> OTHER INFORMATION: HCV434-453

<400> SEQUENCE: 71

Ser Ser Gly Phe Ile Ala Ala Leu Phe Tyr Thr His Lys Phe Asp Ser
1               5                   10                  15

Ser Gly Cys Pro
            20

<210> SEQ ID NO 72
<211> LENGTH: 20
<212> TYPE: PRT
<213> ORGANISM: Artificial Sequence
<220> FEATURE:
<223> OTHER INFORMATION: HCV444-463

<400> SEQUENCE: 72

Thr His Lys Phe Asp Ser Ser Gly Cys Pro Glu Arg Met Ala Ser Cys
1               5                   10                  15

Arg Pro Ile Asp
            20

<210> SEQ ID NO 73
<211> LENGTH: 20
<212> TYPE: PRT
<213> ORGANISM: Artificial Sequence
<220> FEATURE:
<223> OTHER INFORMATION: HCV454-473

<400> SEQUENCE: 73

Glu Arg Met Ala Ser Cys Arg Pro Ile Asp Lys Phe Ala Gln Gly Trp
1               5                   10                  15

Gly Ser Ile Thr
            20

<210> SEQ ID NO 74
<211> LENGTH: 20
<212> TYPE: PRT
<213> ORGANISM: Artificial Sequence
<220> FEATURE:
<223> OTHER INFORMATION: HCV464-483

<400> SEQUENCE: 74

Lys Phe Ala Gln Gly Trp Gly Ser Ile Thr Tyr Ala Glu Ser Gly Gly
1               5                   10                  15

Ser Asp Gln Arg
            20

<210> SEQ ID NO 75
<211> LENGTH: 20
<212> TYPE: PRT
<213> ORGANISM: Artificial Sequence
```

-continued

```
<220> FEATURE:
<223> OTHER INFORMATION: HCV474-493

<400> SEQUENCE: 75

Tyr Ala Glu Ser Gly Gly Ser Asp Gln Arg Pro Tyr Cys Trp His Tyr
1               5                   10                  15

Ala Pro Arg Gln
            20

<210> SEQ ID NO 76
<211> LENGTH: 20
<212> TYPE: PRT
<213> ORGANISM: Artificial Sequence
<220> FEATURE:
<223> OTHER INFORMATION: HCV484-503

<400> SEQUENCE: 76

Pro Tyr Cys Trp His Tyr Ala Pro Arg Gln Cys Gly Ile Val Pro Ala
1               5                   10                  15

Ser Gln Val Cys
            20

<210> SEQ ID NO 77
<211> LENGTH: 20
<212> TYPE: PRT
<213> ORGANISM: Artificial Sequence
<220> FEATURE:
<223> OTHER INFORMATION: HCV494-513

<400> SEQUENCE: 77

Cys Gly Ile Val Pro Ala Ser Gln Val Cys Gly Pro Val Tyr Cys Phe
1               5                   10                  15

Thr Pro Ser Pro
            20

<210> SEQ ID NO 78
<211> LENGTH: 20
<212> TYPE: PRT
<213> ORGANISM: Artificial Sequence
<220> FEATURE:
<223> OTHER INFORMATION: HCV504-523

<400> SEQUENCE: 78

Gly Pro Val Tyr Cys Phe Thr Pro Ser Pro Val Val Val Gly Thr Thr
1               5                   10                  15

Asp Arg Ser Gly
            20

<210> SEQ ID NO 79
<211> LENGTH: 20
<212> TYPE: PRT
<213> ORGANISM: Artificial Sequence
<220> FEATURE:
<223> OTHER INFORMATION: HCV514-533

<400> SEQUENCE: 79

Val Val Val Gly Thr Thr Asp Arg Ser Gly Ala Pro Thr Tyr Thr Trp
1               5                   10                  15

Gly Glu Asn Glu
            20

<210> SEQ ID NO 80
<211> LENGTH: 20
<212> TYPE: PRT
<213> ORGANISM: Artificial Sequence
```

```
<220> FEATURE:
<223> OTHER INFORMATION: HCV524-543

<400> SEQUENCE: 80

Ala Pro Thr Tyr Thr Trp Gly Glu Asn Glu Thr Asp Val Leu Leu Leu
1               5                   10                  15

Asn Asn Thr Arg
            20

<210> SEQ ID NO 81
<211> LENGTH: 20
<212> TYPE: PRT
<213> ORGANISM: Artificial Sequence
<220> FEATURE:
<223> OTHER INFORMATION: HCV534-553

<400> SEQUENCE: 81

Thr Asp Val Leu Leu Leu Asn Asn Thr Arg Pro Pro Gln Ala Asn Trp
1               5                   10                  15

Phe Gly Cys Thr
            20

<210> SEQ ID NO 82
<211> LENGTH: 20
<212> TYPE: PRT
<213> ORGANISM: Artificial Sequence
<220> FEATURE:
<223> OTHER INFORMATION: HCV544-563

<400> SEQUENCE: 82

Pro Pro Gln Ala Asn Trp Phe Gly Cys Thr Trp Met Asn Ser Thr Gly
1               5                   10                  15

Phe Thr Lys Thr
            20

<210> SEQ ID NO 83
<211> LENGTH: 20
<212> TYPE: PRT
<213> ORGANISM: Artificial Sequence
<220> FEATURE:
<223> OTHER INFORMATION: HCV554-573

<400> SEQUENCE: 83

Trp Met Asn Ser Thr Gly Phe Thr Lys Thr Cys Gly Gly Pro Pro Cys
1               5                   10                  15

Asp Ile Gly Gly
            20

<210> SEQ ID NO 84
<211> LENGTH: 20
<212> TYPE: PRT
<213> ORGANISM: Artificial Sequence
<220> FEATURE:
<223> OTHER INFORMATION: HCV564-583

<400> SEQUENCE: 84

Cys Gly Gly Pro Pro Cys Asp Ile Gly Gly Val Gly Asn Asn Thr Leu
1               5                   10                  15

Thr Cys Pro Thr
            20

<210> SEQ ID NO 85
<211> LENGTH: 20
<212> TYPE: PRT
<213> ORGANISM: Artificial Sequence
```

```
<220> FEATURE:
<223> OTHER INFORMATION: HCV574-593

<400> SEQUENCE: 85

Val Gly Asn Asn Thr Leu Thr Cys Pro Thr Asp Cys Phe Arg Lys His
1               5                   10                  15

Pro Glu Ala Thr
            20

<210> SEQ ID NO 86
<211> LENGTH: 20
<212> TYPE: PRT
<213> ORGANISM: Artificial Sequence
<220> FEATURE:
<223> OTHER INFORMATION: HCV584-603

<400> SEQUENCE: 86

Asp Cys Phe Arg Lys His Pro Glu Ala Thr Tyr Thr Lys Cys Gly Ser
1               5                   10                  15

Gly Pro Trp Leu
            20

<210> SEQ ID NO 87
<211> LENGTH: 20
<212> TYPE: PRT
<213> ORGANISM: Artificial Sequence
<220> FEATURE:
<223> OTHER INFORMATION: HCV594-613

<400> SEQUENCE: 87

Tyr Thr Lys Cys Gly Ser Gly Pro Trp Leu Thr Pro Arg Cys Met Val
1               5                   10                  15

Asp Tyr Pro Tyr
            20

<210> SEQ ID NO 88
<211> LENGTH: 20
<212> TYPE: PRT
<213> ORGANISM: Artificial Sequence
<220> FEATURE:
<223> OTHER INFORMATION: HCV604-623

<400> SEQUENCE: 88

Thr Pro Arg Cys Met Val Asp Tyr Pro Tyr Arg Leu Trp His Tyr Pro
1               5                   10                  15

Cys Thr Ile Asn
            20

<210> SEQ ID NO 89
<211> LENGTH: 20
<212> TYPE: PRT
<213> ORGANISM: Artificial Sequence
<220> FEATURE:
<223> OTHER INFORMATION: HCV614-633

<400> SEQUENCE: 89

Arg Leu Trp His Tyr Pro Cys Thr Ile Asn Phe Thr Ile Phe Lys Val
1               5                   10                  15

Arg Met Tyr Val
            20

<210> SEQ ID NO 90
<211> LENGTH: 20
<212> TYPE: PRT
<213> ORGANISM: Artificial Sequence
```

<220> FEATURE:
<223> OTHER INFORMATION: HCV624-643

<400> SEQUENCE: 90

Phe Thr Ile Phe Lys Val Arg Met Tyr Val Gly Gly Val Glu His Arg
1               5                   10                  15

Leu Asp Ala Ala
            20

<210> SEQ ID NO 91
<211> LENGTH: 20
<212> TYPE: PRT
<213> ORGANISM: Artificial Sequence
<220> FEATURE:
<223> OTHER INFORMATION: HCV634-653

<400> SEQUENCE: 91

Gly Gly Val Glu His Arg Leu Asp Ala Ala Cys Asn Trp Thr Arg Gly
1               5                   10                  15

Glu Arg Cys Asp
            20

<210> SEQ ID NO 92
<211> LENGTH: 20
<212> TYPE: PRT
<213> ORGANISM: Artificial Sequence
<220> FEATURE:
<223> OTHER INFORMATION: HCV644-663

<400> SEQUENCE: 92

Cys Asn Trp Thr Arg Gly Glu Arg Cys Asp Leu Glu Asp Arg Asp Arg
1               5                   10                  15

Ser Glu Leu Ser
            20

<210> SEQ ID NO 93
<211> LENGTH: 20
<212> TYPE: PRT
<213> ORGANISM: Artificial Sequence
<220> FEATURE:
<223> OTHER INFORMATION: HCV654-673

<400> SEQUENCE: 93

Leu Glu Asp Arg Asp Arg Ser Glu Leu Ser Pro Leu Leu Leu Ser Thr
1               5                   10                  15

Thr Glu Trp Gln
            20

<210> SEQ ID NO 94
<211> LENGTH: 20
<212> TYPE: PRT
<213> ORGANISM: Artificial Sequence
<220> FEATURE:
<223> OTHER INFORMATION: HCV664-683

<400> SEQUENCE: 94

Pro Leu Leu Leu Ser Thr Thr Glu Trp Gln Val Leu Pro Cys Ser Phe
1               5                   10                  15

Thr Thr Leu Pro
            20

<210> SEQ ID NO 95
<211> LENGTH: 20
<212> TYPE: PRT
<213> ORGANISM: Artificial Sequence

```
<220> FEATURE:
<223> OTHER INFORMATION: HCV674-693

<400> SEQUENCE: 95

Val Leu Pro Cys Ser Phe Thr Thr Leu Pro Ala Leu Ser Thr Gly Leu
1               5                   10                  15

Ile His Leu His
            20

<210> SEQ ID NO 96
<211> LENGTH: 20
<212> TYPE: PRT
<213> ORGANISM: Artificial Sequence
<220> FEATURE:
<223> OTHER INFORMATION: HCV684-703

<400> SEQUENCE: 96

Ala Leu Ser Thr Gly Leu Ile His Leu His Gln Asn Ile Val His Ala
1               5                   10                  15

Gln His Leu His
            20

<210> SEQ ID NO 97
<211> LENGTH: 20
<212> TYPE: PRT
<213> ORGANISM: Artificial Sequence
<220> FEATURE:
<223> OTHER INFORMATION: HCV694-713

<400> SEQUENCE: 97

Gln Asn Ile Val His Ala Gln His Leu His Gly Val Gly Ser Ala Val
1               5                   10                  15

Val Ser Ile Val
            20

<210> SEQ ID NO 98
<211> LENGTH: 20
<212> TYPE: PRT
<213> ORGANISM: Artificial Sequence
<220> FEATURE:
<223> OTHER INFORMATION: gHCV-1029

<400> SEQUENCE: 98

Ile Thr Ala Tyr Ser Gln Gln Thr Arg Gly Leu Leu Gly Cys Ile Ile
1               5                   10                  15

Thr Ser Leu Thr
            20

<210> SEQ ID NO 99
<211> LENGTH: 20
<212> TYPE: PRT
<213> ORGANISM: Artificial Sequence
<220> FEATURE:
<223> OTHER INFORMATION: gHCV-1039

<400> SEQUENCE: 99

Leu Leu Gly Cys Ile Ile Thr Ser Leu Thr Gly Arg Asp Lys Asn Gln
1               5                   10                  15

Val Glu Gly Glu
            20

<210> SEQ ID NO 100
<211> LENGTH: 19
<212> TYPE: PRT
<213> ORGANISM: Artificial Sequence
```

```
<220> FEATURE:
<223> OTHER INFORMATION: gHCV-1069

<400> SEQUENCE: 100

Phe Leu Ala Thr Cys Val Asn Gly Ala Trp Thr Val Phe His Gly Ala
1               5                   10                  15

Gly Ser Lys

<210> SEQ ID NO 101
<211> LENGTH: 20
<212> TYPE: PRT
<213> ORGANISM: Artificial Sequence
<220> FEATURE:
<223> OTHER INFORMATION: gHCV-1078

<400> SEQUENCE: 101

Trp Thr Val Phe His Gly Ala Gly Ser Lys Thr Leu Ala Gly Pro Lys
1               5                   10                  15

Gly Pro Ile Thr
            20

<210> SEQ ID NO 102
<211> LENGTH: 20
<212> TYPE: PRT
<213> ORGANISM: Artificial Sequence
<220> FEATURE:
<223> OTHER INFORMATION: gHCV-1088

<400> SEQUENCE: 102

Thr Leu Ala Gly Pro Lys Gly Pro Ile Thr Gln Met Tyr Thr Asn Val
1               5                   10                  15

Asp Leu Asp Leu
            20

<210> SEQ ID NO 103
<211> LENGTH: 20
<212> TYPE: PRT
<213> ORGANISM: Artificial Sequence
<220> FEATURE:
<223> OTHER INFORMATION: gHCV-1098

<400> SEQUENCE: 103

Gln Met Tyr Thr Asn Val Asp Leu Asp Leu Val Gly Trp Gln Ala Pro
1               5                   10                  15

Pro Gly Ser Arg
            20

<210> SEQ ID NO 104
<211> LENGTH: 20
<212> TYPE: PRT
<213> ORGANISM: Artificial Sequence
<220> FEATURE:
<223> OTHER INFORMATION: gHCV-1108

<400> SEQUENCE: 104

Val Gly Trp Gln Ala Pro Pro Gly Ser Arg Pro Leu Thr Pro Cys Thr
1               5                   10                  15

Cys Gly Ser Ser
            20

<210> SEQ ID NO 105
<211> LENGTH: 20
<212> TYPE: PRT
<213> ORGANISM: Artificial Sequence
```

```
<220> FEATURE:
<223> OTHER INFORMATION: gHCV-1118

<400> SEQUENCE: 105

Pro Leu Thr Pro Cys Thr Cys Gly Ser Ser Asp Leu Tyr Leu Val Thr
1               5                   10                  15

Arg His Ala Asp
            20

<210> SEQ ID NO 106
<211> LENGTH: 20
<212> TYPE: PRT
<213> ORGANISM: Artificial Sequence
<220> FEATURE:
<223> OTHER INFORMATION: gHCV-1128

<400> SEQUENCE: 106

Asp Leu Tyr Leu Val Thr Arg His Ala Asp Val Ile Pro Val Arg Arg
1               5                   10                  15

Arg Gly Asp Ser
            20

<210> SEQ ID NO 107
<211> LENGTH: 20
<212> TYPE: PRT
<213> ORGANISM: Artificial Sequence
<220> FEATURE:
<223> OTHER INFORMATION: gHCV-1138

<400> SEQUENCE: 107

Val Ile Pro Val Arg Arg Arg Gly Asp Ser Arg Gly Ser Leu Pro Cys
1               5                   10                  15

Pro Arg Pro Val
            20

<210> SEQ ID NO 108
<211> LENGTH: 20
<212> TYPE: PRT
<213> ORGANISM: Artificial Sequence
<220> FEATURE:
<223> OTHER INFORMATION: gHCV-1148

<400> SEQUENCE: 108

Arg Gly Ser Leu Pro Cys Pro Arg Pro Val Ser Tyr Leu Lys Gly Ser
1               5                   10                  15

Ser Gly Gly Pro
            20

<210> SEQ ID NO 109
<211> LENGTH: 20
<212> TYPE: PRT
<213> ORGANISM: Artificial Sequence
<220> FEATURE:
<223> OTHER INFORMATION: gHCV-1158

<400> SEQUENCE: 109

Ser Tyr Leu Lys Gly Ser Ser Gly Gly Pro Leu Leu Cys Pro Ser Gly
1               5                   10                  15

His Ala Val Gly
            20

<210> SEQ ID NO 110
<211> LENGTH: 20
<212> TYPE: PRT
<213> ORGANISM: Artificial Sequence
```

```
<220> FEATURE:
<223> OTHER INFORMATION: gHCV-1168

<400> SEQUENCE: 110

Leu Leu Cys Pro Ser Gly His Ala Val Gly Ile Phe Arg Ala Ala Val
1               5                   10                  15

Cys Thr Arg Gly
            20

<210> SEQ ID NO 111
<211> LENGTH: 20
<212> TYPE: PRT
<213> ORGANISM: Artificial Sequence
<220> FEATURE:
<223> OTHER INFORMATION: gHCV-1178

<400> SEQUENCE: 111

Ile Phe Arg Ala Ala Val Cys Thr Arg Gly Val Ala Lys Ala Val Asp
1               5                   10                  15

Phe Ile Pro Val
            20

<210> SEQ ID NO 112
<211> LENGTH: 20
<212> TYPE: PRT
<213> ORGANISM: Artificial Sequence
<220> FEATURE:
<223> OTHER INFORMATION: gHCV-1188

<400> SEQUENCE: 112

Val Ala Lys Ala Val Asp Phe Ile Pro Val Glu Ser Met Glu Thr Thr
1               5                   10                  15

Met Arg Ser Pro
            20

<210> SEQ ID NO 113
<211> LENGTH: 20
<212> TYPE: PRT
<213> ORGANISM: Artificial Sequence
<220> FEATURE:
<223> OTHER INFORMATION: gHCV-1198

<400> SEQUENCE: 113

Glu Ser Met Glu Thr Thr Met Arg Ser Pro Val Phe Thr Asp Asn Ser
1               5                   10                  15

Thr Pro Pro Ala
            20

<210> SEQ ID NO 114
<211> LENGTH: 20
<212> TYPE: PRT
<213> ORGANISM: Artificial Sequence
<220> FEATURE:
<223> OTHER INFORMATION: HCV1208-1227

<400> SEQUENCE: 114

Val Phe Thr Asp Asn Ser Thr Pro Pro Ala Val Pro Gln Thr Phe Gln
1               5                   10                  15

Val Ala His Leu
            20

<210> SEQ ID NO 115
<211> LENGTH: 20
<212> TYPE: PRT
<213> ORGANISM: Artificial Sequence
```

<220> FEATURE:
<223> OTHER INFORMATION: HCV1218-1237

<400> SEQUENCE: 115

Val Pro Gln Thr Phe Gln Val Ala His Leu His Ala Pro Thr Gly Ser
1               5                   10                  15

Gly Lys Ser Thr
            20

<210> SEQ ID NO 116
<211> LENGTH: 20
<212> TYPE: PRT
<213> ORGANISM: Artificial Sequence
<220> FEATURE:
<223> OTHER INFORMATION: HCV1228-1247

<400> SEQUENCE: 116

His Ala Pro Thr Gly Ser Gly Lys Ser Thr Lys Val Pro Ala Ala Tyr
1               5                   10                  15

Ala Ala Gln Gly
            20

<210> SEQ ID NO 117
<211> LENGTH: 20
<212> TYPE: PRT
<213> ORGANISM: Artificial Sequence
<220> FEATURE:
<223> OTHER INFORMATION: HCV1238-1257

<400> SEQUENCE: 117

Lys Val Pro Ala Ala Tyr Ala Ala Gln Gly Tyr Lys Val Leu Val Leu
1               5                   10                  15

Asn Pro Ser Val
            20

<210> SEQ ID NO 118
<211> LENGTH: 20
<212> TYPE: PRT
<213> ORGANISM: Artificial Sequence
<220> FEATURE:
<223> OTHER INFORMATION: HCV1248-1267

<400> SEQUENCE: 118

Tyr Lys Val Leu Val Leu Asn Pro Ser Val Ala Ala Thr Leu Gly Phe
1               5                   10                  15

Gly Val Tyr Met
            20

<210> SEQ ID NO 119
<211> LENGTH: 20
<212> TYPE: PRT
<213> ORGANISM: Artificial Sequence
<220> FEATURE:
<223> OTHER INFORMATION: HCV1258-1277

<400> SEQUENCE: 119

Ala Ala Thr Leu Gly Phe Gly Val Tyr Met Ser Lys Ala His Gly Ile
1               5                   10                  15

Asp Pro Asn Ile
            20

<210> SEQ ID NO 120
<211> LENGTH: 20
<212> TYPE: PRT
<213> ORGANISM: Artificial Sequence

<220> FEATURE:
<223> OTHER INFORMATION: HCV1268-1287

<400> SEQUENCE: 120

Ser Lys Ala His Gly Ile Asp Pro Asn Ile Arg Thr Gly Val Arg Ala
1               5                   10                  15

Ile Thr Thr Gly
            20

<210> SEQ ID NO 121
<211> LENGTH: 20
<212> TYPE: PRT
<213> ORGANISM: Artificial Sequence
<220> FEATURE:
<223> OTHER INFORMATION: HCV1278-1297

<400> SEQUENCE: 121

Arg Thr Gly Val Arg Ala Ile Thr Thr Gly Ala Pro Ile Thr Tyr Ser
1               5                   10                  15

Thr Tyr Gly Lys
            20

<210> SEQ ID NO 122
<211> LENGTH: 20
<212> TYPE: PRT
<213> ORGANISM: Artificial Sequence
<220> FEATURE:
<223> OTHER INFORMATION: HCV1318-1337

<400> SEQUENCE: 122

His Ser Thr Asp Ser Thr Ser Ile Leu Gly Ile Gly Thr Val Leu Asp
1               5                   10                  15

Gln Ala Glu Thr
            20

<210> SEQ ID NO 123
<211> LENGTH: 20
<212> TYPE: PRT
<213> ORGANISM: Artificial Sequence
<220> FEATURE:
<223> OTHER INFORMATION: HCV1328-1347

<400> SEQUENCE: 123

Ile Gly Thr Val Leu Asp Gln Ala Glu Thr Ala Gly Ala Arg Leu Val
1               5                   10                  15

Val Leu Ala Thr
            20

<210> SEQ ID NO 124
<211> LENGTH: 20
<212> TYPE: PRT
<213> ORGANISM: Artificial Sequence
<220> FEATURE:
<223> OTHER INFORMATION: HCV1348-1367

<400> SEQUENCE: 124

Ala Thr Pro Pro Gly Ser Val Thr Val Pro His Pro Asn Ile Glu Glu
1               5                   10                  15

Val Ala Leu Ser
            20

<210> SEQ ID NO 125
<211> LENGTH: 20
<212> TYPE: PRT
<213> ORGANISM: Artificial Sequence

<220> FEATURE:
<223> OTHER INFORMATION: HCV1358-1377

<400> SEQUENCE: 125

His Pro Asn Ile Glu Glu Val Ala Leu Ser Asn Thr Gly Glu Ile Pro
1               5                   10                  15

Phe Tyr Gly Lys
            20

<210> SEQ ID NO 126
<211> LENGTH: 20
<212> TYPE: PRT
<213> ORGANISM: Artificial Sequence
<220> FEATURE:
<223> OTHER INFORMATION: HCV1368-1387

<400> SEQUENCE: 126

Asn Thr Gly Glu Ile Pro Phe Tyr Gly Lys Ala Ile Pro Ile Glu Val
1               5                   10                  15

Ile Lys Gly Gly
            20

<210> SEQ ID NO 127
<211> LENGTH: 20
<212> TYPE: PRT
<213> ORGANISM: Artificial Sequence
<220> FEATURE:
<223> OTHER INFORMATION: HCV1388-1407

<400> SEQUENCE: 127

Arg His Leu Ile Phe Cys His Ser Lys Lys Lys Ser Asp Glu Leu Ala
1               5                   10                  15

Ala Lys Leu Ser
            20

<210> SEQ ID NO 128
<211> LENGTH: 20
<212> TYPE: PRT
<213> ORGANISM: Artificial Sequence
<220> FEATURE:
<223> OTHER INFORMATION: HCV1398-1417

<400> SEQUENCE: 128

Lys Ser Asp Glu Leu Ala Ala Lys Leu Ser Ala Leu Gly Leu Asn Ala
1               5                   10                  15

Val Ala Tyr Tyr
            20

<210> SEQ ID NO 129
<211> LENGTH: 20
<212> TYPE: PRT
<213> ORGANISM: Artificial Sequence
<220> FEATURE:
<223> OTHER INFORMATION: HCV1408-1427

<400> SEQUENCE: 129

Ala Leu Gly Leu Asn Ala Val Ala Tyr Tyr Arg Gly Leu Asp Val Ser
1               5                   10                  15

Val Ile Pro Thr
            20

<210> SEQ ID NO 130
<211> LENGTH: 20
<212> TYPE: PRT
<213> ORGANISM: Artificial Sequence

```
<220> FEATURE:
<223> OTHER INFORMATION: HCV1418-1437

<400> SEQUENCE: 130

Arg Gly Leu Asp Val Ser Val Ile Pro Thr Ser Gly Asp Val Val
1               5                   10                  15

Val Ala Thr Asp
            20

<210> SEQ ID NO 131
<211> LENGTH: 20
<212> TYPE: PRT
<213> ORGANISM: Artificial Sequence
<220> FEATURE:
<223> OTHER INFORMATION: HCV1458-1477

<400> SEQUENCE: 131

Thr Gln Thr Val Asp Phe Ser Leu Asp Pro Thr Phe Thr Ile Asp Thr
1               5                   10                  15

Thr Thr Val Pro
            20

<210> SEQ ID NO 132
<211> LENGTH: 20
<212> TYPE: PRT
<213> ORGANISM: Artificial Sequence
<220> FEATURE:
<223> OTHER INFORMATION: HCV1468-1487

<400> SEQUENCE: 132

Thr Phe Thr Ile Asp Thr Thr Thr Val Pro Gln Asp Ala Val Ser Arg
1               5                   10                  15

Ser Gln Arg Arg
            20

<210> SEQ ID NO 133
<211> LENGTH: 20
<212> TYPE: PRT
<213> ORGANISM: Artificial Sequence
<220> FEATURE:
<223> OTHER INFORMATION: HCV1478-1497

<400> SEQUENCE: 133

Gln Asp Ala Val Ser Arg Ser Gln Arg Arg Gly Arg Thr Gly Arg Gly
1               5                   10                  15

Arg Arg Gly Ile
            20

<210> SEQ ID NO 134
<211> LENGTH: 20
<212> TYPE: PRT
<213> ORGANISM: Artificial Sequence
<220> FEATURE:
<223> OTHER INFORMATION: HCV1488-1507

<400> SEQUENCE: 134

Gly Arg Thr Gly Arg Gly Arg Arg Gly Ile Tyr Arg Phe Val Thr Pro
1               5                   10                  15

Gly Glu Arg Pro
            20

<210> SEQ ID NO 135
<211> LENGTH: 20
<212> TYPE: PRT
<213> ORGANISM: Artificial Sequence
```

<220> FEATURE:
<223> OTHER INFORMATION: HCV1498-1517

<400> SEQUENCE: 135

Tyr Arg Phe Val Thr Pro Gly Glu Arg Pro Ser Gly Met Phe Asp Ser
1               5                   10                  15

Ser Val Leu Cys
            20

<210> SEQ ID NO 136
<211> LENGTH: 20
<212> TYPE: PRT
<213> ORGANISM: Artificial Sequence
<220> FEATURE:
<223> OTHER INFORMATION: HCV1518-1537

<400> SEQUENCE: 136

Glu Cys Tyr Asp Ala Gly Cys Ala Trp Tyr Glu Leu Thr Pro Ala Glu
1               5                   10                  15

Thr Ser Val Arg
            20

<210> SEQ ID NO 137
<211> LENGTH: 20
<212> TYPE: PRT
<213> ORGANISM: Artificial Sequence
<220> FEATURE:
<223> OTHER INFORMATION: HCV1528-1547

<400> SEQUENCE: 137

Glu Leu Thr Pro Ala Glu Thr Ser Val Arg Leu Arg Ala Tyr Leu Asn
1               5                   10                  15

Thr Pro Gly Leu
            20

<210> SEQ ID NO 138
<211> LENGTH: 20
<212> TYPE: PRT
<213> ORGANISM: Artificial Sequence
<220> FEATURE:
<223> OTHER INFORMATION: HCV1538-1557

<400> SEQUENCE: 138

Leu Arg Ala Tyr Leu Asn Thr Pro Gly Leu Pro Val Cys Gln Asp His
1               5                   10                  15

Leu Glu Phe Trp
            20

<210> SEQ ID NO 139
<211> LENGTH: 20
<212> TYPE: PRT
<213> ORGANISM: Artificial Sequence
<220> FEATURE:
<223> OTHER INFORMATION: HCV1548-1567

<400> SEQUENCE: 139

Pro Val Cys Gln Asp His Leu Glu Phe Trp Glu Ser Val Phe Thr Gly
1               5                   10                  15

Leu Thr His Ile
            20

<210> SEQ ID NO 140
<211> LENGTH: 20
<212> TYPE: PRT
<213> ORGANISM: Artificial Sequence -continued

```
<220> FEATURE:
<223> OTHER INFORMATION: HCV1558-1577

<400> SEQUENCE: 140

Glu Ser Val Phe Thr Gly Leu Thr His Ile Asp Ala His Phe Leu Ser
1               5                   10                  15

Gln Thr Lys Gln
            20

<210> SEQ ID NO 141
<211> LENGTH: 20
<212> TYPE: PRT
<213> ORGANISM: Artificial Sequence
<220> FEATURE:
<223> OTHER INFORMATION: HCV1568-1587

<400> SEQUENCE: 141

Asp Ala His Phe Leu Ser Gln Thr Lys Gln Ala Gly Asp Asn Phe Pro
1               5                   10                  15

Tyr Leu Val Ala
            20

<210> SEQ ID NO 142
<211> LENGTH: 20
<212> TYPE: PRT
<213> ORGANISM: Artificial Sequence
<220> FEATURE:
<223> OTHER INFORMATION: HCV1578-1597

<400> SEQUENCE: 142

Ala Gly Asp Asn Phe Pro Tyr Leu Val Ala Tyr Gln Ala Thr Val Cys
1               5                   10                  15

Ala Arg Ala Gln
            20

<210> SEQ ID NO 143
<211> LENGTH: 20
<212> TYPE: PRT
<213> ORGANISM: Artificial Sequence
<220> FEATURE:
<223> OTHER INFORMATION: HCV1588-1607

<400> SEQUENCE: 143

Tyr Gln Ala Thr Val Cys Ala Arg Ala Gln Ala Pro Pro Pro Ser Trp
1               5                   10                  15

Asp Gln Met Trp
            20

<210> SEQ ID NO 144
<211> LENGTH: 20
<212> TYPE: PRT
<213> ORGANISM: Artificial Sequence
<220> FEATURE:
<223> OTHER INFORMATION: HCV1598-1617

<400> SEQUENCE: 144

Ala Pro Pro Pro Ser Trp Asp Gln Met Trp Lys Cys Leu Thr Arg Leu
1               5                   10                  15

Lys Pro Thr Leu
            20

<210> SEQ ID NO 145
<211> LENGTH: 20
<212> TYPE: PRT
<213> ORGANISM: Artificial Sequence
```

```
<220> FEATURE:
<223> OTHER INFORMATION: HCV1608-1627

<400> SEQUENCE: 145

Lys Cys Leu Thr Arg Leu Lys Pro Thr Leu His Gly Pro Thr Pro Leu
1               5                   10                  15

Leu Tyr Arg Leu
            20

<210> SEQ ID NO 146
<211> LENGTH: 20
<212> TYPE: PRT
<213> ORGANISM: Artificial Sequence
<220> FEATURE:
<223> OTHER INFORMATION: HCV1618-1637

<400> SEQUENCE: 146

His Gly Pro Thr Pro Leu Leu Tyr Arg Leu Gly Ala Val Gln Asn Glu
1               5                   10                  15

Val Thr Leu Thr
            20

<210> SEQ ID NO 147
<211> LENGTH: 20
<212> TYPE: PRT
<213> ORGANISM: Artificial Sequence
<220> FEATURE:
<223> OTHER INFORMATION: HCV1628-1647

<400> SEQUENCE: 147

Gly Ala Val Gln Asn Glu Val Thr Leu Thr His Pro Val Thr Lys Phe
1               5                   10                  15

Ile Met Ala Cys
            20

<210> SEQ ID NO 148
<211> LENGTH: 20
<212> TYPE: PRT
<213> ORGANISM: Artificial Sequence
<220> FEATURE:
<223> OTHER INFORMATION: gHCV-1972

<400> SEQUENCE: 148

Ser Gly Ser Trp Leu Arg Asp Val Trp Asp Trp Ile Cys Thr Val Leu
1               5                   10                  15

Thr Asp Phe Lys
            20

<210> SEQ ID NO 149
<211> LENGTH: 20
<212> TYPE: PRT
<213> ORGANISM: Artificial Sequence
<220> FEATURE:
<223> OTHER INFORMATION: gHCV-1982

<400> SEQUENCE: 149

Trp Ile Cys Thr Val Leu Thr Asp Phe Lys Thr Trp Leu Gln Ser Lys
1               5                   10                  15

Leu Leu Pro Arg
            20

<210> SEQ ID NO 150
<211> LENGTH: 20
<212> TYPE: PRT
<213> ORGANISM: Artificial Sequence
```

```
<220> FEATURE:
<223> OTHER INFORMATION: gHCV-1992

<400> SEQUENCE: 150

Thr Trp Leu Gln Ser Lys Leu Leu Pro Arg Leu Pro Gly Val Pro Phe
1               5                   10                  15

Phe Ser Cys Gln
            20

<210> SEQ ID NO 151
<211> LENGTH: 20
<212> TYPE: PRT
<213> ORGANISM: Artificial Sequence
<220> FEATURE:
<223> OTHER INFORMATION: gHCV-2002

<400> SEQUENCE: 151

Leu Pro Gly Val Pro Phe Phe Ser Cys Gln Arg Gly Tyr Lys Gly Val
1               5                   10                  15

Trp Arg Gly Glu
            20

<210> SEQ ID NO 152
<211> LENGTH: 20
<212> TYPE: PRT
<213> ORGANISM: Artificial Sequence
<220> FEATURE:
<223> OTHER INFORMATION: gHCV-2012

<400> SEQUENCE: 152

Arg Gly Tyr Lys Gly Val Trp Arg Gly Glu Gly Ile Met Gln Thr Thr
1               5                   10                  15

Cys Pro Cys Gly
            20

<210> SEQ ID NO 153
<211> LENGTH: 20
<212> TYPE: PRT
<213> ORGANISM: Artificial Sequence
<220> FEATURE:
<223> OTHER INFORMATION: gHCV-2022

<400> SEQUENCE: 153

Gly Ile Met Gln Thr Thr Cys Pro Cys Gly Ala Gln Ile Ala Gly His
1               5                   10                  15

Val Lys Asn Gly
            20

<210> SEQ ID NO 154
<211> LENGTH: 20
<212> TYPE: PRT
<213> ORGANISM: Artificial Sequence
<220> FEATURE:
<223> OTHER INFORMATION: gHCV-2042

<400> SEQUENCE: 154

Ser Met Arg Ile Val Gly Pro Arg Thr Cys Ser Asn Thr Trp His Gly
1               5                   10                  15

Thr Phe Pro Ile
            20

<210> SEQ ID NO 155
<211> LENGTH: 20
<212> TYPE: PRT
<213> ORGANISM: Artificial Sequence
```

```
<220> FEATURE:
<223> OTHER INFORMATION: gHCV-2052

<400> SEQUENCE: 155

Ser Asn Thr Trp His Gly Thr Phe Pro Ile Asn Ala Tyr Thr Thr Gly
1               5                   10                  15

Pro Cys Ser Pro
            20

<210> SEQ ID NO 156
<211> LENGTH: 20
<212> TYPE: PRT
<213> ORGANISM: Artificial Sequence
<220> FEATURE:
<223> OTHER INFORMATION: gHCV-2062

<400> SEQUENCE: 156

Asn Ala Tyr Thr Thr Gly Pro Cys Ser Pro Ser Pro Ala Pro Asn Tyr
1               5                   10                  15

Ser Arg Ala Leu
            20

<210> SEQ ID NO 157
<211> LENGTH: 20
<212> TYPE: PRT
<213> ORGANISM: Artificial Sequence
<220> FEATURE:
<223> OTHER INFORMATION: gHCV-2072

<400> SEQUENCE: 157

Ser Pro Ala Pro Asn Tyr Ser Arg Ala Leu Trp Arg Val Ala Ala Glu
1               5                   10                  15

Glu Tyr Val Glu
            20

<210> SEQ ID NO 158
<211> LENGTH: 20
<212> TYPE: PRT
<213> ORGANISM: Artificial Sequence
<220> FEATURE:
<223> OTHER INFORMATION: gHCV-2082

<400> SEQUENCE: 158

Trp Arg Val Ala Ala Glu Glu Tyr Val Glu Val Thr Arg Val Gly Asp
1               5                   10                  15

Phe His Tyr Val
            20

<210> SEQ ID NO 159
<211> LENGTH: 20
<212> TYPE: PRT
<213> ORGANISM: Artificial Sequence
<220> FEATURE:
<223> OTHER INFORMATION: gHCV-2092

<400> SEQUENCE: 159

Val Thr Arg Val Gly Asp Phe His Tyr Val Thr Gly Val Thr Thr Asp
1               5                   10                  15

Asn Val Lys Cys
            20

<210> SEQ ID NO 160
<211> LENGTH: 20
<212> TYPE: PRT
<213> ORGANISM: Artificial Sequence
```

-continued

```
<220> FEATURE:
<223> OTHER INFORMATION: gHCV-2102

<400> SEQUENCE: 160

Thr Gly Val Thr Thr Asp Asn Val Lys Cys Pro Cys Gln Val Pro Ala
1               5                   10                  15

Pro Glu Phe Phe
            20

<210> SEQ ID NO 161
<211> LENGTH: 20
<212> TYPE: PRT
<213> ORGANISM: Artificial Sequence
<220> FEATURE:
<223> OTHER INFORMATION: gHCV-2122

<400> SEQUENCE: 161

Thr Glu Leu Asp Gly Val Arg Leu His Arg Tyr Ala Pro Ala Cys Lys
1               5                   10                  15

Pro Leu Leu Arg
            20

<210> SEQ ID NO 162
<211> LENGTH: 20
<212> TYPE: PRT
<213> ORGANISM: Artificial Sequence
<220> FEATURE:
<223> OTHER INFORMATION: gHCV-2132

<400> SEQUENCE: 162

Tyr Ala Pro Ala Cys Lys Pro Leu Leu Arg Asp Glu Val Ser Phe Gln
1               5                   10                  15

Val Gly Leu Asn
            20

<210> SEQ ID NO 163
<211> LENGTH: 20
<212> TYPE: PRT
<213> ORGANISM: Artificial Sequence
<220> FEATURE:
<223> OTHER INFORMATION: gHCV-2152

<400> SEQUENCE: 163

Gln Tyr Leu Val Gly Ser Gln Leu Pro Cys Glu Pro Glu Pro Asp Val
1               5                   10                  15

Ala Val Leu Thr
            20

<210> SEQ ID NO 164
<211> LENGTH: 20
<212> TYPE: PRT
<213> ORGANISM: Artificial Sequence
<220> FEATURE:
<223> OTHER INFORMATION: gHCV-2162

<400> SEQUENCE: 164

Glu Pro Glu Pro Asp Val Ala Val Leu Thr Ser Met Leu Thr Asp Pro
1               5                   10                  15

Ser His Ile Thr
            20

<210> SEQ ID NO 165
<211> LENGTH: 20
<212> TYPE: PRT
<213> ORGANISM: Artificial Sequence
```

```
<220> FEATURE:
<223> OTHER INFORMATION: gHCV-2172

<400> SEQUENCE: 165

Ser Met Leu Thr Asp Pro Ser His Ile Thr Ala Glu Thr Ala Lys Arg
1               5                   10                  15

Arg Leu Ala Arg
            20

<210> SEQ ID NO 166
<211> LENGTH: 20
<212> TYPE: PRT
<213> ORGANISM: Artificial Sequence
<220> FEATURE:
<223> OTHER INFORMATION: gHCV-2182

<400> SEQUENCE: 166

Ala Glu Thr Ala Lys Arg Arg Leu Ala Arg Gly Ser Pro Pro Ser Leu
1               5                   10                  15

Ala Ser Ser Ser
            20

<210> SEQ ID NO 167
<211> LENGTH: 20
<212> TYPE: PRT
<213> ORGANISM: Artificial Sequence
<220> FEATURE:
<223> OTHER INFORMATION: gHCV-2192

<400> SEQUENCE: 167

Gly Ser Pro Pro Ser Leu Ala Ser Ser Ala Ser Gln Leu Ser Ala
1               5                   10                  15

Pro Ser Leu Lys
            20

<210> SEQ ID NO 168
<211> LENGTH: 20
<212> TYPE: PRT
<213> ORGANISM: Artificial Sequence
<220> FEATURE:
<223> OTHER INFORMATION: gHCV-2202

<400> SEQUENCE: 168

Ala Ser Gln Leu Ser Ala Pro Ser Leu Lys Ala Thr Cys Thr Ile His
1               5                   10                  15

His Asp Ser Pro
            20

<210> SEQ ID NO 169
<211> LENGTH: 20
<212> TYPE: PRT
<213> ORGANISM: Artificial Sequence
<220> FEATURE:
<223> OTHER INFORMATION: gHCV-2212

<400> SEQUENCE: 169

Ala Thr Cys Thr Ile His His Asp Ser Pro Asp Ala Asp Leu Ile Glu
1               5                   10                  15

Ala Asn Leu Leu
            20

<210> SEQ ID NO 170
<211> LENGTH: 20
<212> TYPE: PRT
<213> ORGANISM: Artificial Sequence
```

```
<220> FEATURE:
<223> OTHER INFORMATION: gHCV-2222

<400> SEQUENCE: 170

Asp Ala Asp Leu Ile Glu Ala Asn Leu Leu Trp Arg Gln Glu Met Gly
1               5                   10                  15

Gly Asn Ile Thr
            20

<210> SEQ ID NO 171
<211> LENGTH: 20
<212> TYPE: PRT
<213> ORGANISM: Artificial Sequence
<220> FEATURE:
<223> OTHER INFORMATION: gHCV-2232

<400> SEQUENCE: 171

Trp Arg Gln Glu Met Gly Gly Asn Ile Thr Arg Val Glu Ser Glu Asn
1               5                   10                  15

Lys Val Val Ile
            20

<210> SEQ ID NO 172
<211> LENGTH: 20
<212> TYPE: PRT
<213> ORGANISM: Artificial Sequence
<220> FEATURE:
<223> OTHER INFORMATION: gHCV-2242

<400> SEQUENCE: 172

Arg Val Glu Ser Glu Asn Lys Val Val Ile Leu Asp Ser Phe Glu Pro
1               5                   10                  15

Ile Arg Ala Glu
            20

<210> SEQ ID NO 173
<211> LENGTH: 20
<212> TYPE: PRT
<213> ORGANISM: Artificial Sequence
<220> FEATURE:
<223> OTHER INFORMATION: gHCV-2252

<400> SEQUENCE: 173

Leu Asp Ser Phe Glu Pro Ile Arg Ala Glu Glu Asp Glu Arg Glu Val
1               5                   10                  15

Ser Val Pro Ala
            20

<210> SEQ ID NO 174
<211> LENGTH: 20
<212> TYPE: PRT
<213> ORGANISM: Artificial Sequence
<220> FEATURE:
<223> OTHER INFORMATION: gHCV-2262

<400> SEQUENCE: 174

Glu Asp Glu Arg Glu Val Ser Val Pro Ala Glu Ile Leu Arg Arg Ser
1               5                   10                  15

Arg Lys Phe Pro
            20

<210> SEQ ID NO 175
<211> LENGTH: 20
<212> TYPE: PRT
<213> ORGANISM: Artificial Sequence
```

```
<220> FEATURE:
<223> OTHER INFORMATION: gHCV-2272

<400> SEQUENCE: 175

Glu Ile Leu Arg Arg Ser Arg Lys Phe Pro Ala Ala Met Pro Ile Trp
1               5                   10                  15

Ala Arg Pro Asp
            20

<210> SEQ ID NO 176
<211> LENGTH: 20
<212> TYPE: PRT
<213> ORGANISM: Artificial Sequence
<220> FEATURE:
<223> OTHER INFORMATION: gHCV-2292

<400> SEQUENCE: 176

Tyr Asn Pro Pro Leu Leu Glu Ser Trp Lys Asp Pro Asp Tyr Val Pro
1               5                   10                  15

Pro Val Val His
            20

<210> SEQ ID NO 177
<211> LENGTH: 20
<212> TYPE: PRT
<213> ORGANISM: Artificial Sequence
<220> FEATURE:
<223> OTHER INFORMATION: gHCV-2302

<400> SEQUENCE: 177

Asp Pro Asp Tyr Val Pro Pro Val Val His Gly Cys Pro Leu Pro Pro
1               5                   10                  15

Thr Lys Ala Ala
            20

<210> SEQ ID NO 178
<211> LENGTH: 20
<212> TYPE: PRT
<213> ORGANISM: Artificial Sequence
<220> FEATURE:
<223> OTHER INFORMATION: gHCV-2322

<400> SEQUENCE: 178

Pro Ile Pro Pro Pro Arg Arg Lys Arg Thr Ile Val Leu Thr Glu Ser
1               5                   10                  15

Thr Val Ser Ser
            20

<210> SEQ ID NO 179
<211> LENGTH: 20
<212> TYPE: PRT
<213> ORGANISM: Artificial Sequence
<220> FEATURE:
<223> OTHER INFORMATION: gHCV-2332

<400> SEQUENCE: 179

Ile Val Leu Thr Glu Ser Thr Val Ser Ser Ala Leu Ala Glu Leu Ala
1               5                   10                  15

Thr Lys Thr Phe
            20

<210> SEQ ID NO 180
<211> LENGTH: 20
<212> TYPE: PRT
<213> ORGANISM: Artificial Sequence
```

-continued

```
<220> FEATURE:
<223> OTHER INFORMATION: gHCV-2342

<400> SEQUENCE: 180

Ala Leu Ala Glu Leu Ala Thr Lys Thr Phe Gly Gly Ser Gly Ser Trp
1               5                   10                  15

Ala Ala Asp Ser
            20

<210> SEQ ID NO 181
<211> LENGTH: 20
<212> TYPE: PRT
<213> ORGANISM: Artificial Sequence
<220> FEATURE:
<223> OTHER INFORMATION: gHCV-2352

<400> SEQUENCE: 181

Gly Gly Ser Gly Ser Trp Ala Ala Asp Ser Gly Thr Ala Thr Ala Pro
1               5                   10                  15

Pro Asp Gln Thr
            20

<210> SEQ ID NO 182
<211> LENGTH: 20
<212> TYPE: PRT
<213> ORGANISM: Artificial Sequence
<220> FEATURE:
<223> OTHER INFORMATION: gHCV-2372

<400> SEQUENCE: 182

Ser Asp Asp Gly Asp Lys Glu Ser Asp Val Glu Ser Tyr Ser Ser Met
1               5                   10                  15

Pro Pro Leu Glu
            20

<210> SEQ ID NO 183
<211> LENGTH: 20
<212> TYPE: PRT
<213> ORGANISM: Artificial Sequence
<220> FEATURE:
<223> OTHER INFORMATION: gHCV-2382

<400> SEQUENCE: 183

Glu Ser Tyr Ser Ser Met Pro Pro Leu Glu Gly Glu Pro Gly Asp Pro
1               5                   10                  15

Asp Leu Ser Asp
            20

<210> SEQ ID NO 184
<211> LENGTH: 20
<212> TYPE: PRT
<213> ORGANISM: Artificial Sequence
<220> FEATURE:
<223> OTHER INFORMATION: gHCV-2392

<400> SEQUENCE: 184

Gly Glu Pro Gly Asp Pro Asp Leu Ser Asp Gly Ser Trp Ser Thr Val
1               5                   10                  15

Ser Glu Glu Ala
            20
```

VACCINE ENHANCING THE PROTECTIVE IMMUNITY TO HEPATITIS C VIRUS USING PLASMID DNA AND RECOMBINANT ADENOVIRUS

This patent application claims the benefit of priority from Korean Patent Application No. 10-2002-0058712 filed Sep. 27, 2002 and 10-2002-0068496 filed Nov. 6, 2002 both through PCT Application Serial No. PCT/KR2003/001954 filed Sep. 24, 2003, the contents of each of which are incorporated herein by reference.

FIELD OF THE INVENTION

The present invention relates to a DNA vaccine, a recombinant adenovirus vaccine, and a method for administration of those vaccines enhancing the protective immunity to hepatitis C virus, more particularly, a DNA vaccine prepared to induce the optimum cellular immune response through an antigen engineering, a recombinant adenovirus vaccine, and a vaccination method enhancing the protective immunity against HCV infection by regulating the same.

BACKGROUND

HCV (hepatitis C virus) was first found as a major pathogenic microorganism of non-A and non-B (NANB) type hepatitis by Chiron Company in U.S.A. in 1989 (Choo, *Science*, 1989, 244:359-362). The development of HCV diagnostic kit facilitated the research on the actual state of HCV infection. In result, it has been reported that 170 million people have been infected with HCV all over the world, and 1.5% of the Korean population are HCV carriers. Once infected with HCV, 85% of carriers pass into chronic state, which is very high ratio, and chronic HCV leads to hepatocirrhosis and liver cancer (Bisceglie, *Hepatoloty*, 1997, 26: 345), recognizing HCV to be a cause of very threatening disease. However, an effective treatment agent and a vaccine for HCV have not been developed yet.

The states of immunity of both patients recovering from HCV infection and those passing into chronic hepatitis were clinically investigated. While HCV specific cellular immune response was observed in the patients in recovery, the response was not detected in patients switched over chronic hepatitis (Rehermann, *J. Virol.*, 1996, 70:7092; Lechner, *J. Immunol.*, 2000, 30:2479). Especially, CD4+ Th1 immune response has been known to be closely related to the protection and the recovery from HCV infection (Rosen, *Hepatology*, 2002, 35:190; Sarih, *Immunol. lett.*, 2000, 74:117; Diepolder, *J. Mol. Med.*, 1996, 74:538). According to the research by Pape group, the conditions of patients infected with acute hepatitis are classified into three types; 1) strong CD4+ Th1 immune response is observed in the patients group free from the virus, 2) CD4+ T cell immune response is not observed in the patients group switched over chronic hepatitis, and 3) CD4+ T cell immune response is seen at early stage when the virus is in control, but as the immune response weakens, HCV returns (Gerlach, *Gastroenterology*, 1999, 117:933). The above studies support the importance of CD4+ Th1 immune response in the control or elimination of HCV. It was also reported from the studies using a chimpanzee, a unique test animal in which HCV infection and replication are allowed, that rather cellular immunity than humoral immunity played an important role in recovery from HCV infection (Cooper, *Immunity*, 1999, 10:439). Such results suggest that a strong multi-epitope specific Th1 immunity is required for the prevention and the treatment of HCV. Thus, the development of a vaccine for the prevention and the treatment of HCV are now focused on inducing the optimum Th1 cellular immune response.

A subunit protein vaccine was the first HCV preventive vaccine developed by using surface proteins of HCV, envelop 1 and 2 (E1, E2). HCV E1E2 is surface protein of the virus binding to a receptor of a host cell as being infected. If the host cell has a neutralizing antibody against the protein, HCV infection can be prevented. E1E2 subunit vaccine was tried in chimpanzees, precisely, homologous challenge was tried with 10 $CID_{50}$ of infection dose. As a result, HCV infection was successfully prevented in 5 out of 7 chimpanzees, and even after being infected, the rest 2 chimpanzees did not progress to chronic hepatitis (Choo, *Proc. Natl. Acad. Sci. USA*, 1994, 91:1294). That was the first report on HCV preventive vaccine. Even though the effect of the vaccine was proved in chimpanzees, the study has limitations as follows. First, small dose of challenging HCV (10 $CID_{50}$) was inoculated at the peak time of antibody response. Generally, a vaccine has to protect against viral infection by memory response in any circumstances. In the above report, though, antibody response decreased rapidly after the challenging time point. Thus, it is doubtful that the similar protective effect can be achieved when challenge is done after the antibody response decreased. Second, the vaccine was effective against homologous challenge but not heterologous challenge. Considering HCV has at least 6 major genotypes and great numbers of subtypes (Bukh, 1995, *Semin Liver Dis* 15: 41-63), a vaccine must have preventive effect against heterologous challenge at least with in the same genotype. Third, the protective effect of the vaccine depended on not cellular immune response but antibody response. Recently, along with the reports announcing the importance of cellular immunity for the protective immunity to HCV, reports asserting the limitation of antibody response have been made (Cooper, 1999, *Immunity*, 10: 439; Esumi, 2002, *Vaccine*, 20:3095-3103). So, the protein vaccine depending on antibody response alone as a defense mechanism is questionable. Therefore, attempts to induce cellular immunity with DNA vaccine have been made, and as an example, immunity was induced by DNA expressing E2, a surface protein of HCV, resulting in the protective effect against challenge with 100 $CID_{50}$ of homologous monoclonal HCV (Forns X., *Hepatology*, 2000, 32(3): 618-25). It was meaningful as the first report on the preventive vaccine using DNA inducing cellular immunity in chimpanzees, but still had problems, too. First, the challenge was performed at the peak time of immune response. Second, monoclonal HCV challenging inoculum was used for the challenge. Like HCV or HIV (human immunodeficiency virus), the virus that uses error-prone RNA dependent RNA polymerase for replication is characterized by producing numbers of quasispecies. Such variety of quasispecies plays an important role for HCV to establish chronic infection (Farci P, 2000, *Science*, 288:339). According to a recent study, HCV can be produced by intrahepatic injection of HCV RNA into chimpanzee (Kolykhalov, 1997, *Science*, 277: 570-4). The recovered HCV was infectious and used in the study by Forns et al. Since the monoclonal HCV cannot provide a variety of quasispecies which exist in reality, whether the protective effect is still the same when a real infectious HCV attacks is doubtful. Lastly, based on the observation on the immune response and the course of viral infection, it was unclear that the above result was obtained by the immune response induced by the vaccine. That is, immunological evidence which distinguish the case from the natural recovery (about 50%) was not enough to support the protective effect of the vaccine.

A DNA vaccine is superior to a protein vaccine in inducing cellular immune response. Since the antigen of DNA vaccine is expressed in host cells, it can induce humoral immunity with almost native conformation, and even simultaneously induce CD8+ T cell response, a kind of cellular immunity that a protein vaccine cannot induce, so that a DNA vaccine enhances the protective immunity to the maximum and easily induces Th1 immune response simply through the intramuscular injection (Pertmer, *J. Virol.*, 1996, 70:6119). Unlike an inactivated vaccine or a killed vaccine, a DNA vaccine uses only a specific region of the virus as an antigen, causing fewer side effects. In addition, it is easy to store and convey a DNA vaccine, and the purification of the plasmid is also simple, comparing to other vaccines. The safety of a DNA vaccine was approved by Food and Drug Administration (FDA), USA, so that an AIDS DNA vaccine was allowed for clinical study in 1996. After the successful induction of immune response in small animal model, DNA immunization has been tried in many large animal models. Unfortunately, protective immunity against a highly pathogenic virus infection was not secured in large animal models. In experiments with HCV DNA vaccine in chimpanzees, the antibody and cellular immunity induced by DNA vaccine alone were so weak (Forns, *Hepatology*, 2000, 32:618) that another type of vaccine capable of inducing a strong cellular immunity was required.

Even though the limitation of a DNA vaccine has been widely known, the merit of the vaccine that can prime delicate immune response and Th1 immunity encouraged the study to overcome the limitation by combining with other boosting method. Previous reports suggest that the effect of the vaccine is greatly enhanced when boosted with a recombinant protein or an attenuated recombinant virus after priming with DNA. Such attempts were successful in small animals by inducing protective immunity against challenges (Song, *J. Virol.*, 2000, 74:2920; Hanke, 1998, *Vaccine*, 16: 439-45; Sedegah, 1998, *Proc. Natl. Acad. Sci. USA*, 95: 7648-53; Schneider, 1998, *Nat Med*, 4: 397-402), and so was in Primates (Kent, 1998, *J Virol*, 72: 10180-8; Robinson, 1999, *Nat Med*, 5: 526-34; Amara, 2001, *Science*, 292: 69-74). Yet, there has been no report on the protective effect of DNA prime and adenovirus boosting regimen against hepatitis C virus infection.

Adenovirus has been proved safe and widely used as a vector for gene therapy. It was also proved to be very useful as a vaccine since it could induce strong humoral, cellular immune responses in various animal models (Natuk, *Proc. Natl. Acad. Sci. USA*, 1992, 89(16): 7777; Bruce, *J. Gen. Virol.*, 1999, 80:2621). An earlier report demonstrated that the induced immune response was maintained for a long time after single injection of a replication-defective adenovirus (Juillard, *Eur. J. Immunol.*, 1995, 25:3467). The antibody response and cellular immune response were also induced in small animal models by immunization with recombinant adenovirus expressing HCV structural gene (Makimura, *Vaccine*, 1996, 14:28; Bruna-Romero, *Hepatology*, 1997, 25:470; Seong, *Vaccine*, 2001, 19:2955). However, the induced Th1 immunity including CTL response was not compared in parallel with a DNA vaccine. Under this circumstance, DNA priming and adenovirus boosting regimen was tested in monkey model and proved its potential as a next generation vaccine regimen (Sullivan, 2000, *Nature*, 408: 605-9; Shiver, 2002, *Nature*, 415: 331-5).

The present inventors developed a DNA vaccine which induces optimal level of cellular immune response to hepatitis C virus through antigen engineering and confirmed that optimal Th1 immune response was induced by DNA priming and adenovirus boosting regimen. Finally, the present inventors proved in chimpanzee study that the vaccine regimen of the invention could induce the protective immunity against hepatitis C virus infection.

DETAILED DESCRIPTION OF PREFERRED EMBODIMENTS

In order to achieve an object of the present invention, this invention provides a DNA vaccine including plasmid containing 2-6 kb, more preferable, 2-4 kb of the total antigen gene of hepatitis C virus, more precisely, provides a DNA vaccine including the $1^{st}$ plasmid containing core, E1 and E2 genes, the $2^{nd}$ plasmid containing NS3 and NS4 genes, and the $3^{rd}$ plasmid containing NS5 gene.

The present invention also provides a DNA vaccine characterized by having the $1^{st}$ plasmid containing core, in which 35-40 amino acids of amino-terminal region are eliminated, and a DNA vaccine characterized by having transmembrane domain of E2 in the $1^{st}$ plasmid above.

The present invention further provides a DNA vaccine in which the $1^{st}$ plasmid has a base sequence represented by SEQ. ID. No 50, particularly, a DNA vaccine whose $1^{st}$ plasmid is pGX10 gDsΔ ST (Accession No: KCCM 10415); a DNA vaccine in which the $2^{nd}$ plasmid includes a base sequence represented by SEQ. ID. No 51, particularly, a DNA vaccine whose $2^{nd}$ plasmid is pGX10 NS34 (Accession No: KCCM 10417); a DNA vaccine in which the $3^{rd}$ plasmid contains a base sequence represented by SEQ. ID. No 52, particularly, a DNA vaccine whose $3^{rd}$ plasmid is pGX10 NS5 (Accession No: KCCM 10416).

The present invention also provides a DNA vaccine in which the $1^{st}$ plasmid includes a base sequence represented by SEQ. ID. No 50, the $2^{nd}$ plasmid has a base sequence represented by SEQ. ID. No 51, and the $3^{rd}$ plasmid contains a base sequence represented by SEQ. ID. No 52; more precisely, a DNA vaccine characterized by that the $1^{st}$ plasmid is pGX10 gDsΔ ST (Accession No: KCCM 10415), the $2^{nd}$ plasmid is pGX10 NS34 (Accession No: KCCM 10417), and the $3^{rd}$ plasmid is pGX10 NS5 (Accession No: KCCM 10416), and a DNA vaccine further supplemented with pGX10 hIL-12m.

In order to achieve another object of the invention, the present invention provides a recombinant adenovirus vaccine including adenovirus containing 2-6 kb, preferably 2-4 kb, of total antigen gene of hepatitis C virus, more precisely, a recombinant adenovirus vaccine characterized by having all of the $1^{st}$ adenovirus containing core, E1 and E2 genes, the $2^{nd}$ adenovirus containing NS3 gene and NS4 gene, and the $3^{rd}$ adenovirus containing NS5 gene.

The present invention also provides a recombinant adenovirus vaccine in which 35-40 amino acids of amino-terminal region of core are eliminated in the $1^{st}$ adenovirus, and a recombinant adenovirus vaccine containing transmembrane domain of E2 in the $1^{st}$ adenovirus above.

The present invention further provides a recombinant adenovirus vaccine whose $1^{st}$ adenovirus has a base sequence represented by SEQ. ID. No 50, precisely, the $1^{st}$ adenovirus is rAd gDsΔ ST (Accession No: KCCM 10418); a recombinant adenovirus vaccine whose $2^{nd}$ adenovirus has a base sequence represented by SEQ. ID. No 54, precisely, the $2^{nd}$ adenovirus is rAd gDs NS34 (Accession No: KCCM 10420); and a recombinant adenovirus vaccine whose $3^{rd}$ adenovirus has a base sequence represented by SEQ. ID. No 52, precisely, the $3^{rd}$ adenovirus is rAd NS5 (Accession No: KCCM 10419).

The present invention also provides a recombinant adenovirus vaccine composed of the $1^{st}$ adenovirus having a base sequence represented by SEQ. ID. No 50, the $2^{nd}$ adenovirus having a base sequence represented by SEQ. ID. No 54, and the 3$^{rd}$ adenovirus having a base sequence represented by SEQ. ID. No 52; more particularly, a recombinant adenovirus vaccine in which the 1$^{st}$ adenovirus is rAd gDsΔ ST (Accession No: KCCM 10418), the 2$^{nd}$ adenovirus is rAd gDs NS34 (Accession No: KCCM 10420) and the 3$^{rd}$ adenovirus is rAd-NS5 (Accession No: KCCM 10419).

In order to achieve other object of the invention, the present invention provides a vaccine administrating method characterized by enhancing the protective immunity to HCV by boosting with the above adenovirus vaccine after priming with the DNA vaccine 2-5 times.

The present invention also provides a method to enhance the protective immunity to HCV by increasing CD4+ Th1 immune response by boosting with a recombinant adenovirus vaccine after priming with a DNA vaccine.

The present invention further provides a method for the prevention and the treatment of hepatitis C, which is characterized by boosting with a recombinant adenovirus vaccine after priming with a DNA vaccine.

The term "DNA vaccine" herein means a plasmid containing a gene coding a protein that works as an antigen or a substance containing the said plasmid and pharmaceutical components that are generally added for the vaccine preparation.

The term "priming" means primary antigen-stimulation (sensitization), and the term "boosting" means additional immunity after primary antigen-stimulation.

Hereinafter, the present invention is described in detail.

The whole gene sequence of HCV is divided into a structural protein region (Core-E1-E2) gene and two other non-structural protein region (NS3-NS4 and NS5) genes, and the present invention provides individual plasmids (or recombinant adenoviruses) containing each of the above genes.

RNA virus such as HCV or HIV escapes from host immune surveillance by generating diverse quasispecies since the acute phase of infection (Shimizu Y K et al, 1994, *J Virol,* 68:1494-500; Weiner A et al, 1995, *Proc. Natl. Acad. Sci. USA,* 92:2755; Wyatt C A et al, 1998, *J Virol,* 72:1725; Erickson A L et al, 2001, *Immunity,* 15:883), which was known as a major mechanism for the virus to persist (Farci P et al, 2000, *Science,* 288:339). In order to protect against the virus infection, multi-epitope specific cellular immunity has to be induced simultaneously (Cooper, 1999, *Immunity,* 10:439; Lechmann, 2000, *Semin Liver Dis* 20(2): 211), which required the vaccine to include as long part of viral gene as possible. For this, it is necessary to optimize insert length in a DNA vaccine (or in a recombinant adenovirus vaccine).

For example, when ten kinds of HCV proteins are individually expressed by separate plasmids (or adenoviruses), a vector backbone takes huge part in DNA vaccine, comparing to the length of a gene taken by an antigen. Therefore, large amount of DNA is required for sufficient level of expression of the antigen. Inefficiency is another problem in the production of a vaccine or the experiments of toxicity aiming at clinical researches. On the contrary, if a whole HCV gene is expressed in a plasmid (or adenovirus), the expression during transcription and translation becomes inefficient, which not only is inadequate to induce an effective cellular immunity but also affects the stability of DNA during the production and purification processes. In order to overcome the potential problems, which range of insert length in a DNA vaccine can efficiently induce cellular immunity should be scrutinized. The strategy is to find out a DNA vaccine with proper insert length that possesses as large part of a gene as possible and induces as strong cellular immunity as well as a DNA vaccine that expresses whole HCV gene. As a result, a plasmid (or adenovirus) including 2-6 kb of total HCV gene was proved to be very effective, and preferably, a plasmid (or adenovirus) including 2-4 kb, more preferably, a vaccine including three individual plasmids (or adenoviruses) containing one structural protein domain (Core-E1-E2) and two non-structural protein domains (NS3-NS4 and NS5), respectively, was developed. As of today, at least six major genotypes of HCV including HCV-1, HCV-J, etc., have been reported. Structural region of HCV composed of core, E1 and E2, and non-structural region composed of NS2, NS3, NS4 and NS5. 2-6 kb size HCV gene included in the plasmid (or adenovirus) of the invention is not limited in the genotypes.

The present invention also provides a plasmid (or recombinant adenovirus) in which 35-40 amino acids of amino-terminal region of core are eliminated, and genes E1 and E2 are included. At this time, the number of amino acids for the elimination is preferably 40, and E2 preferably keeps transmembrane domain.

Core of HCV is the region that has the highest homology with many other types, making it the best target for the development of a vaccine against heterologous infection (Shirai M. 1994, *J Virol,* 68:3334-42; Inchauspe G., 1995, *J Virol,* 69:5798-5805; Wands J R, 1996, *Hepatology,* 24:14-20; Geissler M., 1997, *J Immunol,* 158:1231-7; Arichi T, 2000, *Proc. Natl. Acad. Sci. USA,* 97:297-302; Polakos N K., 2001, *J Immunol,* 166(5):3589-3598). However, it was reported that HCV core has immunosuppressive function (Large, 1999 *J Immunol* 162:931-8, Lee, *Virology,* 2001, 279:271). Thus, the present inventors developed a vaccine without core's immunosuppressive function by removing 35-40 amino acids of amino-terminal region of core, and especially, the elimination of 40 amino acids was confirmed to be more effective.

In the case of using the envelope protein of HCV as a vaccine, a DNA without transmembrane domain of E2 was used to induce extracellular secretion for the induction of antibody response. Yet, considering the report that the antibody response might not provide the protective immunity against HCV infection (Cooper, 1999, *Immunity,* 10:439: Esumi, 2002, *Vaccine,* 20: 3095-3103), the present inventors developed the said DNA vaccine (or recombinant adenovirus vaccine) keeping transmembrane domain of E2 based on the result that the DNA can induce cellular immunity better than the DNA without transmembrane domain.

The present inventors developed plasmids pGX10 gDsΔ ST (Accession No: KCCM 10415), pGX10 NS34 (Accession No: KCCM 10417) and pGx10 NS5 (Accession No: KCCM 10416), and named the mixture DNA vaccine HC102 (FIG. 2). pGX10 gDsΔ ST includes core gene coding core protein of HCV, and E1 and E2, both encoding envelope protein, pGX10 NS34 includes genes corresponding to non-structural proteins 3 and 4 (NS34), and pGX10 NS5 includes a gene corresponding to structural protein 5 (NS5). IL-12 mutant DNA (pGX10 mIL-12m) (Ha, 2002, *Nat Biotechnol,* 20: 381-6), which is known to enhance the immunogenicity of HCV DNA vaccine in small animal model, could be further included in HC102, and the DNA vaccine containing pGX10 hIL-12m was named HC103 (FIG. 3).

The present inventors developed a DNA vaccine vector included in AIDS DNA vaccine, which was named pGX10. As shown in FIG. 2, the vector pGX10 of the present invention consists of simian virus 40 origin (SV40 ori), cytomegalovirus (CMV) promoter/enhancer sequence, adenovirus tripartite leader sequence (TPL), multi-cloning site (MCS), simian virus 40 polyA sequence (SV40PA), simian virus 40 enhancer sequence (SV40Eh), and additionally ColE1 Ori and kanamycin-resistant gene (KanR) which enable a plasmid to proliferate in *E. coli.* It is a novel vector in 3.6 kb size including several specific restriction regions. The vector pGX10 was prepared based on pTX (Lee, *Vaccine* 17:473-9, (1999)) that was reported previously by the present inventors. Precisely, vector pTV2, already used as a DNA vaccine vector in the studies in small animals (Lee, *J Virol.* 72,8430 (1998); Cho, *Vaccine* 17,1136 (1999)), was used as a starting vector and the preparation process was as informed. The resultant novel vector developed by the present inventors was deposited at KCTC (Accession No: 10212BP). By the way, the promoter types and the sorts and sizes of glycoprotein signal sequences can be changed depending on the object of the examples of the invention. For example, RSV promoter, a viral promoter, and EF1, MCK (muscle specific promoter) and LCK (T cell specific promoter), cellular promoters, can be selected according to circumstances, and glycoprotein can also be substituted with VZV (varicella zoster virus) gB, HCMV (human cytomegalovirus) gH, gL, gO, VSV (vesicular stomatitis virus) G protein, rotavirus outer capsid glycoprotein, and VP7.

In order to prevent the degradation of DNA and to promote transduction into cells, the plasmid of the invention preferably forms a complex with cationic lipid like DMRIE/DOPE. The plasmid DNA can be regarded as a drug substance and can be produced in a well-characterized *E. coli* host. Once enters into cells, a recombinant gene of the plasmid is expressed, resulting in the production of a gene product having a biochemical activity. For the production of a drug substance, the plasmid DNA is mixed with lipids DMRIE and DOPE in an injection vehicle. DMRIE/DOPE lipid complex has a positive electric charge overall, so that it can combine with DNA having a negative electric charge. The resultant plasmid DNA-lipid complex is directly injected into an object.

It is a common knowledge for the people in this field that the said plasmid of the present invention is presented as a preferable example, having no intention to limit the present invention therein. And thus, every expression vector that is suitable for the conveyance of the subjects and the acquisition of the production, and has all the merits mentioned above can be included in the category of the present invention.

The present invention further provides individual recombinant adenoviruses each including structural genes of HCV, core, E1 and E2, non-structural genes, NS3 and NS4, and another non-structural gene, NS5, respectively (FIG. 4). At this time, the recombinant adenovirus includes the same HCV gene structure and territory as the above plasmid expressing HCV gene.

The recombinant adenovirus of the present invention is characterized by having the said HCV genes in addition to the basic structure of the general adenovirus. In order to prepare HCV adenovirus vaccine, the present inventors developed a recombinant adenovirus by inserting HCV antigen genes 'gDsΔ ST', 'gDsNS34' and 'NS5' in a replication defective adenovirus vector without E1 gene essential for the virus replication, and each was named 'rAd gDsΔ ST' (Accession No: KCCM 10418), 'rAd gDsNS34' (Accession No: KCCM 10420) and 'rAd NS5' (Accession No: KCCM 10419), and the vaccine including all of them was named rAd-HC102.

The "immunologically effective" dosage of the vaccine compound used in this invention means the amount of single or multiple administrations that is effective for the prevention or the treatment. The specific dosage depends on health and body condition of an individual, classified groups (for example: human, nonhuman primates, primates, etc.), the condition of immune system, the formulations of vaccine, the decision of a doctor in charge, the pathway of HCV infection and other relating factors. The dosage can be decided by general trial, comparatively having a wide range. Generally, the dosage of the vaccine of the invention ranges from 1 μg to 20 mg per administration. The regulation of dosage according to the mentioned method or other standard way for the maximum effect is also regarded as natural to the people in this field.

The vaccine can be given by single or preferably multi-administration. DNA priming-rAd boosting immunization is preferably used for the multi-administration of a DNA vaccine and a recombinant adenovirus vaccine.

The vaccine is optionally compounded of vegetable oil or its emulsion; surfactant such as hexadecylamine, octadecyl amino acid ester, octadecylamine, lysolecithin, dimethyl-dioctadecylamonium bromide, N,N-dioctadecyl-N'—N'-bis (2-hydroxyethyl-propanediamine), methoxyhexadecylglycerol and fluoric polyol; polyamine such as pyran, dextransulfate, poly IC and carbopol; peptide such as muramyl dipeptide, dimethylglycine and turpethsin; immunostimulating complex; oil emulsion; lipopolysaccharide such as MPLR (3-O-deacylated monophosphoryl lipid A; RIBI ImmunoChem Research, Inc., Hamilton, Mont.) and mineral gel. The plasmid DNA or the recombinant adenovirus of the present invention can be further supplemented with liposome, cochleates, biodegradable polymer such as poly-lactide, poly-glycolide and poly-lactide-co-glycolide, or ISCOMS (immunostimulating complex), and with additional activating factors, as well. The plasmid of the present invention can be administered along with bacterial toxin and its attenuated derivatives.

The vaccine can be administered to human or animals through various routes including parenteral, intra-arterial, intracutaneous, transdermal, intramuscular, intraperitoneal, intravenous, subcutaneous, oral and intranasal administration (not always limited thereto). The dosage of an antigen used for the vaccine varies upon the homogeneity of the antigen. It depends on the decision made by the people in this field to regulate and manipulate the set amount of the vaccine used together with a general carrier antigen for the vaccine of the present invention.

The present invention also provides a method for the administration of a vaccine characterized by enhancing the protective immunity to HCV by boosting with a recombinant adenovirus vaccine after priming with a DNA vaccine.

In order to enhance the protective immunity, there are four possible ways: only a DNA vaccine is injected to an object, only a recombinant adenovirus vaccine is injected, priming with a DNA vaccine is followed by boosting with a recombinant adenovirus vaccine, or priming with a recombinant adenovirus vaccine is followed by boosting with a DNA vaccine. However, in order to get the optimum effect of the immunity to HCV, boosting with a recombinant adenovirus vaccine after priming with a DNA vaccine is preferred. The priming frequency is preferably 2-5 times, and particularly, three times of DNA priming and the following one performance of adenovirus boosting was proved to be more effective in earlier experiments with chimpanzees.

Precisely, in order to get the optimum protective immunity to HCV, three times of priming with the DNA vaccine containing all of pGX10 gDsΔ ST (Accession No: KCCM 10415), pGX10 NS34 (Accession No: KCCM 10417), and pGX10 NS5 (Accession No: KCCM 10416), or the DNA vaccine supplemented with pGX10 hIL-12m to the above ought to be preceded by the one time boosting with the recombinant adenovirus vaccine containing all of rAd gDsΔ ST (Accession No: KCCM 10418), rAd gDs NS34 (Accession No: KCCM 10420), and rAd NS5 (Accession No: KCCM 10419).

The present invention further provides a method for the prevention or the treatment of hepatitis C by administrating a DNA vaccine and/or a recombinant adenovirus vaccine.

The method for the prevention or the treatment of hepatitis C with a DNA vaccine and/or a recombinant adenovirus vaccine preferably uses DNA-priming-rAd boosting method, which is effective in inducing both CD4+ Th1 immune response and cytotoxic T lymphocyte response. Especially, DNA priming-rAd-boosting method is particularly effective in inducing CD4+ Th1 immune response that has been known to play an important role in eliminating HCV and recovery from illness. Thus, the said method can be effectively used for the prevention and the treatment of HCV.

In order to confirm the antigen expression by the HCV DNA vaccine and the recombinant adenovirus vaccine prepared in this invention, COS-7 animal cells (ATCC CRL-1651) were transfected with vectors pGX10 gDsΔ ST, pGX10 NS34 and pGX10 NS5, in addition to a control vector pGX10. The transfected cells were harvested to confirm the expression of core, E2, NS3, NS4, and NS5 by Western blot analysis using antigen-specific antibodies. COS-7 cells were also transfected with rAd gDsΔ ST, rAd gDsNS34, and rAd NS5, in addition to the control virus rAd-mock produced and purified by using 293A cells. Then, the transfected cells were harvested to confirm the expression of the mentioned antigens by Western blot analysis also using the said antibodies.

As a result, unlike in the control vector pGX10 and control virus rAd-mock infected cells, HCV core, E2, NS3, NS4 and NS5 proteins were expressed in animal cells cultured after the injection with pGX10 gDsΔ ST, pGX10 NS34 and pGX10 NS5 or rAd gDsΔ ST, rAd gDsNS34 and rAd NS5. So, the plasmid and the recombinant adenovirus of the present invention were confirmed to express HCV proteins (FIG. 5-FIG. 8).

The present inventors performed experiments with animal samples using pGX10 gDsΔ ST and pGX10 mIL-12 mutant as DNA vaccines and using rAd gDsΔ ST as a recombinant adenovirus vaccine. In order to investigate what vaccine can best induce CD4+ Th1 immune response which has been known to be most important for the elimination of HCV and the recovery from illness, CD4+ T cells were selected and used for IFN-γ and IL-4 ELISPOT (Enzyme-linked immunospot) assays. Cytokine IFN-γ is the representative Th1 cytokine that is secreted in activated T-cells. On the contrary, cytokine IL-4 is the representative Th2 cytokine that induces B-cell differentiation and Th2 immune response. ELISPOT was performed to quantify the cells secreting those cytokines. As a result, DNA priming-rAd boosting method with HCV E2 and core protein antigens was proved to make CD4+ T cells produce IFN-γ most, comparing to other methods (G2 in FIG. 13A and FIG. 13B, p<0.001). While CD4+ T cells producing E2 specific IFN-γ were hardly generated when just a DNA vaccine was treated twice (FIG. 13A, G1), CD4+ T cells producing core protein specific IFN-γ were generated as much as the group treated with rAd twice (FIG. 13B, G1). That was because core protein antigen itself, unlike E2, could effectively induce CD4+ T cell immune response with the treatment of a DNA vaccine alone. By contrast, there was barely detectable core- or E2-specific IL-4 ELISPOT response in all groups (FIG. 13C and FIG. 13D), supporting the idea that a DNA vaccine and an adenovirus vaccine could induce Th1 CD4+ T cell immune response rather than Th2 immune response. Taken together, the present inventors confirmed that the method of the invention, in which the immunization of a DNA vaccine followed by recombinant adenovirus boosting, induced better CD4+ Th1 immune response than the immunization with an adenovirus twice or adenovirus followed by the boosting with a DNA vaccine.

HCV E2-specific $^{51}$Cr release assay was also performed to investigate cytotoxic T lymphocyte response, in which adenovirus twice and DNA priming-rAd boosting method were both confirmed to be very efficient, without a significant difference between the two regimens (see FIG. 14, G2 and G3). Even though rAd priming-DNA boosting method and the twice injection of DNA showed antigen-specific cytotoxic T lymphocyte response, those were not so much effective as the above two methods (see FIG. 14, G1 and G4). So, the DNA priming-rAd boosting method was confirmed to be the most effective way to induce cytotoxic T lymphocyte response.

The present inventors proved the effect of the vaccines of the invention by investigating whether the vaccines could inhibit the replication of the infectious HCV in chimpanzees, the only reliable animal susceptible to HCV infection, after inducing protective immunity.

Precisely, the level of cellular immunity induced in chimpanzees by using a DNA vaccine and a recombinant adenovirus vaccine was investigated. And also, after challenging with the infectious hepatitis C virus, how the vaccine-induced immunity could effectively prevent the replication of hepatitis C virus was examined.

The present inventors attempted to enhance cellular immunity by boosting with a recombinant adenovirus after priming with HCV three times. At that time, hIL-12 mutant proved to promote memory immune response of cellular immunity was simultaneously injected for comparison. HC102, a mixture DNA vaccine consisted of pGX10 gDsΔ ST, pGX10 NS34 and pGX10 NS5, was administered to the experimental group 1, and HC103 prepared by adding pGX10 hIL-12m DNA to HC102 was administered to the experimental group 2. After injecting a DNA vaccine three times, boosting with the recombinant adenovirus 'rAd-HC102' expressing the same region of HCV as HC102 was performed on the 30$^{th}$ week after last DNA injection, and cellular immunity was investigated after two weeks from then. Cellular immunity was analyzed by IFN-γ ELISPOT, which has been known as the most sensitive method for cellular immunity. As a result, 4 out of 6 chimpanzees administered with the vaccine showed very strong immune response but the remaining 2 chimpanzees showed marginal response (see FIG. 16). No difference was observed between the experimental group 1 and group 2. One of the control group chimpanzees (#404) treated with nothing, though, showed relatively strong IFN-γ ELISPOT response. That meant the chimpanzee was exposed with HCV, supported by the unpublished report from New York Blood Center. In order to be selected for control group, a chimpanzee should be free from previous history of viremia and HCV-specific antibody response. All the chimpanzees here in the control group met the standard, but if they had been exposed to subinfectious dose of HCV, cellular immunity could be induced without viremia (Shata M T, *Virology* 2003, 314:601-16).

While FIG. 16 represents combined activity of and CD8+ T cells, FIG. 17 and FIG. 18 show the activity of CD4+ T cells only. As an index of Th1 immune response, the amount of IFN-γ secreted by CD4+ T cells was measured. As a result, comparatively large amount of IFN-γ was detected in the experimental group 1. In the experimental group 2, small amount of IFN-γ was detected, which was, though, higher than that of the control group. Another CD4+ T cell response, T cell proliferate response, was examined as well. As a result, the level of the response was higher in the experimental group 1 than in the group 2, and was barely detectable in the control group. At that time, one of the control group chimpanzees (#406) showed the similar proliferate response to the vaccine-injected chimpanzees, suggesting its previous exposure of subinfectious dose of HCV.

In order to investigate the effect of cellular immune response on the control of the viral replication, challenge with 100 $CID_{50}$ infectious HCV-bk, different from the vaccine strain, was performed. The challenge condition was set to evaluate the vaccine regimen according to the following issues. First, it had to be confirmed that the cellular immune response induced by the vaccine regimen of the present invention could exert long-term protective effect. Even after the vaccination, the moment of the virus infection is unknown. So, to be an effective vaccine, it should keep its protective immunity for a long while after the vaccination. While the challenges have been generally done on the $2^{nd}$-$3^{rd}$ week after the last vaccination in previous reports (Choo, *Proc. Natl. Acad. Sci. USA,* 1994, 91:1294; Forns X., *Hepatology,* 2000, 32(3): 618-25), it was performed on the $12^{th}$ week in this invention, at which the immunity usually decline, to investigate whether the lowered immune response could prevent the HCV infection. Second, it ought to be confirmed that the cellular immunity induced by the regimen of the present invention could protect against high dose of HCV infection, for which not only a vigorouos cellular immunity should be induced but also surveillance over diverse quasispecies should be established, since the diversity of quasispecies would increase as dose of challenging inoculum increases (Wyatt C A 1998 *J Virol* 72:1725). For that purpose, the dose of the challenging virus was adjusted to 100 $CID_{50}$. Lastly, it had to be confirmed that the cellular immunity induced by the method of the present invention could provide cross protection against different strain of HCV within the same genotype. While 5-6 logs of viral load was observed in the control group on the $2^{nd}$ week after the infection, the virus was hardly detectable in 5 out of 6 vaccinated chimpanzees. The viral loads in two chimpanzees (#400, # 381) were borderline positive, which were determined as negative in repeated experiments for the confirmation, suggesting that the viral loads were slightly below the detection or, if above, very low level compared with the control group. According to the report on 38 chimpanzees challenged with HCV, the peak viral load was $10^{5.74}$-$10^{5.82}$ (Prince A M, 2002, *9th International Meeting on HCV and Related Viruses*, P-259). Comparing the value with the conventional statistics or that of the control group of the present invention, the protective immunity induced by the present invention was proved to be protective against acute phase of HCV infection in chimpanzees.

BRIEF DESCRIPTION OF THE DRAWINGS

The application of the preferred embodiments of the present invention is best understood with reference to the accompanying drawings, wherein.

■: G3, ▲: G4

Figure 15:
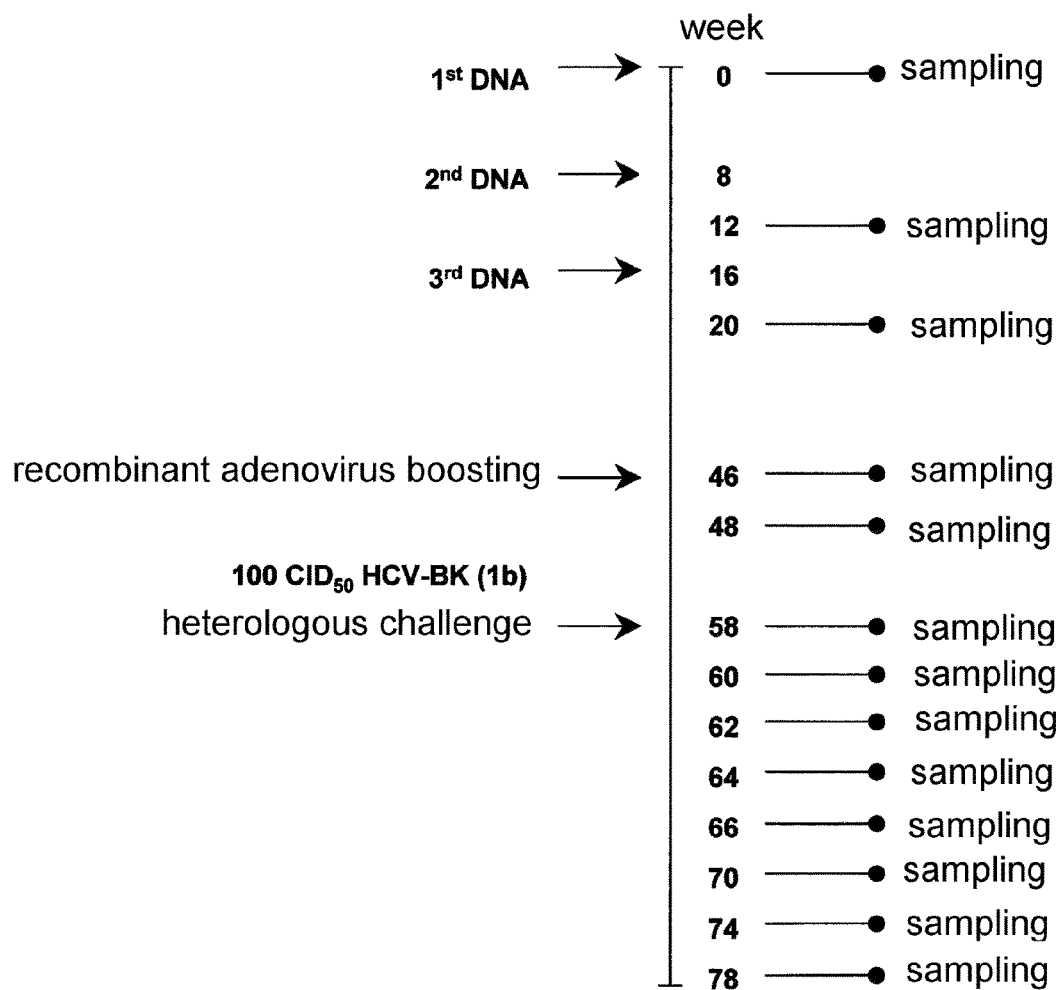
Figure 16:
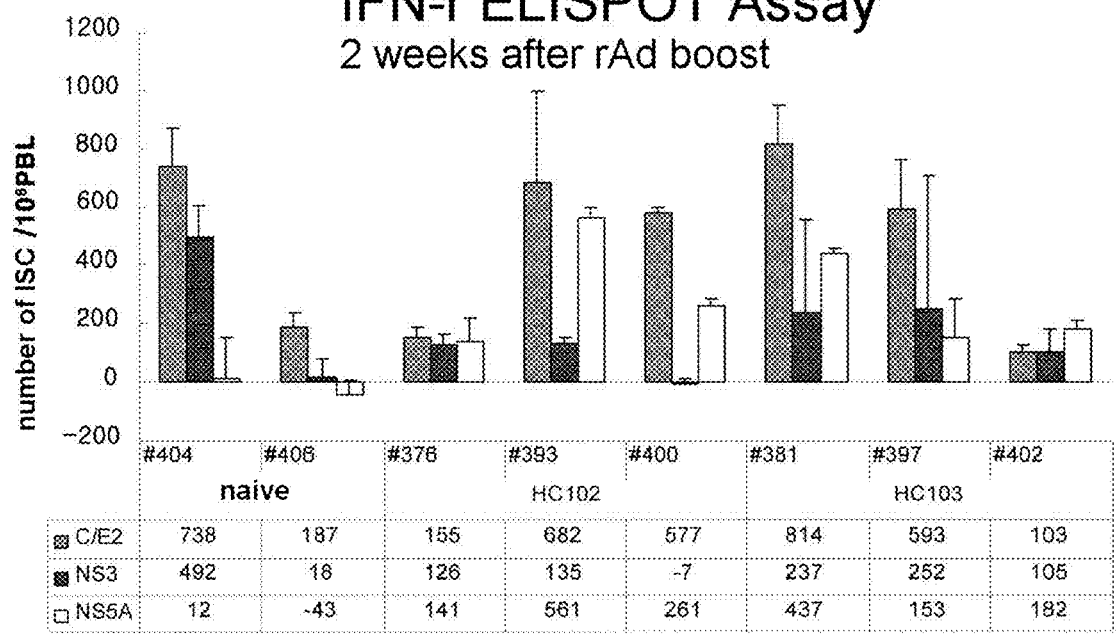
Figure 17:
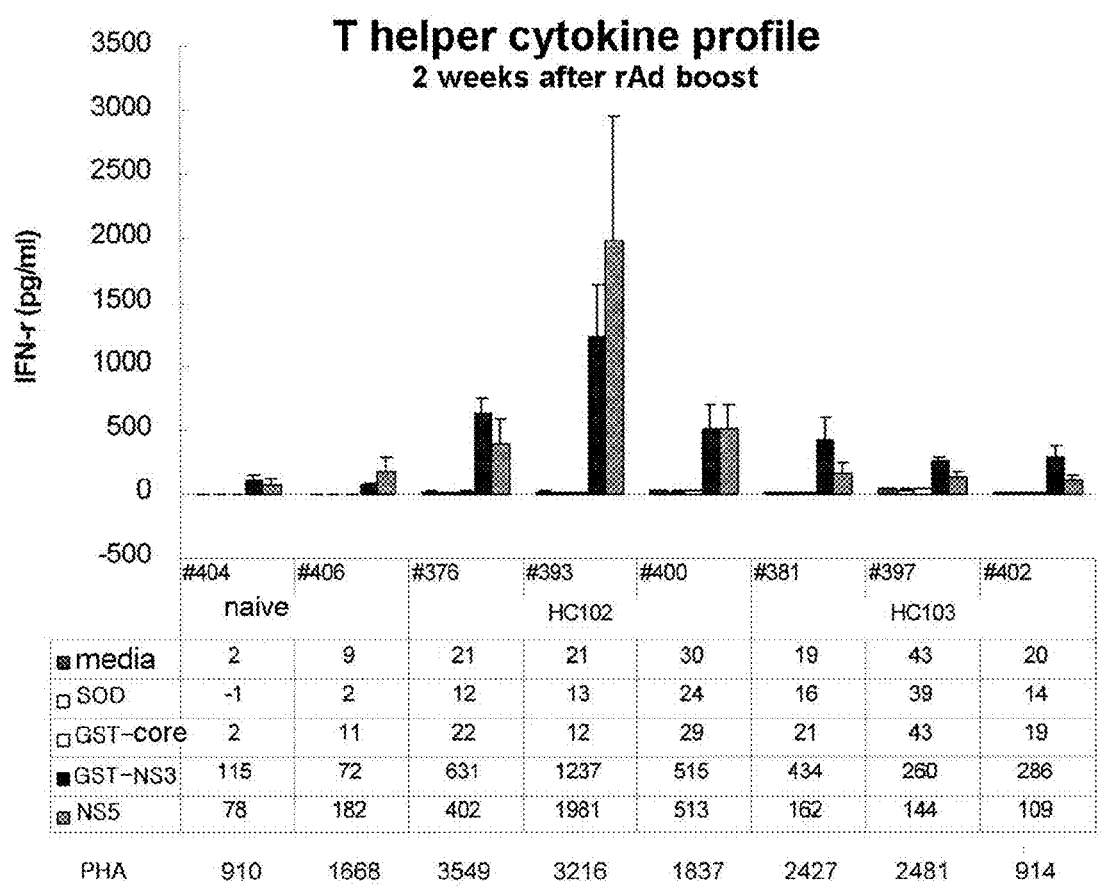
Figure 18:
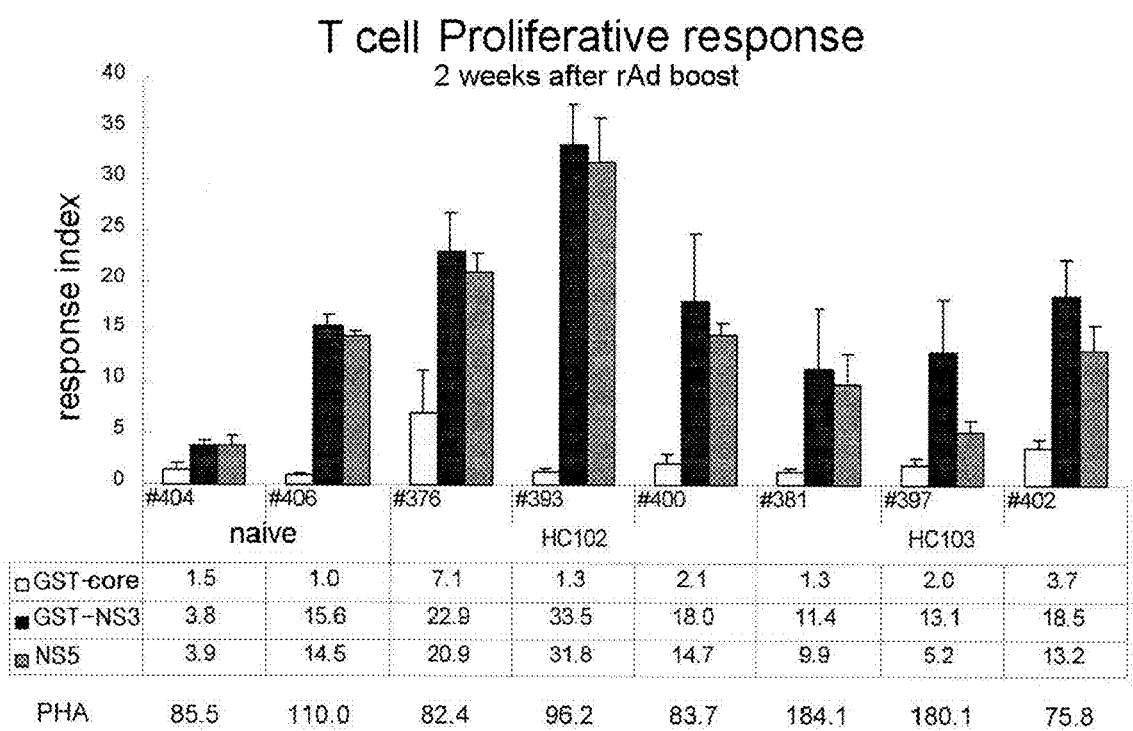
Figure 19:
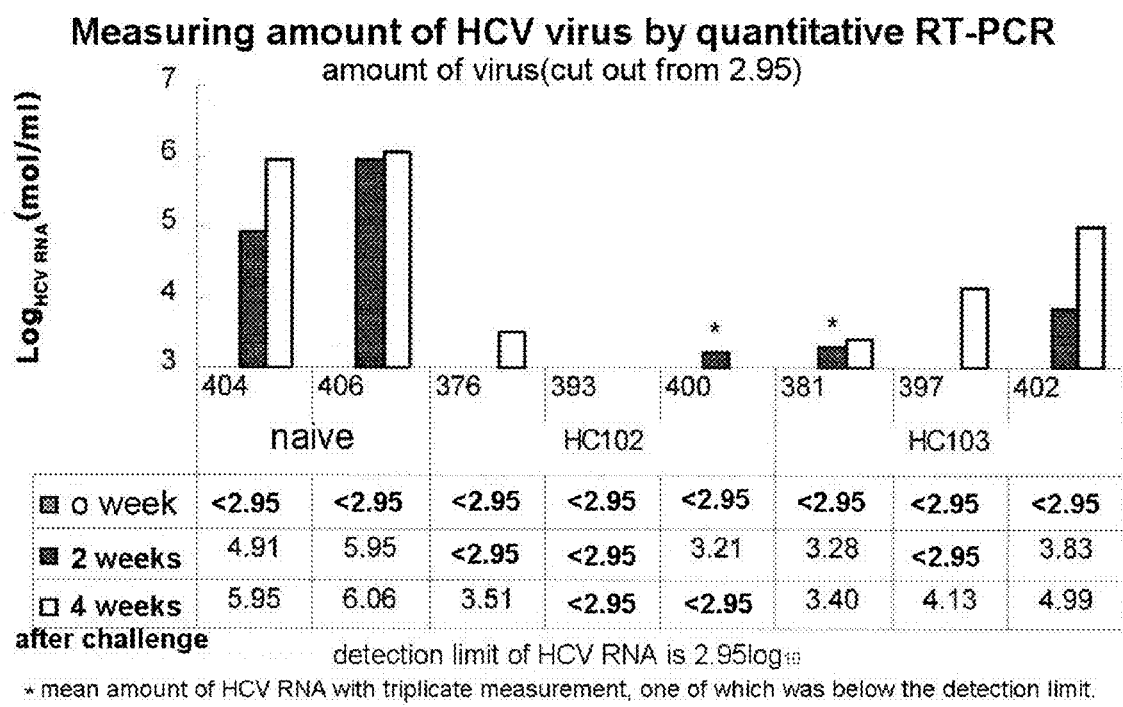

FIG. 15 is a schematic diagram showing the vaccination regimen of the experiments of the invention using chimpanzees with time to confirm the effect of the vaccine of the invention, FIG. 16 is a graph showing the result of IFN-γ ELISPOT analysis of cellular immune response on the second week after recombinant adenovirus boosting in chimpanzee model, FIG. 17 is a graph showing the amount of IFN-γ secreted by CD4+ T cells on the second week after boosting with a recombinant adenovirus in a chimpanzee model, FIG. 18 is a graph showing the proliferation of CD4+ T cells on the second week after recombinant adenovirus boosting in chimpanzee model, FIG. 19 is a graph showing HCV viral load in chimpanzees on the 0, $2^{nd}$ and $4^{th}$ week after the challenge with 100 CID$_{50}$ of infectious HCV-bk, which was performed on the $12^{th}$ week after immunization with the vaccine, FIG. 20 is a set of tables showing the amino acid sequences SSEQ ID NOs: 55 to 184) of HCV peptide pool used for the investigation of cellular immune response.

EXAMPLES

Practical and presently preferred embodiments of the present invention are illustrative as shown in the following Examples.

However, it will be appreciated that those skilled in the art, on consideration of this disclosure, may make modifications and improvements within the spirit and scope of the present invention.

The reaction conditions for the molecular cloning process used in the examples of the present invention were as follow.

(1) Restriction Enzyme Treatment

All the enzymes were treated as follows. Plasmid DNA or 2 µg of purified PCR product (1 µg/µl) was treated with 20 unit of restriction enzyme (2 µl), and the buffer solution provided by the supplier (10× solution) was added thereto. The distilled water was then added to make the final volume 50 µl, which was reacted in a 37° C. incubator for 2 hours.

(2) The Ligation of DNA Fragments and the Transformation of *E. coli*

DNA solution was treated with restriction enzyme and then electrophoresed on 0.8% agarose gel (GIBCO-BRL). The agarose gel containing a proper size DNA fragment was cut, and then the DNA was purified using gel extraction kit (QIAGEN). DNA fragments were ligated in the mixture of T4 DNA ligase (Takara) and the buffer solution provided by the supplier in a 16° C. incubator for 10 hours. *E. coli* was transfected with the ligated DNA following the method of Sambrook, et al (Sambrook et al., *Molecular Cloning*, 2nd Ed. 1989).

(3) The Confirmation of DNA Having the Ligated Plasmids in the Transfected *E. coli* and the Purification Thereof DNA was purified from the transformed *E. coli* by the method of Sambrook et al., which was digested with restriction enzyme based on the restriction enzyme map of the target DNA to confirm whether the target plasmids were correctly ligated. After the confirmation, pure DNA was mass-produced.

(4) PCR Amplification

PCR was performed as follows. 200 pmol each of two oligoneucleotide primers, 20 ng of template DNA, 10 unit of Takara exTaq (polymerase), 5 µl of Takara exTaq 10× buffer solution, 5 µl of 2.5 mM dNTP mixture and distilled water were mixed to make the final volume 50 µl. All the PCRs were performed as follows; predenaturation at 94° C. for 4 minutes, denaturation at 94° C. for 1 minute, annealing at 52° C. for 1 minute, polymerization at 72° C. for 1 minute per kb of a target PCR product (0.5 minute/0.5 kb, 3 minutes/3 kb), 30 cycles from denaturation to polymerization, and final extension at 72° C. for 5 minutes. GeneAmp PCR system 2400 (Perkin Elmer) was used for PCR. The obtained PCR products were electrophoresed on agarose gel, and then purified using the gel extraction kit (QIAGEN) by following the manufacturer's instruction. Then, the obtained products were digested with restriction enzyme as the above, which were used for further cloning process.

Other experiments concerning molecular cloning that were not explained herein were performed using the above method introduced by Sambrook et al with a slight modification.

Example 1

Construction of Plasmids Used in this Invention

Figure 1:
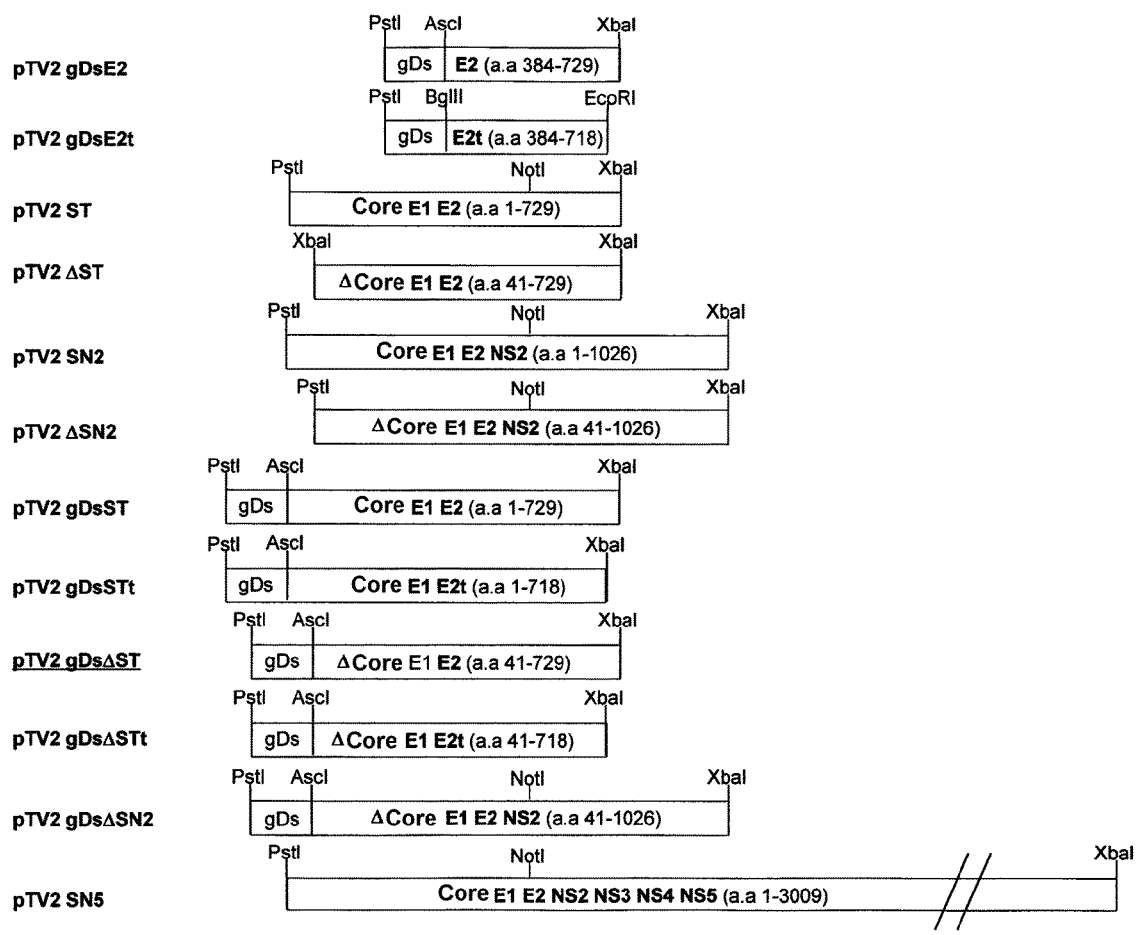
FIG. 1 is a schematic diagram showing the plasmids used for the small animal experiments in this invention (the numbers in parentheses present amino acid ranges of HCV antigen, which are equal to those in FIG. 2-FIG. 4), gDs: Signal sequence of Herpes simplex virus (HSV) glycoprotein D (gD)

The present inventors constructed HCV plasmids (see FIG. 1-FIG. 4) used in this invention as follows.
<1-1> Construction of pTV2 ST pTV2 vector (Lee, *J. Virol.*, 72, 8430, 1998; Cho, *Vaccine*, 17, 1136, 1999) was digested with PstI and XbaI to separate a 4.37 kb size vector. A 2.21 kb size insert was obtained by digesting the PCR product, which was amplified with the primers represented by SEQ. ID. No 1 and No 2 using Korean type HCV gene (see Korea patent No: 120928) that was isolated by the present inventors as a template, with the restriction enzymes PstI and XbaI, which was then combined with the above 4.37 kb size vector to construct pTV2 ST (FIG. 1).

<1-2> Construction of pTV2 Δ ST pTV2 vector (Lee, *J. Virol.*, 72, 8430, 1998; Cho, *Vaccine*, 17, 1136, 1999) was digested with XbaI to separate a 4.78 kb size vector, and then treated with CIAP (Calf intestinal alkaline phosphatase) (Takara). A 2.07 kb size insert was obtained by digesting the PCR product, which was amplified with the primers represented by SEQ. ID. No 2 and No 3 using the pTV2 ST constructed in the above Example <1-2> as a template, with the restriction enzyme XbaI, which was then combined with the above 4.78 kb size vector to construct pTV2 Δ ST (FIG. 1).

<1-3> Construction of pTV2 gDsE2t

<1-3-1> Construction of pSK gDs

PCR was performed with the signal sequence of glycoprotein D of Herpes simplex virus type 1 (gDs; Sisk, 1994, *J. Virol.*, 68: 766) using the primers represented by SEQ. ID. No 40 and No 41. pBluescriopt SK(+) vector (Stratagene) was digested with EcoR V, into which the above PCR product was inserted, leading to the construction of pSK gDs (Lee, 1998 *J Virol* 72: 8430).

<1-3-2> Construction of pTZ HCV

In order to prepare a plasmid having a whole HCV base sequence, PCR was performed with the primers represented by SEQ. ID. No 42 and No 43 using Korean type HCV gene (see Korea Patent No: 120928) as a template. The obtained fragments were digested with the restriction enzymes Hind III and Xba I, which were then inserted into pTZ vector (Sigma) digested with the same restriction enzymes to construct pTZ SN2. The prepared pTZ SN2 was digested with SphI, followed by digesting again with XbaI, resulting in a 5.8 kb size vector. pTV NS345 (Cho, 1999, *Vaccine*, 17:1136-44) was digested with XbaI, followed by the partial digesting again with SphI, leading to the separation of a 6.35 kb insert. The insert was combined with the above 5.8 kb vector to construct pTZ HCV.

<1-3-3> Construction of pTV2 gDsE2t pSK gDs constructed in the above Example <1-3-1> was digested with BglII and EcoRI to prepare a vector. PCR was performed with the primers represented by SEQ. ID. No 4 and No 5 using pTZ HCV constructed in the above Example <1-3-2> as a template. The PCR product was digested with BglII and EcoRI, which was then combined with the vector prepared above to construct pTV2 gDsE2t (Lee, *J. Vol.*, 72: 8430) (FIG. 1).
<1-4> Construction of pTV2 gDsST
<1-4-1> Construction of pTV2 gDs pTV2 gDsE2t constructed in the above Example <1-3> was digested with SpeI and EcoRV to separate a 3.62 kb size vector. A 1.28 kb size insert was obtained by PCR performed with the primers represented by SEQ. ID. No 44 and No 45 using pTV2 gDsE2t as a template, which was then combined with the above 3.62 kb size vector to construct pTV2 gDs.
<1-4-2> Construction of pTV2 gDsST pTV2 gDs constructed in the above Example <1-4-1> was digested with AscI and XbaI to prepare a 4.86 kb vector. PCR was performed with the primers represented by SEQ. ID. No 6 and No 7 using pTV2 ST constructed in the above Example <1-1> as a template. The PCR product was digested with AscI and XbaI, which was combined with the vector obtained above, resulting in the construction of pTV2 gDsST (FIG. 1).
<1-5> Construction of pTV2 gDsE2 pTV2 gDsST constructed in the above Example <1-4> was digested with AscI and XbaI to prepare a 4.86 kb vector. PCR was performed with the primers represented by SEQ. ID. No 7 and No 8 using pTV2 ST constructed in the above Example <1-1> as a template. The PCR product was digested with AscI and XbaI, which was combined with the vector obtained above, resulting in the construction of pTV2 gDsE2 (FIG. 1).
<1-6> Construction of pTV2 gDsΔ SN2 pTV2 gDs constructed in the above Example <1-4-1> was digested with AscI and XbaI to prepare a 4.89 kb vector. PCR was performed with the primers represented by SEQ. ID. No 9 and No 10 using pTZ HCV constructed in the above Example <1-3-2> as a template. The PCR product was digested with AscI and XbaI, which was combined with the vector obtained above, resulting in the construction of pTV2 gDsΔ SN2 (FIG. 1)
<1-7> Construction of pTV2 SN2 pTV2 gDsΔ SN2 constructed in the above Example <1-6> was digested with PstI and NotI to prepare a 5.98 kb vector. pTV2 ST constructed in the above Example <1-1> was digested with PstI and NotI to separate a 1.67 kb size insert. The 1.67 kb size insert was then combined with the vector obtained above, resulting in the construction of pTV2 SN2 (FIG. 1).
<1-8> Construction of pTV2 Δ SN2 pTV2 vector (Lee, *J. Virol.*, 72, 8430, 1998; Cho, *Vaccine*, 17, 1136, 1999) was digested with PstI and XbaI to separate a 4.73 kb size vector. A 2.80 kb size insert was obtained by digesting the PCR product, which was amplified with the primers represented by SEQ. ID. No 46 and No 47 using the pTZ HCV constructed in the above Example <1-3-2> as a template, with the restriction enzymes PstI and XbaI, which was then combined with the above 4.73 kb size vector to construct pTV2 Δ SN2 (FIG. 1).
<1-9> Construction of pTV2 SN5 pTV2 ST constructed in the above Example <1-1> was digested with NotI and XbaI to separate a 6.25 kb size vector. pTZ HCV constructed in the above Example <1-3-2> was digested with NotI and XbaI to separate a 7.50 kb size insert. The 7.50 kb size insert was then combined with the vector obtained above, resulting in the construction of pTV2 SN5 (FIG. 1).
<1-10> Construction of pTV2 gDsSTt pTV2 vector (Lee, *J. Virol.*, 72, 8430, 1998; Cho, *Vaccine*, 17, 1136, 1999) was digested with PstI and XbaI to prepare a 4.73 kb size vector. A 2.40 kb size insert was obtained by digesting the PCR product, which was amplified with the primers represented by SEQ. ID. No 11 and No 12 using the pTV2 gDsST constructed in the above Example <1-4> as a template, with the restriction enzymes PstI and XbaI, which was then combined with the above 4.73 kb size vector to construct pTV2 gDsSTt (FIG. 1).
<1-11> Construction of pTV2 gDsΔ ST pTV2 gDs constructed in the above Example <1-4-1> was digested with AscI and XbaI to prepare a 4.89 kb size vector. A 2.07 kb size insert was obtained by digesting the PCR product, which was amplified with the primers represented by SEQ. ID. No 9 and No 7 using the pTV2 ST constructed in the above Example <1-1> as a template, with the restriction enzymes AscI and XbaI, which was then combined with the above 4.89 kb size vector to construct pTV2 gDsΔ ST (FIG. 1).
<1-12> Construction of pTV2 gDsΔ STt pTV2 vector (Lee, *J. Virol.*, 72, 8430, 1998; Cho, *Vaccine*, 17, 1136, 1999) was digested with PstI and XbaI to prepare a 4.73 kb size vector. A 2.28 kb size insert was obtained by digesting the PCR product, which was amplified with the primers represented by SEQ. ID. No 11 and No 12 using the pTV2 gDsα ST constructed in the above Example <1-11> as a template, with the restriction enzymes PstI and XbaI, which was then combined with the above 4.73 kb size vector to construct pTV2 gDsΔ STt (FIG. 1).
<1-13> Construction of pGX10 gDsΔ ST
<1-13-1> Construction of pGX10
<1-13-1-1> Construction of pTV-3

2 μg of vector 'pMT-2' (Sambrook, *Molecular cloning*, 2nd Ed., Vol. 3, 16.20; Kaufman R J, *Mol. Cell Biol.* 9,946-958, 1989) was digested with HpaI (20 unit) and NheI (20 unit) by the same method as explained above, and Klenow fragment (New England Biolabs) (5 unit) and dNTP (Takara) were added to make the final concentration 100 μM, which was treated at 25° C. for 30 minutes to make blunt end. After completing electrophoresis on agarose gel, the obtained 0.7 kb fragment (the whole adenovirus VAI (Viral Antagonist I) and a part of SV40 polyA were included) was inserted in the specific HpaI site of SV40 polyA region of the vector pTV-2 (Lee, 1998 *J Virol.*, 72,8430-36), resulting in the construction of 5.3 kb size vector 'pTV-3'.
<1-13-1-2> Construction of pGX-1

PCR was performed using the vector pTV-3 constructed in the above Example <1-13-1-1> as a template with the primers represented by SEQ. ID. No 13 and No 14, and the PCR product (2.0 kb) was digested with NruI. PCR was also performed using the vector pZero-2 (Invitrogen) as a template with the primers represented by SEQ. ID. No 15 and No 16, and the product was digested with SspI. The obtained fragment (1.8 kb) was ligated with the above DNA fragment (2.0 kb) to construct 3.8 kb size vector 'pGX-1'.
<1-13-1-3> Construction of pGX10

Figure 2:
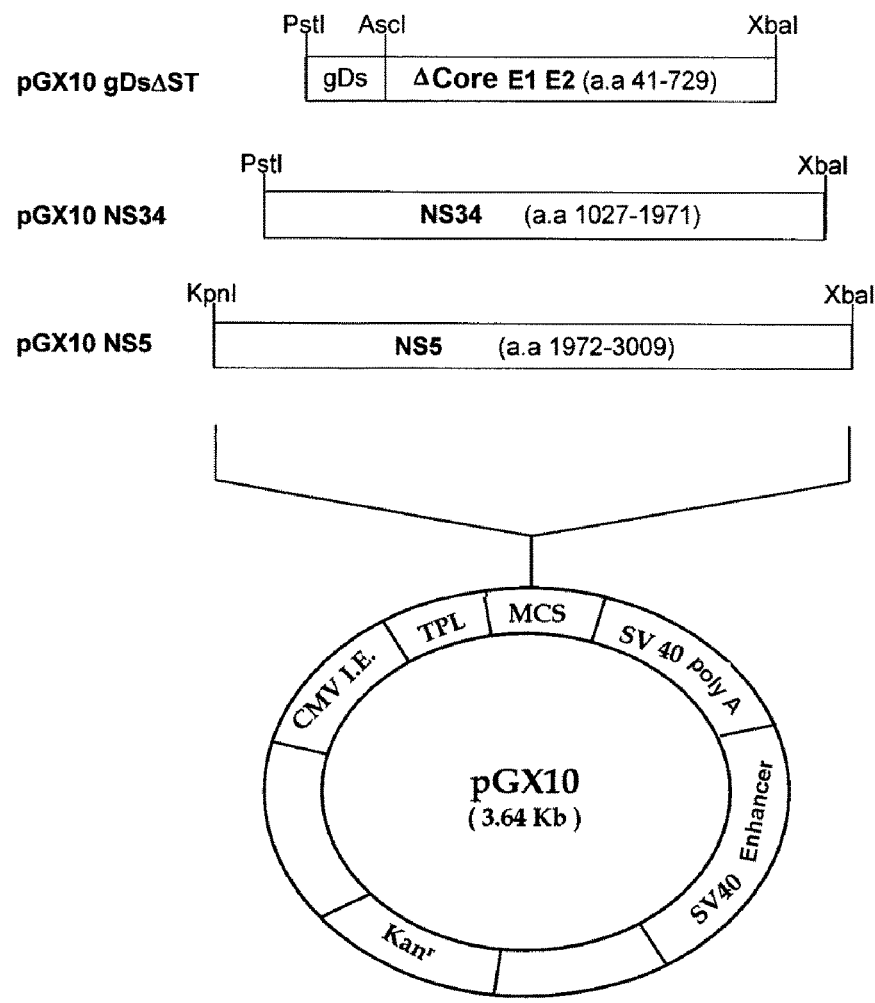
FIG. 2 is a schematic diagram showing the plasmid 'HC102' used for chimpanzee experiments of the present invention.

The vector pGX-1 constructed in the above Example <1-13-1-2> was digested with restriction enzymes XbaI and SalI, and the bigger DNA (3.1 kb) of the two fragments was separated by the method used for the ligation of DNA fragments and for the transformation of *E. coli*. The vector pGL3-enhancer (Promega) was also digested with the restriction enzymes XbaI and SalI, and the smaller DNA (0.5 kb) of the obtained two fragments was separated as the above. The two separated fragments were ligated to construct the vector pGX10 (FIG. 2).
<1-13-2> Construction of pGX10 gDsΔ ST A 3.4 kb size vector was obtained by digesting pGX10, constructed in the above Example <1-13-1>, with PstI and XbaI, which was then ligated to a 2.22 kb size insert obtained by digesting pTV2 gDsΔ ST which was constructed in the above Example <1-11> with PstI and XbaI to construct pGX10 gDsΔ ST containing the base sequence (gDsΔ ST) represented by SEQ. ID. No 50 (FIG. 2). The constructed plasmid was deposited at the Korean Culture Center of Microorganisms, located at 361-221, Yurim B/D, Honje 1, Sudaemun-gu, Seoul, 120-091, Republic of Korea, on Aug. 29, 2002 (Accession No: KCCM 10415).

<1-14> Construction of pGX10 NS34

A 3.56 kb size vector was obtained by digesting pGX10 gDsΔ ST constructed in the above Example <1-13> with AscI and XbaI. PCR was performed using pTZ HCV, constructed in the above Example <1-3-2>, with the primers represented by SEQ. ID. No 17 and No 18. The above vector was ligated to a 2.82 kb insert prepared by digesting the PCR product with PstI and XbaI, resulting in the construction of pGX10 NS34 containing the base sequence (NS34) represented by SEQ. ID. No 51 (FIG. 2). The obtained plasmid was deposited at the Korean Culture Center of Microorganisms, located at 361-221, Yurim B/D. Honie 1, Sudaemun-gu, Seoul, 120-091, Republic of Korea., on Aug. 29, 2002 (Accession No: KCCM 10417).

<1-15> Construction of pGX10 NS5

A 3.4 kb size vector was constructed by digesting pGX10, constructed in the above Example <1-13-1>, with Asp718 and XbaI. PCR was performed using pTZ HCV, constructed in the above Example <1-3-2>, as a template with the primers represented by SEQ. ID. No 19 and No 20. A 3.12 kb size insert, obtained by digesting the PCR product with Asp718 and XbaI, was ligated to the above vector, resulting in the construction of pGX10 NS5 containing the base sequence (NS5) represented by SEQ. ID. No 52 (FIG. 2). The obtained plasmid was deposited at the Korean Culture Center of Microorganisms, located at 361-221, Yurim B/D, Honie 1, Sudaemun-gu, Seoul, 120-091, Republic of Korea., on Aug. 29, 2002 (Accession No: KCCM 10416).

<1-16> Construction of pGX10 hIL-12m (pGX10-hp35/IRES/hp40-N222L)

<1-16-1> Construction of pSK-hp35 and pSK-hp40

After cloning cDNAs of 820 bp size human p35 subunit and 1050 bp size p40 subunit from NC37 cells (American Type Culture Collection; ATCC), human B cells activated by PMA (phorbol myrystic acetate), using RT-PCR (Reverse transcriptase-polymerase chain reaction, PCR System 2400, Perkin Elmer), PCR was performed with the primers represented by SEQ. ID. No 21 and No 22 for the 820 bp human p35 subunit, and with the primers represented by SEQ. ID. No 23 and No 24 for the 1050 bp size p40 subunit.

The amplified cDNAs were subcloned into the starting vector pBluescript SK+ (Stratagene). Each gene of p35 and p40 subunit was also inserted into the SamI site of the vector to construct pSK-hp35 (3.8 kb) and pSK-hp40 (4.0 kb).

<1-16-2> Construction of pSK-IRES

In order to construct a vector (bicistronic vector) expressing genes encoding p35 and p40 subunits, RT-PCR was performed using the primers represented by SEQ. ID. No 25 and No 26, to obtain IRES (Internal Ribosome Entry Site) gene of EMCV (Encephalomyocarditis virus). The IRES gene was digested with EcoRV, which was then inserted into EcoRV site of pBluescript SK+ to construct the vector pSK-IRES (3.5 kb).

<1-16-3> Construction of pSK-hp35/IRES

A 3.5 kb size vector was obtained by digesting pSK-IRES, constructed in the above Example <1-16-2>, with the restriction enzyme EcoRV. pSK-hp35 constructed in the above Example <1-16-1> was also digested with the restriction enzymes EcoRV and NotI. Then, hp35 fragment (0.8 kb) which was filled in with T4 DNA polymerase was inserted into the above vector to construct pSK-hp35/IRES (4.3 kb).

<1-16-4> Construction of pSK-hp35/IRES/hp40

The hp40 fragment (1.0 kb), obtained by digesting the vector pSK-hp40 constructed in the above Example <1-16-1> with NcoI and NotI, was inserted into the digested area of pSK-hp35/IRES constructed in the above Example <1-16-3> by the same restriction enzymes. As a result, a vector that can express both genes encoding p35 subunit and p40 subunit simultaneously was constructed. And the vector was digested with the restriction enzymes SmaI and ClaI, followed by re-ligation using T4-ligase, so that a part of the restriction enzyme site in front of hp35 was eliminated. At last, the vector pSK-hp35/IRES/hp40 was constructed.

<1-16-5> Construction of pSK-hp40-N222L

In order to replace aspartic acid, the $222^{nd}$ amino acid of hp40, by leucine, PCR was performed with the primers represented by SEQ. ID. No 27 and No 28 using pKS-hp40 constructed in the above Example <1-16-1> as a template. Likewise, secondary PCR was performed using the primers represented by SEQ. ID. No 29 and No 30. So, two PCR fragments, which were sharing the common site including a mutational point, were made. The secondary PCR was performed using the mixture of the above fragments as a template and the flanking primers. As a result, a fusion product was obtained, which was inserted into the vector pBluescriptSK+ (Stratagene, 3.0 kb) prepared by digesting the fragments with SmaI to construct the plasmid pSK-hp40-N222L (4.0 kb).

<1-16-6> Construction of pSK-hp35/IRES/hp40-N222L hp40-N222L fragment of pSK-hp40-N222L constructed in the above Example <1-16-5> was substituted with hp40 fragment of pSK-hp35/IRES/hp40 constructed in the above Example <1-16-4> using the restriction enzymes NcoI and NotI to construct the plasmid pSK-hp35/IRES/hp40-N222L (5.3 Kb).

<1-16-7> Construction of pGX10-hp35/IRES/hp40-N222L

Figure 3:
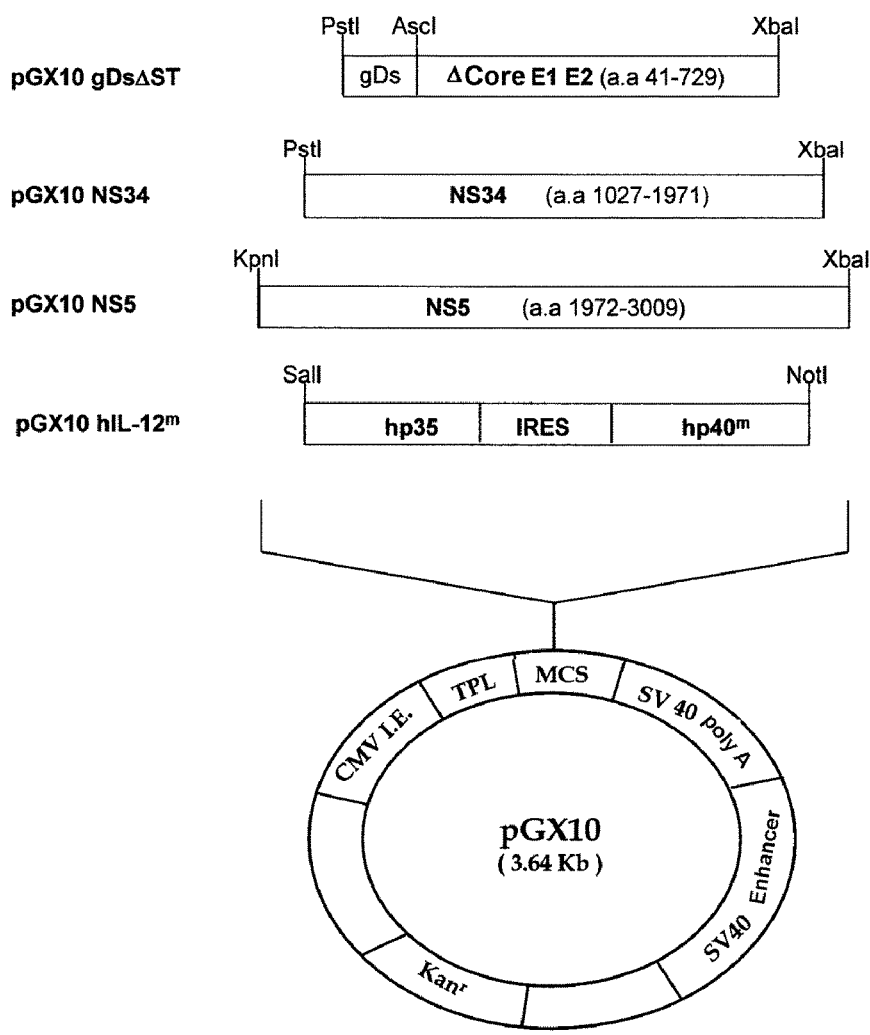
FIG. 3 is a schematic diagram showing the plasmid 'HC103' used for chimpanzee experiments of the present invention.

In order to transfer the fragment hp35/IRES/hp40-N222L to a vector that is able to express the gene in mammalian cell, PCR was performed using pSK-hp35/IRES/hp40-N222L constructed in the above Example <1-16-6> as a template and the primers represented by SEQ. ID. No 31 and No 32, so that the vector was amplified to produce the fragment hp35/IRES/hp40-N222L. The obtained fragment was digested with the restriction enzyme XhoI, which was then inserted into XhoI site of pGX10 prepared in the above Example <1-13-1>. As a result, the 5.9 kb size plasmid 'pGX10-hp35/IRES/hp40-N222L' (pGX10 hIL-12m) containing the base sequence represented by SEQ. ID. No 53 (hIL-12m) was produced (FIG. 3).

Example 2

Construction of the Recombinant Adenovirus Used in this Invention

<2-1> Construction of pShuttleCMV gDsΔ ST

<2-1-1> Construction of pShuttleCMV gDsΔ ST:H77C pShuttleCMV (Q biogene Co.) was digested with BglII and XbaI to separate a 7.5 kb size vector. A 2.07 kb size insert was obtained by digesting the PCR product, which was amplified with the primers represented by SEQ. ID. No 33 and No 34 using pCV-H77C (Masayuki, 1998 *Virology* 244: 161-72) as a template, with the restriction enzymes BglII and XbaI, which was then combined with the above 7.5 kb size vector to construct pShuttleCMV.gDsΔ ST:H77C.

<2-1-2> Construction of pShuttleCMV gDsΔ ST pShuttleCMV gDsΔ ST:H77C constructed in the above Example <2-1-1> was digested with AscI and XbaI to separate a 7.43 kb size vector. pGX10 gDsΔ ST constructed in the above Example <1-13-2> was also digested with AscI and XbaI to obtain a 2.07 kb size insert. The obtained insert was ligated with the above 7.43 kb size vector to construct pShuttleCMV gDsΔ ST.

<2-2> Construction of pShuttleCMV gDsNS34

<2-2-1> Construction of pGX10 gDsNS34 pGX10 gDsΔ ST constructed in the above Example <1-13-2> was digested with AscI and XbaI to separate a 3.5 kb size vector. A 2.81 kb size insert was obtained by digesting the PCR product, which was amplified with the primers represented by SEQ. ID. No 48 and No 49 using pTZ HCV constructed in the above Example <1-3-2> as a template, with the restriction enzymes AscI and XbaI, which was then combined with the above 3.5 kb size vector to construct pGX10 gDsNS34.

<2-2-2> Construction of pShuttleCMV gDsNS34 pShuttleCMV gDsΔ ST constructed in the above Example <2-1-2> was digested with AscI and XbaI to separate a 7.43 kb size vector. pGX10 gDsNS34 constructed in the above Example <2-2-1> was also digested with AscI and XbaI to obtain a 2.81 kb size insert. The obtained insert was ligated with the above 7.43 kb size vector to construct pShuttleCMV gDsNS34.

<2-3> Construction of pShuttleCMV NS5 pShuttleCMV (Q biogene Co.) was digested with Asp718 and XbaI to separate a 7.46 kb size vector. A 3.12 kb size insert was obtained by digesting the PCR product, which was amplified with the primers represented by SEQ. ID. No 19 and No 20 using pTZ HCV constructed in the above Example <1-3-2> as a template, with the restriction enzymes Asp718 and XbaI, which was then combined with the above 7.46 kb size vector to construct pShuttleCMV NS5.

<2-4> Construction of pGX10 mIL-12m

<2-4-1> Construction of Wild-Type Mouse IL-12 Expression Vector

<2-4-1-1> Construction of pSK-mp35/IRES/mp40

In order to prepare a vector simultaneously expressing the genes each coding mouse p40 subunit and p35 subunit, the vector pSK-IRES, constructed in the above Example <1-16-2>, containing IRES of EMCV was digested with the restriction enzymes NcoI and BamHI. Mouse IL-12p40 PCR product (Schoenhaut, *J. Immunol.*, 1999, 148:3433-3440) was also digested with the same restriction enzymes, resulting in a p40 DNA fragment. The p40 DNA fragment was inserted into the above vector to construct pSK-IRES/mp40. Mouse IL-12p35 product (Schoenhaut, *J. Immunol.*, 1992, 148: 3433-3440) was digested with BamHI, and the end of the fragment was filled in by T4 DNA polymerase. The fragment was inserted into pSK-IRES/mp40 treated with ClaI and T4 DNA polymerase. As a result, the plasmid pSK-mp35/IRES/mp40 was constructed, in which p35, IRES and p40 were arranged in that order.

<2-4-1-2> Construction of the Expression Vector pCIN-mp35/IRES/mp40 mp35/IRES/mp40 constructed by the same method as used in the above Example <2-4-1-1> was inserted into XhoI and NotI sites of pCI-neo vector (Promega Co.), to construct the expression vector 'pCIN-mp35/IRES/mp40' that was able to express active form of IL-12p70 in mammalian cells.

<2-4-2> Construction of the Expression Vector pCIN-mp40

In order to construct a plasmid expressing wild-type mouse p40 subunit, the vector pSK-mp35/IRES/mp40 constructed in the above Example <2-4-1-1> was digested with the restriction enzymes NcoI and SacI, to obtain p40 fragment, which was, then, inserted into the vector pGEX-KG (Clontech Co., USA) treated with the same restriction enzymes. The prepared pGEX-KG-mp40 was treated with EcoRI and NotI, which was inserted into the EcoRI and NotI sites of pCI-neo. As a result, the expression vector pCIN-mp40 was obtained.

<2-4-3> Construction of the Expression Vector pCIN-mp35

In order to construct a plasmid expressing wild-type p35 subunit, the vector pSK-mp35/IRES/mp40 constructed in the above Example <2-4-1-1> was digested with the restriction enzymes XhoI and EcoRI, to obtain p35 fragment, which was, then, inserted into the XhoI and EcoRI sites of the vector pCI-neo treated with the same restriction enzymes to construct the expression vector pCIN-mp35.

<2-4-4> Construction of the Expression Vector pCIN-mp40-N220L

In order to replace aspartic acid, the $220^{th}$ amino acid of mp40, by leucine, PCR was performed using pCIN-mp40 constructed in the above Example <2-4-2> as a template and primers represented by SEQ. ID. No 35 and No 36. At that time, the restriction enzyme SacI recognition site was included for easy discrimination. Thus, the vector pCIN-mp40-N220L, which contained mouse IL-12p40 mutant gene and was able to be expressed in animal cells, was prepared.

<2-4-5> Construction of pTV2-mp35/IRES/mp40-N220L

In order to construct a DNA expressing the genes coding p40 and p35 subunits simultaneously for DNA immunization, pTV2 vector (Lee, *J. Virol.*, 72:8430-8436, 1998; Cho, *Vaccine*, 17:1136-1144, 1999), which is an eukaryotic expression vector and has been used as a DNA vaccine vector in small animal models, was digested with the restriction enzymes Asp718 and NotI. mp 35/IRES/mp 40 fragment was prepared by digesting pSK-mp 35/IRES/mp 40, constructed in the above Example <2-4-1-1>, with the same restriction enzymes, which was inserted into the above restriction enzyme sites to construct the vector pTV2-mp 35/IRES/mp 40. And in order to construct a vector containing Asn-220 mutant gene of mouse IL-12p40 and expressing p35 at the same time, pSK-mp 35/IRES/mp 40 was digested with NcoI and NotI, into which mp 40-N220L fragment obtained by cutting pCIN-mp 40-N220L by the same enzymes was inserted, resulting in the construction of pSK-mp 35/IRES/mp 40-N220L. pTV2-mp 35/IRES/mp 40 was digested with EcoRV and NotI to eliminate mp 40, into which mp 40-N220L fragment obtained by digesting pSK-mp 35/IRES/mp 40-N220L with the same enzymes was inserted, resulting in the construction of the vector pTV2-mp 35/IRES/mp 40-N220L. The vector was deposited at the Gene Bank of Korea Research Institute of Bioscience and Biotechnology, located at 111 Gwahangno, Yuseong-gu, Daejeon, South Korea, on Feb. 29, 2000 (Accession No: KCTC 0745BP).

<2-4-6> Construction of pGX10 mIL-12

The DNA fragment (2.5 kb), obtained by digesting the vector pTV2-mp35/IRES/mp40-N220L with SacII and NotI, was combined with the other DNA fragment (3.4 kb), obtained by digesting pGX10 with the same restriction enzymes, to construct the vector pGX10 mIL-12 mutant (5.9 kb).

<2-5> Construction of the Recombinant Adenovirus rAd-gDsΔ ST

Figure 4:
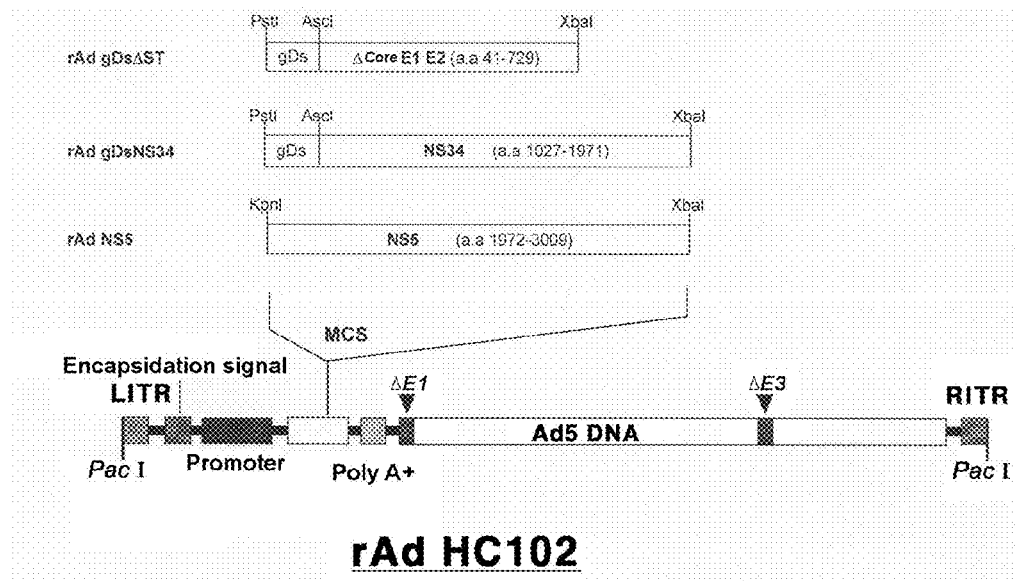
FIG. 4 is a schematic diagram showing the recombinant adenovirus (rAd) used in the present invention.

The recombinant adenovirus rAd-gDsΔ ST of the present invention was prepared by using pAdEasy (Trade mark) vector system (Q. Biogene Co.). pShuttleCMV gDsΔ ST, constructed in the above Example <2-1>, was digested with PmeI, which was used, along with the vector pAdEasy, for transformation of *E. coli* strain BJ5183 by electroporation.

rAd gDsΔ ST containing the base sequence represented by SEQ. ID. No 50 (gDsΔ ST) was constructed by the homologous recombination process within the bacterial strain (FIG. 4). DNA was extracted from the transformed cells and then digested with the restriction enzyme PadI. 293A cells (ATCC) which had been cultured on 60 mm dish were transfected with the DNA by calcium phosphate method. 10 days later, the transfected cells were frozen and then melted, which was-repeated three times. Supernatant was separated and used for re-transfection of freshly cultured 293A cells on 100 mm dish for amplification. The virus was cultured for three days with the same procedure, and at last, amplified on 150 mm dish until the quantity of 293A cells were increased to 30 units of 150 mm dishes. 293A cells were harvested, from which only the pure recombinant adenoviruses were purified according to the manufacturer's instruction (Q. Biogene Co.). The purified viruses were quantified by the method of $TCID_{50}$ (Tissue Culture Infectious Dose 50). As a result, about $1 \times 10^{11}$ pfu of recombinant adenovirus rAd gDsΔ ST were obtained. The above recombinant adenovirus was deposited at the Korean Culture Center of Microorganisms, located at 361-221, Yurim B/D, Honje 1, Sudaemun-gu, Seoul, 120-091, Republic of Korea, on Aug. 29, 2002 (Accession No: KCCM 10418).

<2-6> Construction of the Recombinant Adenovirus rAd-gDsNS34 rAd-gDsNS34 containing the base sequence represented by SEQ. ID. No 54 (gDsNS34) was constructed using pShuttleCMV gDsNS34 constructed in the above Example <2-2-2> by the same method as used for the production of rAd-gDsΔ ST in the above Example <2-5>. The recombinant adenovirus rAd-gDsN34 was deposited at the Korean Culture Center of Microorganisms, Yurim B/D, Honje 1, Sudaemun-gu, Seoul, 120-091, Republic of Korea, on Aug. 29, 2002 (Accession No: KCCM 10420).

<2-7> Construction of the Recombinant Adenovirus rAd-NS5 rAd-NS5 containing the base sequence represented by SEQ. ID. No 52 (gDsNS34) was constructed using pShuttleCMV NS5 constructed in the above Example <2-2-2> by the same method as used for the production of rAd-gDsE ST in the above Example <2-5> (FIG. 4). The recombinant adenovirus rAd-NS5 was deposited at the Korean Culture Center of Microorganisms, Yurim B/D, Honje 1 Sudaemun-gu, Seoul, 120-091, Republic of Korea, on Aug. 29, 2002 (Accession No: KCCM 10419).

Example 3

Identification of the Expressions of Core, E2, NS3, NS4 and NS5 in HCV DNA Vaccine and Recombinant Adenovirus Vaccine (FIG. 5-FIG. 8)

The present inventors confirmed the expressions of HCV antigens—core, E2, NS3, NS4 and NS5—in various DNA vaccine plasmids and recombinant adenovirus vaccines constructed in the present invention using the methods explained above. At first, COS-7 cells were used to confirm the expressions of the plasmids constructed in this invention. COS-7 cells were cultured in DMEM medium (Gibco BRL Co.) containing 10% FBS (fetal bovine serum). $5 \times 10^5$ cells were plated onto 60 mm dish for the culture. Next day, the cells were transfected with 10 μg each of the plasmids presented in the FIGS. 5, 6 and 7, using calcium phosphate method. 36 hours later, cells were collected for electrophoresis. In order to normalize the variation of transfection efficiency, 5 μg of luciferase gene was mixed with the indicated plasmids before the transfection, and cell lysate having the same activity level of luciferase was taken for electrophoresis. 293A cells were used to confirm the expression of the recombinant adenovirus. 293A cells which had been cultured on 60 mm dish were infected with the recombinant adenovirus by $1 \times 10^6$ pfu of the recombinant virus per $5 \times 10^5$ cells, as seen in FIG. 8, and 36 hours later, the cells were harvested for electrophoresis. After running the electrophoresis on 10% SDS-polyacrylamide gel, Western blotting was performed. In order to detect E2 protein, anti-E2 monoclonal antibody (Lee, 1999 *J Virol* 73: 11-8) was used. In order to detect Δ core protein in which N-terminal 40 amino acids were removed, anti-core polyclonal antibody was used. And in order to detect non-structural protein such as NS3, NS4 and NS5, serum of HCV patient was used.

Figure 5:
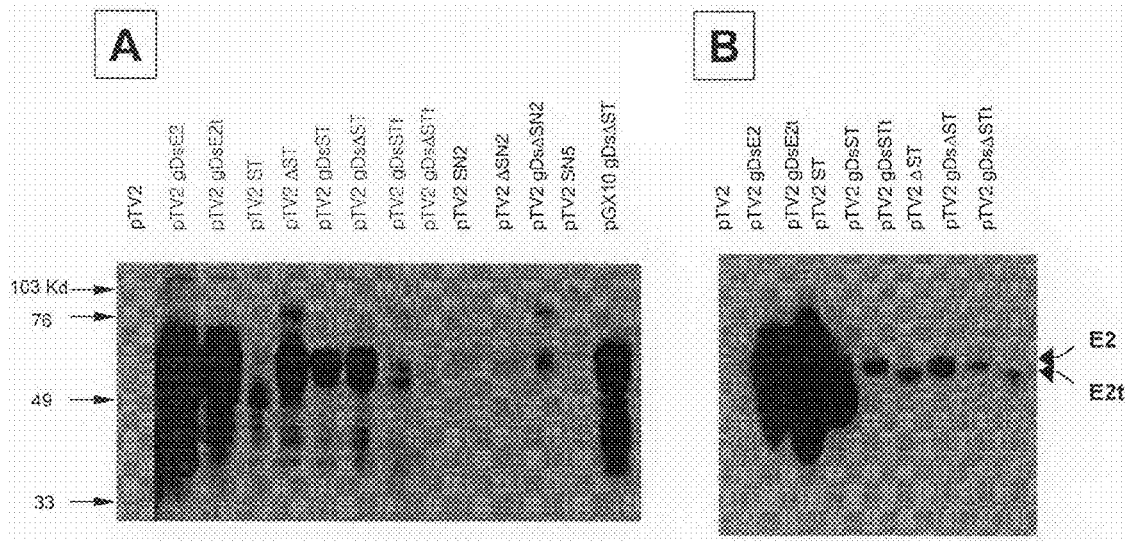
FIG. 5 is a set of electrophoresis photographs showing whether HCV antigens are expressed in COS-7 cell line, by the plasmid used for the small animal samples in the present invention, which was confirmed by Western blot analysis using monoclonal antibodies to HCV E2.

FIG. 5 shows the expression of E2 protein in the plasmids used in small animal experiments. In that figure, (A) provides a good comparison of expression levels of the plasmids used in the experiments, and (B) shows the difference of molecular weights after the elimination of transmembrane domain. E2 has 38 KDa in molecular weight, but a band of 65-70 KDa was detected because of glycosylation in endoplasmic reticulum (ER) and golgi complex. In general, the longer the insert introduced in a plasmid was, the lower the expression level was. pTV2 SN5 formed a specific band at the right position, although it was faint but good enough to confirm the expression. The changes in migration rate of E2 after the elimination of transmembrane domain suggested that the domain was correctly removed.

Figure 6:
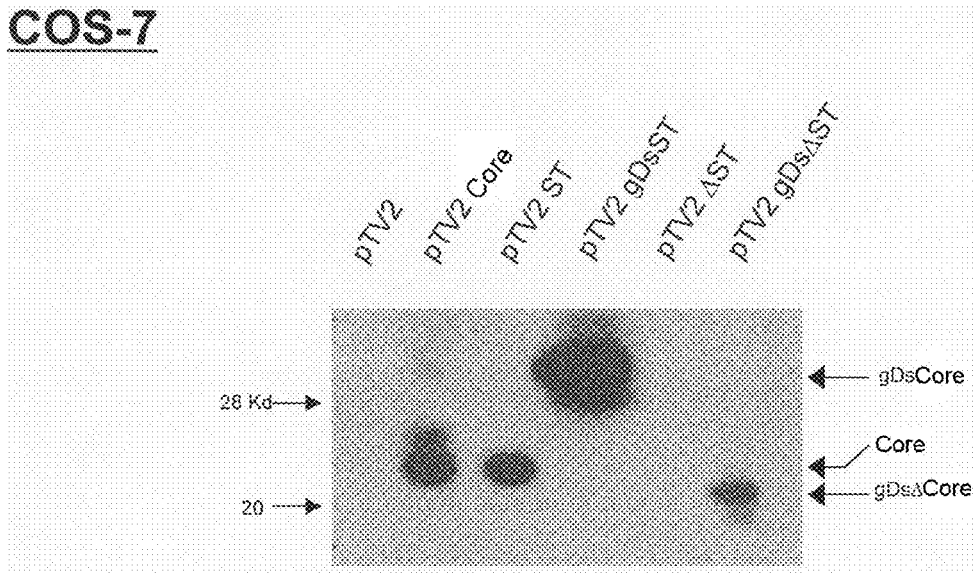
FIG. 6 is an electrophoresis photograph showing the expression of core of the plasmid used for the small animal experiments of the present invention in COS-7 cell line, and the elimination of N terminal 40 amino acids which was confirmed by Western blot analysis using polyclonal antibodies against core.

FIG. 6 shows the expression of core and its elimination of amino terminal 40 amino acids. Core has 21 KDa in molecular weight. It increased to 24 KDa when gDs was inserted, and decreased to 4.5 KDa after amino terminal 40 amino acids were removed. In order to track the position of core on electrophoresis, pTV2 core tested by the present inventors was used. As shown in the figure, the antibody to core specific expression product was seen as a clear band, suggesting that core was expressed and amino terminal 40 amino acids were correctly eliminated. When pTV2 gDsΔ ST was used, the core band seemed to be unclear, comparing to the cases using other plasmids, which, though, did not suggest that the expression of core was weak. First, the major B cell epitope inducing antibody response existed at amino terminus of core, according to previous reports (Sallberg, 1992 *Immunol Lett* 33:27; Kakimi, 1995 *J Gen Virol* 76: 1205; Harase, 1995 *Immunol Cell Biol* 73:346). Thus, even though the expression levels of core in the plasmids were comparable, the antibody is not likely to bind to the core protein in which amino terminus was removed. So, the band was seen lighter than that of a wild type. Second, core, E1 and E2 proteins are processed by the host protease into an individual gene product in that order after polyprotein was produced in the host cell transfected with the plasmids 'pTV2-ST', '-gDsST', '-gDsΔ ST', etc. Based on that, the expression level of each protein was believed to be similar during the synthesis. As seen in FIG. 5A, the level of E2 expression in pTV2 gDsST was similar to that in pTV2 gDsΔ ST. Thus, the weak core band observed in pTV2 gDsΔ ST was not because core was expressed less but because there was a limitation in the binding affinity of anti-core antibody to core protein without amino terminus.

Figure 7:
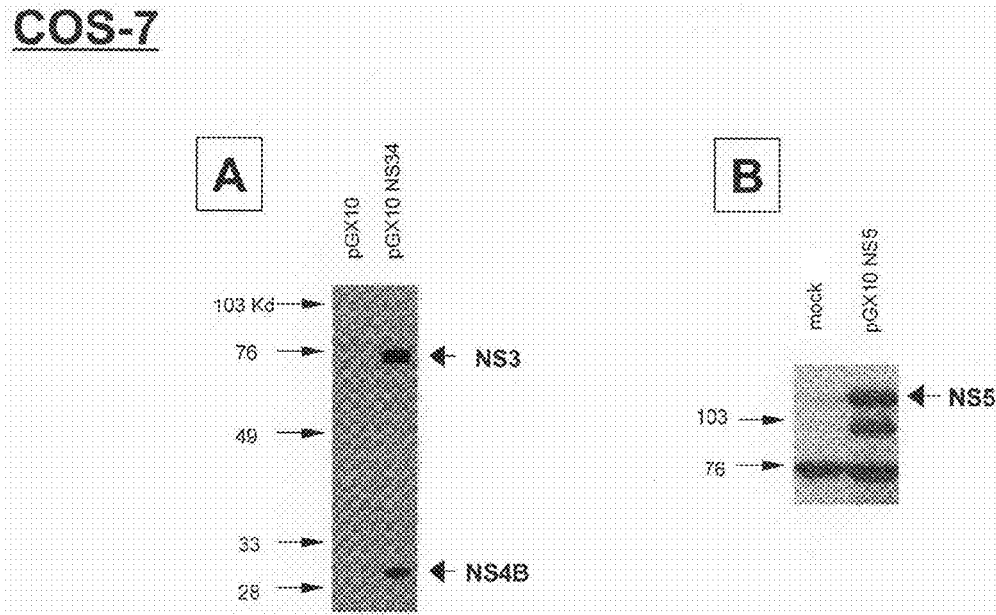
FIG. 7 is a set of electrophoresis photographs showing the expression of the plasmids used in chimpanzee experiments of the present invention in COS-7 cell line, A: Expression of structural protein E2, B: Expression of nonstructural proteins NS3 and NS4B, C: Expression of NS5
Figure 8:
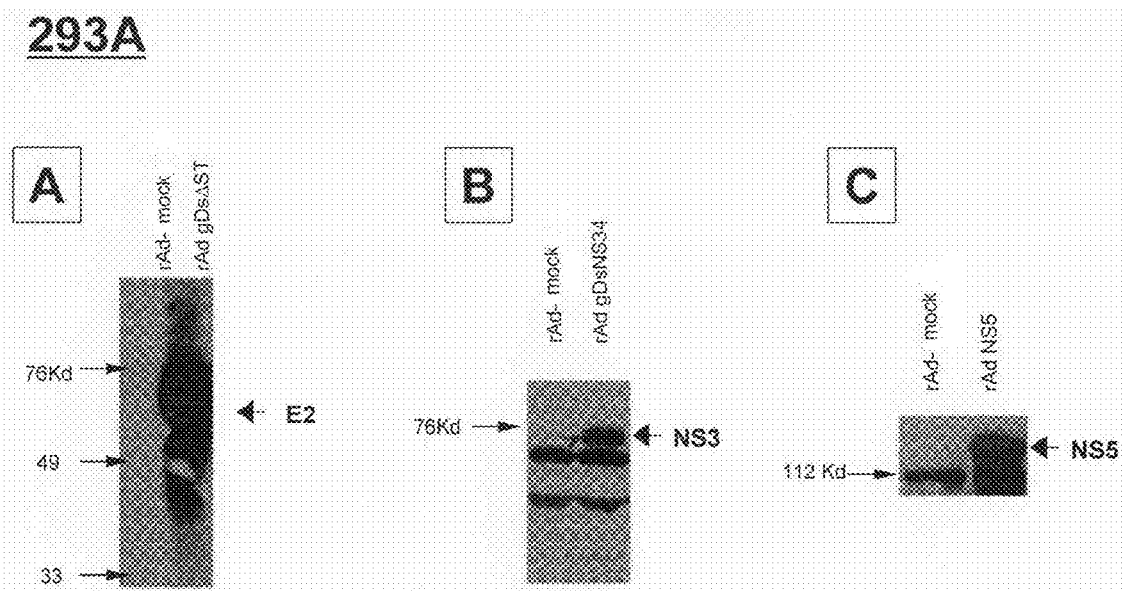
FIG. 8 is a set of electrophoresis photographs showing the expression of the adenoviruses used in chimpanzee experiments of the present invention in 293A cell line, A: Expression of structural protein E2, B: Expression of nonstructural proteins NS3 and NS4B, C: Expression of NS5

FIG. 7 shows the expression of the plasmid used in the experiments with chimpanzees. E2 antibody specific band was observed at the correct position in pGX10 gDsΔ ST (A), and 67 KDa NS3 protein and 27 KDa NS4B protein were confirmed in pGX10, NS34 (B). Generally, when whole non-structural is expressed NS5 protein is detected as divided forms into 49 KDa NS5A and 66 KDa NS5B that are cleavage product by NS3 protease of hepatitis C virus. But in transfected cells with pGX10 NS5 alone, the 115 KDa single band was detected since protease was not provided in this case (C). A specific 100 KDa band was observed, which seemed to be a cleavage product generated by unknown processing during the expression in the cells.

FIG. 8 shows the expression of a recombinant adenovirus. The equal explanation to the case seen in FIG. 7 can be applied to rAd gDsΔ ST (A) and rAd NS5 (c). The molecular weight of rAd gDsNS34 (B) increased to 71 KDa by substituting 67 KDa NS3 protein with gDs, and additionally by the glycosylation occurring after changing the location to ER by inserting gDs.

All the plasmids used in the present invention were confirmed by nucleotide sequencing for translation start site and joining regions in clong procedure. For the identification of structural protein expressions, E2 expression was examined and core expression was tested in some of those proteins. E1 expression was also investigated, but the corresponding band was hardly detected because of low sensitivity and inaccuracy of the antibody used. Nevertheless, E1 was believed to be expressed correctly, considering the fact that core and E2 expressions were clearly observed during the expression process having the order of core-E1-E2.

Through the preferred embodiments of the invention, the present inventors suggest that the target gene product can be expressed after administration in vivo, by observing the expressions of the plasmid and the recombinant adenovirus of the invention in cultured animal cells.

Example 4

Immunization of Mice with a HCV DNA Vaccine and an Adenovirus Vaccine

The mentioned plasmid was dissolved in 100 µl of PBS, which was used as a DNA vaccine for the immunization of small animals. The first administration was performed by injecting 100 µl of a DNA vaccine into both legs (50 µl per each hind leg muscle) of 6 mice per each group. In some cases, the secondary intramuscular injection followed 4 weeks later. In the example (FIG. 9-FIG. 12) aiming at enhancing the immunogenicity by antigen engineering, 100 µg of DNA was used. Otherwise, 50 µg of DNA, prepared by mixing 40 µg of the plasmid pGX10 gDsAST and 10 µg of the mutant pGX10 mL-12, was used for the immunization in FIG. 13 and FIG. 14. $5 \times 10^7$ pfu of rAd gDsΔST was dissolved in saline, which was used as a recombinant adenovirus vaccine (rAd). In order to investigate cellular immune response induced after immunization, spleen cells were isolated at the indicated time. A control group was injected with saline alone.

Example 5

IFN-γ ELISPOT Analysis with Mice

IFN-γ ELISPOT analysis was performed according to the manufacturer's instruction using IFN-γ ELISPOT kit (Cat# M34201-H, MABTECH Co.) after pooling spleen cells taken from 2-3 immunized mice. Particularly, the coating antibody (1-D1K) for IFN-γ was diluted with PBS by 5 µg/ml, and 50 µl of the diluted antibody solution was distributed into a 96 well plate (Millipore, 0.45m, Cat# MAHAS4510, Bedford, Mass.), which was then left at room temperature for over 12 hours. The remaining antibody solution was removed by suction. The plate was washed with PBS twice, and 200 µl of medium for animal cell culture (RPMI-1640 containing 50 units/ml penicillin, 50 µg/ml streptomycin, 50 µM β-mercaptoethanol, 2 mM L-glutamine, 1 mM sodium pyruvate, 20 units/ml recombinant mIL-2 and 10% FBS (standard fetal bovine serum, HyClone, Lot. #AJH10775)) was added into each well. After leaving the plate at 37° C. for over 2 hours, the remaining solution was removed by suction again. The isolated spleen cells were added into each well by $1 \times 10^6$, $3.3 \times 10^5$ and $1.1 \times 10^5$ cells/well respectively. In order to investigate the HCV antigen specific immune response caused by CD8+ T cells, the cell line 'CT26-hghE2t', which has been known to express H-2d MHC class I and E2 protein of hepatitis C virus stably at the same time (Song, *J. Virol.*, 74:2920-2925, 2000), was added into each well by $2 \times 10^4$ cells/well. Then, the 96 well plate was cultured in a 37° C., 5% $CO_2$ incubator without agitation for 20 hours. After stimulation, contents in the 96 well plate were poured out, and washed with washing solution (PBS-T, 0.1%) containing 0.1% tween 20 (Sigma, Cat# D8654) four times. Biotin-labeled mAb (7-B6-1 biotin) was diluted with blocking buffer, prepared by adding 1% BSA to the washing solution, to adjust the concentration to 1 µg/ml. That was added into each well by 50 µl, followed by incubation for 2 hours. After being washed with the washing solution (PBS-T, 0.1%) four times, the plate was filled with streptavidin-HRP solution diluted by the blocking buffer (1:100), which was then reacted for 1 hour. On completion of the reaction, AEC substrate solution was used to induce color development. The color reaction was stopped using tap water when a required size spot was observed (5-10 minutes). The 96 well plate was dried at room temperature, and then, the number of cells secreting IFN-γ was measured by using a microscope.

For the ELISPOT analysis of the invention, spleen cells were used either immediately after being taken (direct ELISPOT) or after being expanded for 5 days stimulation with CT26-hghE2t cells at the mixing volume of spleen cells to CT26-hghE2t cells: $1.5 \times 10^7$ to $1 \times 10^6$ (expanded ELISPOT).

Example 6

Immune Response of HCV E2 Specific Cytotoxic T Lymphocyte (CTL)

The immune response of cytotoxic T lymphocyte was investigated using spleen cells taken from 2-3 mice of each group after treating those mice with a DNA vaccine and a recombinant adenovirus vaccine. In order to stimulate HCV E2 specific cytotoxic T lymphocyte, CT26-hghE2t cell line (H-2d restricted), in which E2 protein is expressed, was treated with mitomycin-C for 30 minutes for the following reaction. Spleen cells were isolated from mice of each group, and about $1.5 \times 10^7$ spleen cells were mixed with $10^6$ CT26-hGHE2t cells in cell culture media (RPMI-1640 medium+ 10% FBS+2 mM glutamine+20 µM β-mercaptoethanol+20 U/µl of mIL-2), followed by stimulation in a 37° C. $CO_2$ incubator for 5 days. New CT26-hghE2t cells, target cells in this embodiment, were plated into each well by $10^4$ cells. after treatment with 1 µCi of $^{51}Cr$ for 2 hours and washing with cell culture media three times. Spleen cells expanded for 5 days were used as effector cells for CTL assay. The effector cells and the target cells were mixed at three different ratios indicated in the figure, which was then reacted for 5 hours. Supernatant was obtained from the culture solution, and the activity of the cytotoxic T lymphocytes was examined by measuring the amount of released $^{51}Cr$ with a gamma radioactivity counter. At that time, a negative control group was prepared by adding only medium to investigate the spontaneous release of $^{51}Cr$. A positive control group was also prepared by adding 2% tween solution to induce maximum release of $^{51}$Cr in every target cells. The way to measure the activity of cytotoxic T lymphocyte was as follows.

% Specific Lysis=$(R_{Max}-R_{eff})/(R_{Max}-R_{spon})\times 100$ $R_{Max}$: Maximum Release
$R_{eff}$: Effector Release
$R_{spon}$: Spontaneous Release Example 7

Enhancement of Immunogenicity by Antigen Engineering of a DNA Vaccine-1

Figure 9:
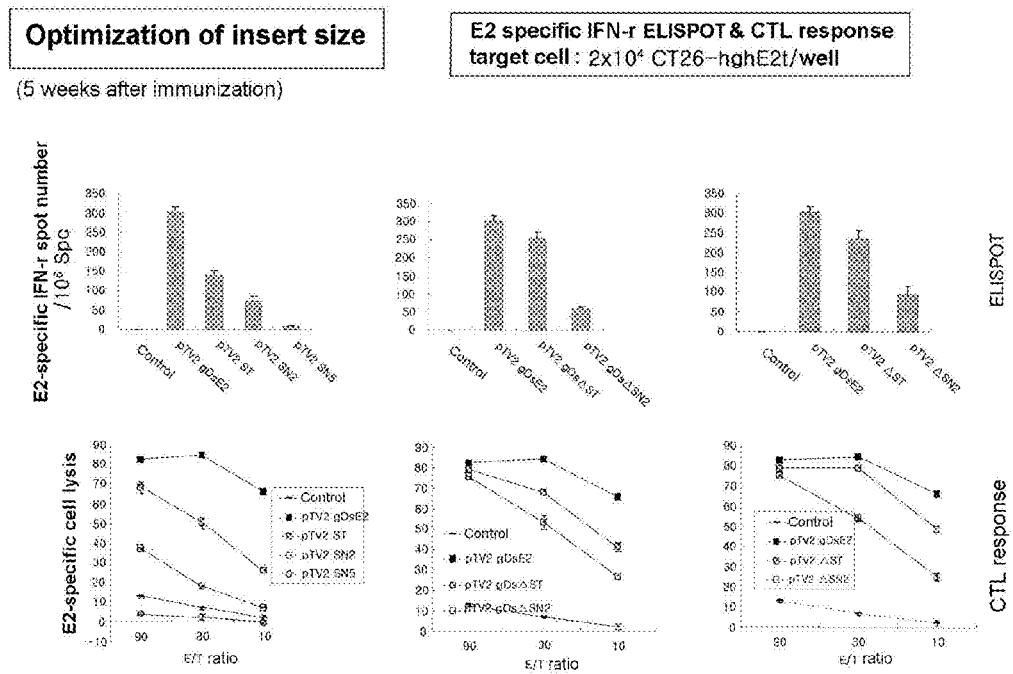
FIG. 9 is a set of graphs showing the cellular immune response 5 weeks after the first immunization. The induced cellular immune response varied in the mouse model according to the way to divide whole HCV gene to make a vaccine.
Figure 10:
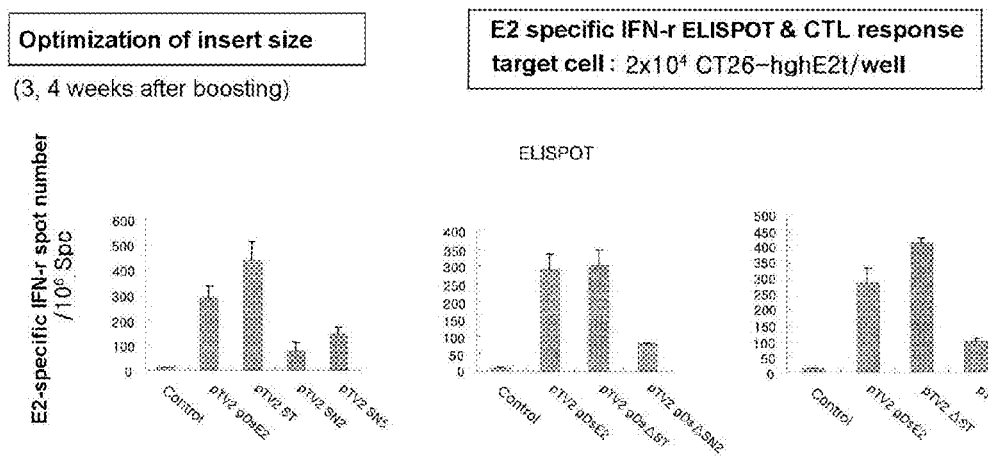
FIG. 10 is a set of graphs showing the cellular immune response 3.4 weeks after the second immunization. The induced cellular immune response varied in the mouse model according to the way to divide whole HCV gene to make a vaccine.

(FIG. 9, FIG. 10: The Effect of the Insert Size in an Expression Vector on the Induction of Cellular Immune Response)

The present inventors investigated what size of insert in a DNA vector was best for the induction of HCV-specific cellular immune response.

For the comparison, a plasmid expressing E2 only and other plasmids having a longer size by including other areas in addition to E2 were used. E2 is translated after E1. At this time, transmembrane domain of E1 functions as a signal sequence for translocation of E2 to ER (Endoplasmic Reticulum). Thus, as for the plasmid expressing E2 only, HSV gDs was inserted at amino terminus of E2 in order to locate the expressed protein to ER. Taking the plasmid as a control vector, other plasmids with different insert lengths, classified in three groups, were compared. First, as a category of plasmids expressing intact HCV core in cytosol, pTV2-ST expressing from core to E2, pTV2-SN2 expressing from core to NS2, and pTV2-SN5 expressing whole HCV gene from core to NS5 were used for the comparison. Second, as a category of plasmids expressing Δ core in cytosol which is deficient of amino terminal 40 amino acids, pTV2-Δ ST and pTV2-Δ SN2 were used. And third, as a category of plasmids expressing Δ Core in ER, pTV2-gDsΔ ST and pTV2-gDsΔ SN2 were used. All the above plasmids were used for immunization by 100 μg each. 5 weeks after the immunization and 3.4 weeks after the second immunization, the response of CD8+ T cells was investigated. CT26-hghE2t cell line was used as a stimulant to investigate E2-specific cytotoxic T lymphocyte response or IFN-γ ELISPOT analysis with E2 since the cell line did not express MHC class II but expressed MHC class I, suggesting that the cell line stimulated CD8+ T cells selectively. That approach was proved to be consistent through the evaluation of cytotoxic T lymphocyte response and IFN-γ ELISPOT analysis performed after stimulating CT26-hghE2t cell lines for 5 days, showing the similar result between the two analyses.

Cellular immune response was observed 5 weeks after the first immunization. As a result, when the first category of plasmids were used, the IFN-γ ELISPOT response observed therein was 47% with pTV2 ST, 23% with pTV2 SN2 and 3% with pTV2 SN5 by taking the rate with pTV2 gDsE2 as a standard (p<0.0001), and 84%, 50%, 18% and 2% of CTL response was observed respectively (FIG. 9). So, cellular immune response was decreased in proportion to the insert length in a DNA vaccine. On the other hand, in the case of plasmid in which Δ Core was expressed in cytoplasm or ER, pTV2 Δ ST showed 77% response, pTV2 Δ SN2 did 31%, pTV2 gDsΔ ST did 84%, and pTV2 gDsΔ SN2 showed 20% of IFN-γ ELISPOT responses, compared with pTV2 gDsE2, suggesting that the plasmid expressing from core to E2 showed similar cellular immune response to the plasmid expressing E2 alone, but the response dropped rapidly after using the plasmid containing more than NS2. The similar result was observed in cytotoxic T lymphocyte response, in which pTV2 gDsE2 showed 84% response, pTV2 Δ ST did 79%, pTV2 Δ SN2 showed 54%, and further pTV2 gDsΔ ST showed 68%, pTV2 gDsΔ SN2 did 53% respectively. Cellular immune response was investigated again 3.4 weeks after the second immunization. Comparing to pTV2 gDsE2, pTV2 ST showed 150%, pTV2 SN2 showed 26%, and pTV2 SN5 showed 50%, and further, pTV2 Δ ST showed 144%, pTV2 Δ SN2 did 35%, pTV2 gDsΔ ST showed 104% and pTV2 gDsΔ SN2 did 26% of IFN-γ ELISPOT responses, suggesting that the DNA vaccine including all from core to E2 has similar or superior immunity to a vaccine including only E2 (FIG. 10). These results suggest that the insert length of a foreign gene expressed in a vector could affect the induction of cellular immune response by E2-specific IFN-γ ELISPOT and CTL analyses.

We speculated that, first, the longer the insert gene was, the less the expression was (FIG. 5). And the expression level seemed to affect the induction of cellular immune response. But, in fact, cellular immune response was not much differ when three different vectors expressing the same antigen but having difference in expression level up to 500 times were used, proved by the succeeding experiments by the present inventors. Therefore, the difference in expression level of antigen seemed not to be the major reason. Second, when an antigen having better immunogenicity than E2 was expressed simultaneously with E2, the immune response to E2 became comparatively decreased because of the antigenic interference. According to the earlier reports, non-structural proteins are superior to structural proteins in the induction of cellular immune response. However, after all the experiments followed by the present inventors, cellular immune response to E2 did not decrease even when the additional plasmid expressing the antigen same as pTV2-SN5 was given for the immunization. That is, the simultaneous expression of non-structural proteins and E2 does not decrease cellular immune response against E2. It is a possible guess that the difference in length of polyprotein might affect any time or any part of antigen-presentation during the procedure of the antigen expression within cells. So, further studies on the mechanisms concerning that cellular immune response is affected by the insert length of a foreign gene expressed in a DNA vector is required.

Example 8

Enhancement of Immunogenicity by Antigen Engineering of a DNA Vaccine-2

Figure 11:
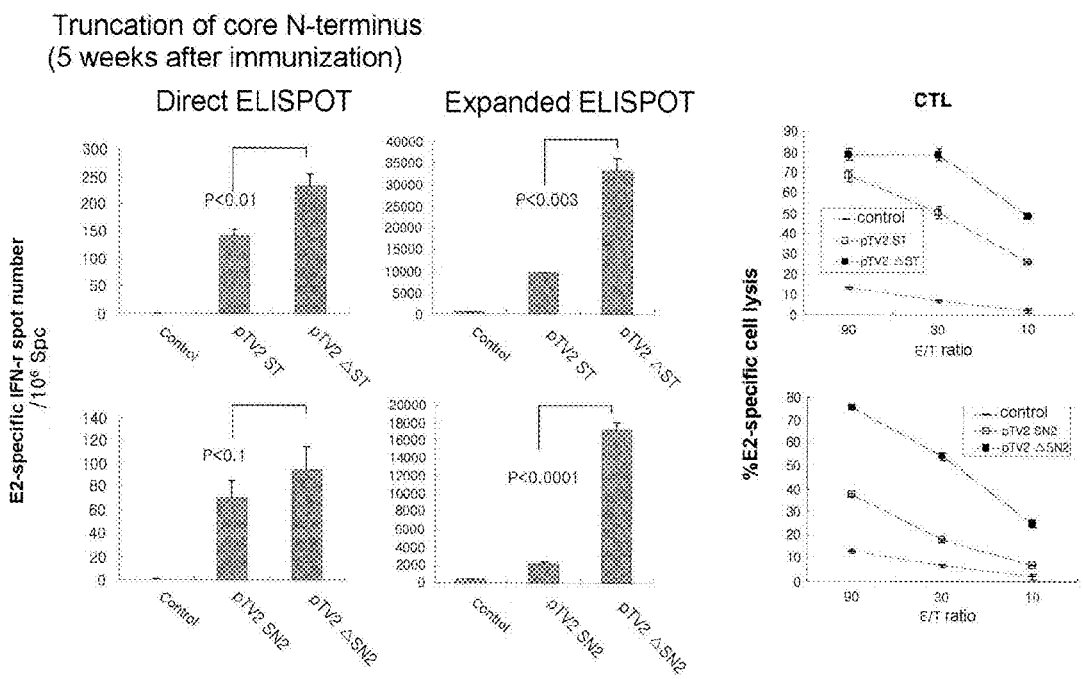
FIG. 11 is a set of graphs showing the cellular immune response 5 weeks after the first immunization. The elimination of amino terminal 40 amino acids of HCV core enhanced cellular immune response in mouse model.

(FIG. 11: The Effect of the Elimination of N-Terminal 40 Amino Acids of Core on the Induction of Cellular Immune Response to E2)

In this example, the effect of a DNA vaccine on hepatitis C virus was investigated. The present inventors tried to reconfirm the immunosuppressive effect of core and at the same time, to provide a way to avoid the immunosuppressive effect of core. The present inventors have reported the immunosuppressive effect of core using antigen presenting cells stably expressing core protein (Lee, *Virology*, 2001, 279:271), and have found through the succeeding studies on deletion mutant in which immunosuppressive effect of core can be prevented by eliminating amino terminal 40 amino acids of core. The embodied example was based on the above preliminary results.

Cellular immune response to E2 was investigated by using the plasmids 'pTV2-ST' and 'pTV2-SN2', both expressing core and reporter antigen E2 simultaneously in cytoplasm. In addition, cellular immune response was also investigated by using the plasmids 'pTV2-Δ ST' and 'pTV2-Δ SN2' in which the same structural proteins are expressed except the elimination of N-terminal 40 amino acids of core. The first immunization was performed with 100 μg of plasmid. 5 weeks later, CD8+ T cellular immune response to E2 was investigated by IFN-γ ELISPOT analysis and cytotoxic T lymphocyte response, using CT26-hghE2t cell line as stimulating cells.

As shown in FIG. 11, there was a difference in cellular immune response to E2 between when intact core was expressed and when a core without N-terminal 40 amino acids was expressed. pTV2-Δ ST and pTV2-Δ SN2 showed each 163% ($p<0.01$) and 134% ($p<0.1$) increased response, compared with pTV2-ST and pTV2-SN2, as determined by the direct IFN-γ ELISPOT. assay. The difference became larger after in vitro stimulation for 5 days to 347% ($p<0.003$) and 800% ($p<0.001$) respectively, as determined by expanded ELISPOT. Similar results to that of ELISPOT response were observed in cytotoxic T lymphocyte response, in which pTV2-ST and pTV2-SN2 showed 50% and 18% of CTL activity each at the 30 E/T ratio, while pTV2-Δ ST and pTV2-Δ SN2 showed 79% and 54% CTL activity respectively. The present inventors repeated three more independent tests based on the consideration that the difference in the induced cellular immune response among the above plasmids was statistically insignificant, which reproduced the same results.

The reports on the effect of core on the immunosuppression have been controversial to each other (Liu, 2002 *J Virol* 76:990; Soguero, 2002 *J Virol* 76: 9345), which suggests that the effect of core is too small to finish the controversy or is detected only under the specific test conditions. In the present invention, though, the immunosuppressive effect of core was observed by direct ELISPOT, even though the difference was not dramatic, and further confirmed to be increased by expanded IFN-γ ELISPOT analysis. In vitro stimulation for 5 days would represent original memory T cells due to the disappearance of effector-stage T cells (Liu, 1997 *J Exp Med* 185:251; Susan, 2002 *Nat Rev* 2:251). Thus, the immunosuppressive effect of core is more likely to be distinguished in the stage of memory T cells rather than in effector T cells. However, further studies to analyze the results of the present invention should be followed since it was not fully probed yet whether the definition on the activation of effector T cells or memory T cells could be applied to the DNA vaccine models as it was. In the succeeding studies by the present inventors, the inventors investigated the effect of core using the same plasmids after the second and the third immunization. As a result, the difference in cellular immune response was decreased or vanished. That is, the effect of core is insignificant or just shown temporarily. According to the reports on the characteristics of HCV antigen specific T cells in the early stage of HCV infection, there is a stage of stunned phenotype, precisely during which division is going on but IFN-γ is not secreted, and after passing through the stage, IFN-γ becomes secreted again (Lechner, 2000 *J Exp Med* 191:1499). Taking this and the results of the embodiments of the present invention together into consideration, core seems to have a temporary immunosuppressive effect.

In the example of the present invention, intact core expressed in cytoplasm has immunosuppressive effect, and the effect disappeared when amino terminal 40 amino acids were eliminated. Thus, the present invention provides a method for enhancing the cellular immune response to HCV, even with core keeping amino acids most, by eliminating the immunosuppressive effect of core protein.

Example 9

Enhancement of Immunogenicity by Antigen Engineering of a DNA Vaccine-3

Figure 12:
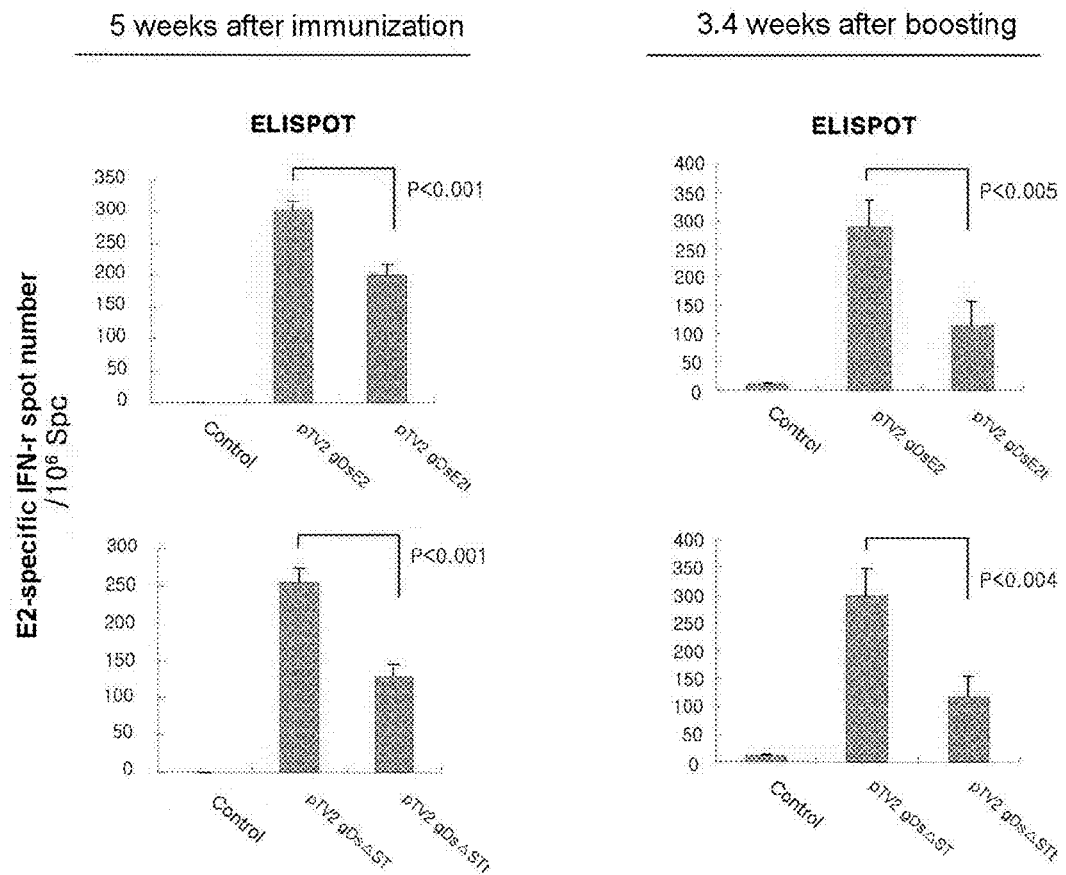
FIG. 12 is a set of graphs showing the cellular immune response 5 weeks after the first immunization or 3.4 weeks after the second immunization. Cellular immune response was better induced by HCV E2 DNA with transmembrane domain than by that without it.

(FIG. 12: The Difference in Cellular Immune Response Caused by the Existence of Transmembrane Domain of E2)

In the aspect of immunogenicity of E2, the changes of cellular immune response to E2 by transmembrane domain were investigated in this example.

In order to achieve the object, the plasmid pTV2 gDsE2 expressing E2 only and the other plasmid pTV2 gDsΔ ST expressing Δ Core-E1-E2 all were used. As control groups, pTV2 gDsE2t and pTV2 gDsΔ STt without transmembrane domain of E2 were used. Each plasmid was used for immunization by 100 μg. 5 weeks after the first immunization or 3.4 weeks after the second immunization, cellular immune response to E2 was observed by IFN-γ ELISPOT assay. After the first immunization, CT26-hghE2t cell line was used for the stimulation, and after the second immunization, peptide pool for E2 was used for the stimulation. The former could stimulate only CD8+ T cells, and the latter could stimulate not only CD8+ T cells but also CD4+ T cells.

As shown in FIG. 12, pTV2 gDsE2t and pTV2 gDsΔ STt showed 66% ($p<0.001$) and 50% ($p<0.001$) response respectively on the $5^{th}$ week from the first immunization, and 40% ($p<0.005$) and 39% ($p<0.004$) each on the $3.4^{th}$ week from the second immunization, compared with pTV2 gDsE2 and pTV2 gDsΔ ST. Thus, even though whole structural protein was expressed along with E2, cellular immune response to E2 was decreased by the elimination of transmembrane domain of E2.

If T cell epitope was present in transmembrane domain of E2, such result would have been produced. In the embodiment of the present invention, in order to get rid of such possibility, a cell line expressing E2 without transmembrane domain (CT26-hghE2t cell line) was used, and besides, a peptide pool was also prepared by eliminating transmembrane domain of E2. Therefore, the result of the invention has nothing to do with epitope present in transmembrane domain. And thus, the results might be in the bounds of possibility as follows; First, The extracellular secretion of E2 was induced by the elimination of transmembrane domain. That is, E2 protein stays short in cells as its transmembrane domain is removed. In regard to antigen presenting process, protein is processed by proteasome to be loaded on MHC class I molecule during the protein synthesis, which was then exposed on cell surface through ER by secretory system. But, exceptionally, dendritic cells among antigen presenting cells could stimulate CD8+ T cells by a certain mechanism in which a part of the protein in endosome can be loaded on MHC class I molecule in ER through cross presentation (Heath, 2001 *Nat Rev Immunol* 1:126). It suggests that even a protein after synthesis can join class I antigen presentation pathway. So, the induction of extracellular secretion has an advantage to induce antibody response effectively but a disadvantage not to induce cellular immune response effectively by the short stay in a cell. Second, the difference of a protein structure resulted from the presence or the absence of transmembrane domain might cause changes in many stages related to antigen presenting process. A membrane protein requires a lipid membrane component to keep the structure stable. The changes in physiochemical characteristics of a protein generated from being produced in cytoplasm to be participated in the antigen presenting process results in the difference observed through antigen presenting process.

The result of this example of the present invention suggested that the elimination of transmembrane domain of E2 protein played a negative role in inducing cellular immune response, so that a DNA vaccine containing transmembrane domain was required for optimal induction of cellular immune response.

There was not much difference in enhancement of immunity by antigen engineering of a DNA vaccine among all the above individual examples, but it was uncertain whether all the substances would have cumulative effect or synergistic effect when they worked altogether for the treatment of a disease. Especially for a virus rapidly producing diverse quasispecies, like HIV or HCV, the valance between immune response and the viral replication is very important to decide whether the viral infection can be cleared or progress to chronic infection. Thus, the above example provides a new approach to enhance cellular immune response by antigen engineering in HCV DNA vaccine model.

Example 10

Figure 13:
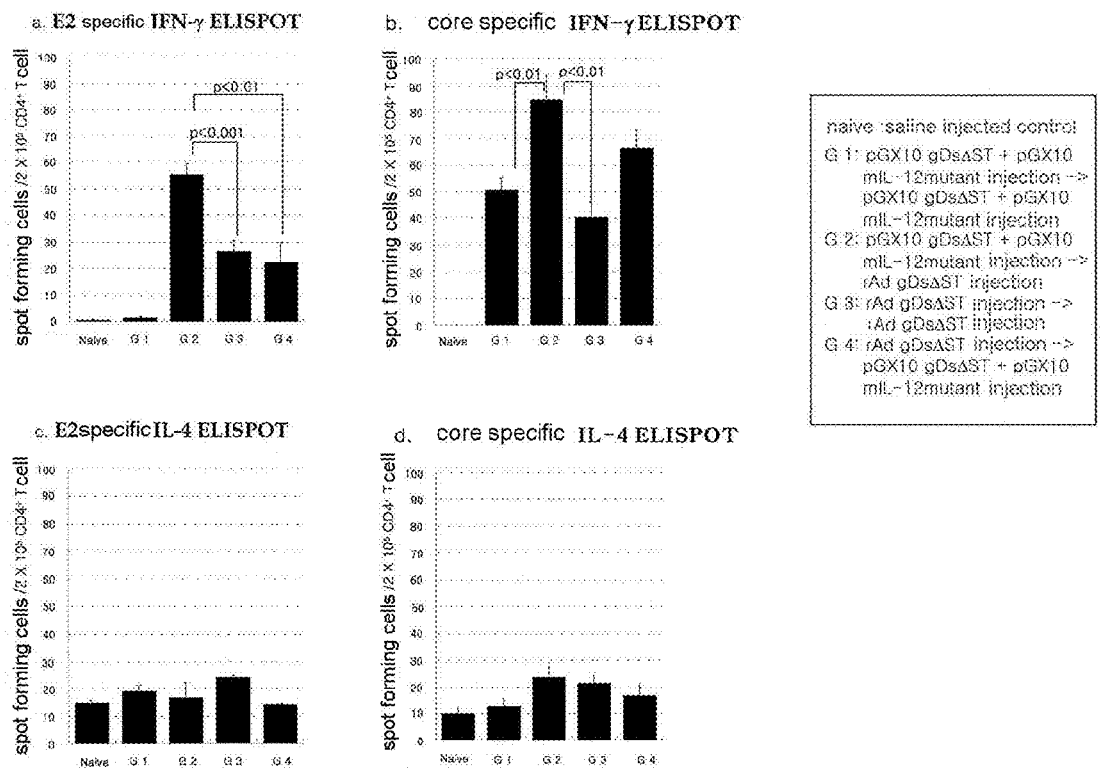
FIG. 13 is a set of graphs in which mouse CD4+ T cells were separated by MACS (magnetic associated cell sorting) for the reaction with HCV E2 or core protein, and the resultant CD4+ T cells secreting IFN-γ or IL-4 were quantified, Naive: Saline injected control, G1: pGX10 gDsΔ ST+pGX10-mIL-12 mutant injection→pGX10 gDsΔ ST+pGX10-mIL-12 mutant injection G2: pGX10 gDsΔ ST+pGX10-mIL-12 mutant injection→rAd gDsΔ ST injection, G3: rAd gDsΔ ST injection→rAd gDsΔ ST injection, G4: rAd gDsΔ ST injection→pGX10 gDsΔ ST+pGX10-mIL-12 mutant injection

Quantification of HCV E2- or Core-Specific CD4+ T Cells Secreting IFN-γ and IL-4 (FIG. 13)

The present inventors searched a kind of vaccine and a method including the administration of the same to induce maximum Th1 immune response, a protective immunity against HCV infection. At first, 4 mice from each group were taken to isolate their spleens. $5 \times 10^7$ spleen cells were re-suspended in 450 μl of MACS buffer solution (0.5% BSA, 2 mM EDTA in PBS), and then mixed with 50 μl of MACS antibody bead, followed by a reaction at 4° C. for 15 minutes. After finishing the reaction, the mixture was washed with 5 ml of MACS buffer solution twice, and then, the samples were re-suspended in 500 μl of MACS buffer solution. Equilibration of MACS mini-column was performed with 500 μl of MACS buffer solution, which was exposed on magnetic field. The sample was loaded on the above column. After the buffer solution was spilled out completely, the column was washed with MACS buffer solution three times. Magnetic field was removed from the column to elute with 500 μl of MACS buffer solution. FACS analysis was performed for the obtained cells, from which 90% of those were confirmed to be CD4+ T cells. ELISPOT analysis was performed to quantify those cells secreting IFN-γ and IL-4.

As a result, relatively great numbers of HCV E2- and core-specific CD4+ T cells secreting IFN-γ were produced by DNA priming-rAd boosting method of the invention, compared with other vaccine administrating methods (FIG. 13A and FIG. 13B, G2, p<0.001). When just DNA was injected twice, E2-specific IFN-γ producing CD4+ T cells were hardly observed (FIG. 13A, G1), but those producing core specific IFN-γ were induced as much as in the group treated with rAd twice (FIG. 13B, G1). That was because the core protein itself, unlike E2, could efficiently induce the immunity of CD4+ T cells simply by DNA immunization. On the contrary, from the results of IL-4 ELISPOT analysis, core- and E2-specific CD4+ T cells, synthesizing IL-4 were hardly detected in every group (FIG. 13C and FIG. 13D). That was because a DNA vaccine and an adenovirus vaccine induced the immune response to Th1 type than to Th2. Considering all the above results, the present inventors confirmed that the DNA priming-rAd boosting method was most effective to induce the CD4+ Th1 immune response than rAd priming-DNA boosting or twice injection of an adenovirus.

Example 11

Figure 14:
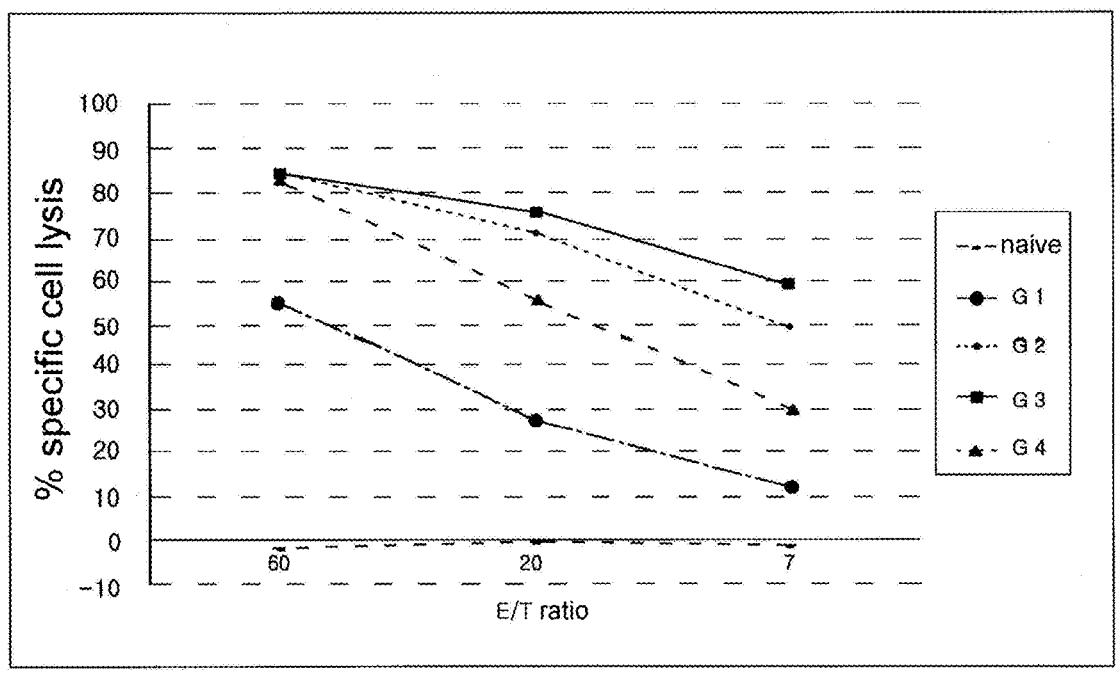
FIG. 14 is a graph showing the result of the cell lysis assay using CT26-hGHE2t cell line expressing HCV E2 antigen, –: control, ●: G1, ◆: G2.

Investigation of HCV E2-Specific Cytotoxic T Lymphocyte Response (FIG. 14)

Each group was treated with a DNA and a recombinant adenovirus vaccine. Two mice from each group were taken to isolate their spleen cells for the investigation of the cytotoxic T lymphocyte immune response. CT26-hghE2t cell line (H-2d restricted) expressing E2 was used to stimulate HCV E2 specific cytotoxic T lymphocytes.

As a result, twice injection of the adenovirus and the DNA priming-rAd boosting method were both proved to be effective without a significant difference between them (FIG. 14, G2 and G3). Although rAd priming-DNA boosting method and twice injection of DNA induced the specific cytotoxic T lymphocyte response, the effect was not like the above two methods (FIG. 14, G1 and G4). Thus, DNA priming-rAd boosting immunization was most effective to induce the cytotoxic T lymphocyte immune response.

Example 12

Immunization of Chimpanzees using an Immunogenic Plasmid and a Recombinant Adenovirus and the Challenge with Infectious Hepatitis C Virus (FIG. 15)

All the records on the chimpanzees used for the experiments were presented in Table 1. For the test group 1 and group 2, 6 mg of HC102 DNA vaccine and 8 mg of HC103 DNA vaccine were dissolved in PBS by the concentration of 2 mg/ml respectively, and 0.75 ml of HC102 and 1 ml of HC103 were injected intramuscularly into 4 spots of right and left deltoid muscle and right and left gluteus maximus, for the group 1 and group 2 respectively, three times at intervals of 8 weeks. 30 weeks after then, $1 \times 10^{10}$ pfu of recombinant adenovirus (rAd gDsΔ ST, rAd gDsNS34, rAd NS5) were dissolved in 1.6 ml of suspension buffer (10 mM Tris, 4% sucrose, 2 mM $MgCl_2$. pH 8.0), which was also injected intramuscularly into the same 4 spots where a DNA vaccine was injected by 0.4 ml. 12 weeks after the final immunization with the recombinant adenovirus, an intravenous injection with HCV-bk challenging inoculum having the concentration of 100 $CID_{50}$/ml was performed on right femoral vein by 1 ml/chimpanzee.

TABLE 1

| Vaccine | Chimpanzee | Name | Gender | Date of Birth | Mother | HCV infection of mother | Infection period of mother | Exposure to HBV | Exposure to HCV |
|---|---|---|---|---|---|---|---|---|---|
| Control | 404 | Chop Suey | F | Sep. 12, 1994 | Spring Roll | Recovered | 96.9-96.12 | — | — |
|  | 406 | Noli | F | Nov. 25, 1994 | Annie | Recovered | 89.8-90.2 | — | — |
| HC102/ | 376 | Sabel | F | Aug. 25, 1991 | Mabel | — | — | — | — |
| rAd | 393 | Sally | F | Nov. 2, 1992 | Lucy | — | — | — | — |

TABLE 1-continued

| Vaccine | Chimpanzee | Name | Gender | Date of Birth | Mother | HCV infection of mother | Infection period of mother | Exposure to HBV | Exposure to HCV |
|---|---|---|---|---|---|---|---|---|---|
| HC102 | 400 | Pasiway | M | May 9, 1994 | Pasimani | — | | — | — |
| HC103/rAd | 381 | Troy | F | Oct. 19, 1991 | Helen | — | | — | — |
| | 397 | Root Bear | F | Dec. 5, 1993 | Sarsaparilla | Recovered | 88.8-88.11 | — | — |
| HC103 | 402 | Lawrence | M | Jul. 2, 1994 | Juno | — | | — | — |

Example 13

Isolation of the Immunized Cells from Chimpanzees

Blood was taken from right femoral vein of chimpanzee with 10 ml heparinized vacutainer. PBMC (peripheral blood mononuclear cell) was isolated for the investigation of cellular immune response.

Blood in the two heparinized vacutainers was diluted using RPMI-1640 medium to make a total volume 30 ml, which was then transferred by pipette into 50 ml conical tube containing 15 ml of lymphocyte separation medium (Cellgro Mediatech, Cat# 25-072-CV) to let them form each layer. Centrifugation was performed with the mixture at room temperature with 1800 RPM for 20 minutes with a centrifuge (Eppendorf refrigerated tabletop centrifuge). Plasma in the upper layer was removed. The below PBMC layer was separated carefully with a pipette, and then transferred into a 50 ml fresh conical tube. The layer was diluted with RPMI-1640 medium to make a total volume 50 ml. Centrifugation was performed again under the same speed and temperature for 10 minutes to eliminate supernatant. The process was repeated two more times, and the separated PBMC was washed completely. The product was diluted with 0.4% tryphan blue (Sigma, Cat# 8154) to quantify the cells with a hemacytometer, which was later used for the investigation of cellular immune response.

Example 14

IFN-ɤ ELISPOT Analysis using Chimpanzee PBMC

IFN-ɤ ELSIPOT analysis was performed using PBMC obtained from the immunized chimpanzees by following the manufacturer's instruction. IFN-ɤ ELISPOT kit (MABTECH Co., Cat# M34201-H) was used for this invention. Precisely, antibody (1-D1K) to IFN-ɤ was diluted with PBS by the concentration of 5 μg/ml, which was plated on a 96 well plate (Millipore, 0.45m, Cat# MAHAS4510, Bedford, Mass.) by 50 μl/well. The plate was left at room temperature for over 12 hours. The remaining antibody solution was removed by suction. Then, the plate was washed with PBS twice. Animal cell culture medium (RPMI 1640 containing 50 units/ml penicillin, 50 μg/ml streptomycin, 50 μM β-mercaptoethanol, 100 M MEM non-essential amino acid, 2 mM L-glutamine, 1 mM sodium pyruvate, 10 mM HEPES, 20 Units/ml recombinant hIL-2 and 1% ABS (human AB serum, Valley Biomedical, Lot# A20124)) was added to each well by 200 μl. The plate was left again at 37° C. for over 2 hours, followed by suction. The separated PBMC was plated thereto by $3\times10^5$ cells/well. In order to investigate HCV-specific cellular immune response, peptide pool was added by 1 μg/ml per each peptide. For the positive control, phytohemagglutinin (PHA) was treated by 2.5 μg/ml. The 96 well plate was put in a 37° C. 5% $CO_2$ incubator and left for 18 hours without agitation. The contents of the 96 well plate were thrown off. And the plate was washed with washing solution (PBS-T, 0.1%) containing 0.1% tween 20 (Sigma, Cat# D8654) four times. Biotin-conjugated mAb (7-B6-1 biotin) was diluted with blocking buffer prepared by adding 1% BSA to washing solution to make the final concentration of 1 μg/ml, which was added to each well by 50 μl, leading to a reaction for 2 hours. The plate was washed with the washing solution (PBS-T, 0.1%) four times and filled with streptavidin-HRP solution that was diluted by the blocking buffer at the ratio of 100:1. Reaction was followed for an hour. After finishing the reaction, AEC substrate solution was used to induce color development. The color development was stopped by using tap water when the spot with expected size was observed (5-10 minutes). The 96-well plate was dried at room temperature. And the cells secreting IFN-ɤ were quantified by ELISPOT reader.

The above experiment was carried out on the $2^{nd}$ week after boosting with a recombinant adenovirus. As a result, even though there was a slight difference between individuals, over 1000 IFN-ɤ secreting cells per a million PBMCs were detected in 4 of 6 chimpanzees. Even much less, the rest 2 chimpanzees produced 400-600 HCV antigen specific immune cells. No difference was observed between experimental group 1 and group 2. Also, over 1200 IFN-ɤ secreting cells per a million immune cells were found in #404 chimpanzee, a control group of chimpanzee. That was not because the examples of the present invention reflected non-specific immune response, but because the target was exposed on HCV under the infectious dose once in the past. In that case, viremia was not developed, but the induced cellular immune response was memorized long enough to show a specific response later (Shata M T, 2002, 9*th International Meeting on HCV and Related Viruses*, P-215), which is consistent with the recent test results of New York Blood Center. Thus, there is no doubt about that the methods of the present invention effectively induce cellular immune response in large animal model.

Example 15

Quantification of IFN-ɤ Secretion by CD4+ T Cells and T Cell Proliferation Assay in Chimpanzees 2 weeks after boosting with a recombinant adenovirus, PBMC was isolated by the procedure mentioned above to quantify HCV antigen specific IFN-ɤ secretion by CD4+ T cells. IFN-ɤ ELISA kit (BD pharmingen Co.) was used in this example. PBMC, separated from chimpanzee, was diluted with growth medium (RPMI-1640 containing 50 units/ml penicillin, 50 μg/ml streptomycin, 50 μM β-mercaptoethanol, 100 M MEM non-essential amino acid, 2 mM L-glutamine, 1 mM sodium pyruvate, 10 mM HEPES and 10% ABS (human AB serum, Valley Biomedical, Lot# A20124)) in the absence of human recombinant IL-2, and then distributed in a round 96 well plate ($2>10^5$ cells/well). And stimulation with specific antigens was given. PHA having the final concentration of 2.5 μg/ml was selected as a positive control. As an HCV specific antigen, 5 μg/ml of recombinant GST-Core, GST- NS3, and NS5 proteins were used, and a recombinant human SOD (superoxide dismutase) was used for a negative control. The plate was cultured for 5 days in a 37° C., 5% $CO_2$ incubator. On the $5^{th}$ day, 100 μl of culture supernatant was taken for the quantification of IFN-γ using IFN-γ ELISA kit (BD pharmingen Co.) by following the standard protocol of the manufacturer. On the other hand, $^3$H-thymidine was added to the remaining cells on 96-well plate by 1 μCi/well to investigate CD4+ T cell proliferation. 18 hours after adding $^3$H-thymidine, cells were harvested on a glass filter paper (Wallac, Finland, Cat# 1205-401) using an automatic cell harvester (Micro 96 Cell harvester, Model 11055, Skatron Instruments Inc, Va.), after which the amount of $^3$H-thymidine incorporated was measured by a liquid scintillation counter (Microbeta Plus 1450 Liquid Scintillation Counter, Wallac, Finland). The stimulation index was calculated by dividing the amount of HCV antigen-specific radioactivity (cpm) incorporation by SOD-specific radioactivity (cpm) incorporation.

As a result of this example in which IFN-γ secretion by CD4+ T cell was investigated, a specific response to HCV nonstructural protein was observed in chimpanzees administered with the vaccine, which was, though, very weak in the control group. This result coincides with the earlier report that the nonstructural protein among many antigens of HCV could induce cellular immune response better (Missale, 1996, *J Clin Invest* 98: 706). IFN-γ secretion in experimental group 1 was greater than that in group 2.

It was also confirmed from the observation on CD4+ T cell proliferation that HCV nonstructural protein specific stimulation index was 20 at average in the vaccine-administered group. T-cell proliferative response showed similar result to IFN-γ secretion by CD4+ T cells in general, but just one chimpanzee (#406) in the control group showed the similar level of an antigen specific response to chimpanzees in the vaccinated groups. That was also resulted from the previous exposure as explained above.

Therefore, it was confirmed by the examples of the invention that the vaccine and the method of the present invention could induce cellular immune response effectively even in large animal model like chimpanzee.

Example 16

Quantification of Hepatitis C Virus in Chimpanzees

After the challenge with infectious hepatitis C virus, how cellular immune response induced by the present invention controls hepatitis C virus replication was investigated by measuring the amount of the virus in blood. The plasma taken from the blood of chimpanzees was used for the quantification using real time RT-PCR at New York Blood Center. And quantitative PCR was performed. Taking the standard HCV RNA, which was quantified already, as a standard, 10 μl of plasma sample was mixed with RT mix (4 μl of 5×RT buffer from Gibco, 1 μl of 100 mM DTT, 1 μl of 10 mM dNTP, 0.5 μl of 100 μM HCV-R primer (SEQ. ID. No 37), 0.1 μl of 4 U/μl RNasin, 0.1 μl of 200 U/μl M-MLV and 3.3 μl of $H_2O$) containing 10 μl of M-MLV reverse transcriptase. Then, reverse transcription was performed at 42° C. 30 μl of PCR mix (3 μl of PCR buffer, 4 μl of 200 mM $MgCl_2$, 0.05 μl of 100 μM HCV-F primer (SEQ. ID. No 38), 1 μl of 200 ng/μl CMB3 fluorescent probe (5-FAM SEQ. ID. No 39 DABCYL-3), 0.25 μl of 5 U/μl TaqGold polymerase, 21.7 μl of $H_2O$) was added to the above RT product and PCR was performed using a PCR machine (PE 7700, Perkin Elmer). The condition of the PCR was as follows: preheating at 95° C. for 10 minutes, at 95° C. for 30 seconds, at 55° C. for 60 seconds and at 72° C. for 30 seconds, making 45 cycles in total. On completion, the amount of the virus RNA was calculated with software provided by PE 7700 PCR machine.

Quantification was carried out on 0, $2^{nd}$, and $4^{th}$ week from the challenge with 100 $CID_{50}$ of infectious hepatitis C virus. Thus, the results reflected the virus replication in the early stage of infection. The amount of the virus was $10^{5.45}$ and $10^6$ each on the $2^{nd}$ and $4^{th}$ week in the control. This result reflected the infectivity of the infectious virus of the invention, and the measured value was good enough for the comparison with the experimental group. On the other hand, 5 of the chimpanzees in the experimental group administered with a vaccine were confirmed not to have virus on the $2^{nd}$ week. The virus levels of #400 and #381 were near the detection limit ($10^{2.95}$) of the assay, so that re-test was performed, resulting in no detection of the virus. However, the level on the $4^{th}$ week was a little higher than the detection limit. The test results were presented as a mean value. There was as 100 times as difference in the average virus number between the chimpanzees of the experimental group and those of the control. As for the chimpanzees in the control group (naïve) in which immune response to HCV was not induced, the virus began to be detected from 1.02-1.14 week after the challenge, and the maximum virus content ($10^{5.8}$) was observed on the $6^{th}$ week (Prince A M, 2002, *9th International Meeting on HCV and Related Viruses*, P-259). As for the chimpanzees in which the protective immunity to HCV was memorized by experiencing the infection already, the maximum value of the virus was dropped 10-100 times after the re-challenge, compared with the value of the first infection. In addition, the virus stayed short and the time point of the maximum virus became advanced (Bassett S E, 2001, *Hepatology* 33:1479-1487). Taking all the results of the embodiments of the invention into consideration, the vaccine and the method of the present invention are believed to not only induce antigen specific cellular immunity but also control HCV replication during the acute phase of infection. Though, in order to make sure that the protective effect against the infection in the early stage can go far to inhibit the chronic infection, the continuous observation after the infection was required for a long while. The present invention confirmed that the vaccine of the present invention could induce the protective immunity to the infectious virus in chimpanzees, the only available test animal for HCV.

As a result, the vaccine of the present invention developed by the antigen engineering in small animal, and the DNA priming-recombinant adenovirus boosting method of the present invention, which enhances the Th1 immune response, can induce cellular immune response effectively in chimpanzee model resembled in human most, and further the induced cellular immune response can function as a protective immunity against HCV infection.

INDUSTRIAL APPLICABILITY

As explained hereinbefore, the plasmid of the present invention used a whole HCV gene as a vaccine to induce multi-epitope-specific cellular immune response. And after determining the optimum size, the whole gene was divided into 3 parts to prepare a DNA vaccine having efficient immunogenicity. In addition, amino terminal 40 amino acids of core were deleted to eliminate its immunosuppressive function, but transmembrane domain of E2 was still included to produce a vaccine having greater immunogenicity. On consideration of Th1 immune response, which is important protective immunity to HCV, the vaccination regimen using DNA priming-recombinant adenovirus boosting was selected, which showed higher CD4+ T cell response than when DNA priming and recombinant adenovirus boosting were used individually. The present inventors have observed that the efficient cellular immune response was induced in chimpanzees, the only available test animal for HCV, and the infectious hepatitis C virus was effectively controlled in the early stage of infection by the vaccine of the present invention. Therefore, the vaccine of the present invention can be effectively used as a vaccine for hepatitis C virus.

Those skilled in the art will appreciate that the conceptions and specific embodiments disclosed in the foregoing description may be readily utilized as a basis for modifying or designing other embodiments for carrying out the same purposes of the present invention. Those skilled in the art will also appreciate that such equivalent embodiments do not depart from the spirit and scope of the invention as set forth in the appended claims.

What is claimed is:

1. A plasmid mixture comprising:

a first plasmid containing a DNA fragment encoding a structural protein composed of core, E1 and E2 proteins of hepatitis C virus, in which 35-40 amino acids are eliminated from the N-terminal region of the original core protein;

a second plasmid containing a DNA fragment encoding a non-structural protein of hepatitis of hepatitis C virus composed of NS3 and NS4 of hepatitis C virus; and a third plasmid containing a DNA fragment encoding NS5 of hepatitis C virus, wherein the size of the DNA fragments contained in the first, second and third plasmids ranges from 2 to 6 kb, and wherein the first plasmid contains SEQ ID No 50, the second plasmid contains SEQ ID No 51, and the third plasmid contains SEQ ID No 52.

2. The plasmid mixture as set forth in claim 1, wherein 40 amino acids are eliminated from the N-terminal region of the original core protein in the first plasmid.

3. The plasmid mixture as set forth in claim 1, wherein the E2 protein contains a transmembrane domain of an E2 protein.

4. The plasmid mixture as set forth in claim 1, wherein the first plasmid is pGX10 gpsΔST (Accession No: KCCM 10415).

5. The plasmid mixture as set forth in claim 1, wherein the second plasmid is pGX10 NS34 (Accession No: KCCM 10417).

6. The plasmid mixture as set forth in claim 1, wherein the third plasmid is pGX10 N5 (Accession No: KCCM 10416).

7. The plasmid mixture as set forth in claim 1, wherein the first plasmid is pGX10 gps ST (Accession No: KCCM 10415), the second plasmid is pGX10 NS34 (Accession No: KCCM 10417), and the third plasmid is pGX10 NS5 (Accession No: KCCM 10416).

8. The plasmid mixture as set forth in claim 7, further comprising pGX10 hIL-12m.

9. A recombinant adenovirus mixture comprising:

a first adenovirus containing a DNA fragment encoding a structural protein composed of core, E1 and E2 proteins of hepatitis C virus, in which 35-40 amino acids are eliminated from N-terminal of the original core protein;

a second adenovirus containing a DNA fragment encoding a non-structural protein composed of NS3 and NS4 of hepatitis C virus; and a third adenovirus containing a DNA fragment encoding NS5 of hepatitis C virus, wherein the size of the DNA fragments contained in the first, second and third adenoviruses ranges from 2 to 6 kb, and wherein the first adenovirus contains SEQ ID No 50, the second adenovirus contains SEQ ID No 54, and the third adenovirus contains SEQ ID No 52.

10. The recombinant adenovirus mixture as set forth in claim 9, wherein 40 amino acids are eliminated from the N-terminal of the original core protein.

11. The recombinant adenovirus mixture as set forth in claim 9, wherein the E2 protein contains a transmembrane domain of an E2 protein.

12. The recombinant adenovirus mixture as set forth in claim 9, wherein the first adenovirus is rAd gDsΔST (Accession No: KCCM 10418).

13. The recombinant adenovirus mixture as set forth in claim 9, wherein the second adenovirus is rAd gDs NS34 (Accession No: KCCM 10420).

14. The recombinant adenovirus mixture as set forth in claim 9, wherein the third adenovirus is rAd NS5 (Accession No: KCCM 10419).

15. The recombinant adenovirus mixture as set forth in claim 9, wherein the first adenovirus is rAd gDsΔST (Accession No: KCCM 10418), the second adenovirus is rAd gDs NS34 (Accession No: KCCM 10420), and the third adenovirus is rAd NS5 (Accession No: KCCM 10419).

16. A method of inducing an immune response to hepatitis C virus comprising:

priming with the plasmid mixture of claim 1;

boosting with a recombinant adenovirus mixture that comprises:

a first adenovirus containing a DNA fragment encoding a structural protein composed of core, E1 and E2 of hepatitis C virus, in which 35-40 amino acids are eliminated from N-terminal of the original core protein;

a second adenovirus containing a DNA fragment encoding a non-structural protein composed of NS3 and NS4 of hepatitis C virus; and a third adenovirus containing a DNA fragment encoding NS5 of hepatitis C virus, wherein the size of the DNA fragments contained in the first, second and third adenoviruses ranges from 2 to 6 kb, and wherein the first adenovirus contains SEQ ID No 50, the second adenovirus contains SEQ ID No 54, and the third adenovirus contains SEQ ID No 52.

17. The method as set forth in claim 16, wherein boosting with the recombinant adenovirus mixture is conducted once after priming with the plasmid mixture three times.

18. The method as set forth in claim 16, wherein the boosting with the recombinant adenovirus mixture after priming with the plasmid mixture induces the CD4+ Th1 immune response.

19. The method as set forth in claim 18, wherein the boosting with the recombinant adenovirus mixture once after priming with the plasmid mixture three times induces the CD4+ Th1 immune response.

20. The plasmid mixture of claim 1, wherein the plasmid mixture induces cytotoxic T lymphocyte response in a person immunized with the plasmid mixture.

21. The recombinant adenovirus mixture of claim 9, wherein the recombinant adenovirus mixture induces cytotoxic T lymphocyte response in a person immunized with the recombinant adenovirus mixture.

* * * * *